United States Patent
Pell et al.

(10) Patent No.: US 9,861,272 B2
(45) Date of Patent: Jan. 9, 2018

(54) APPARATUS, SYSTEMS, AND METHODS FOR PERFORMING LAPAROSCOPIC SURGERY

(71) Applicant: The Board of Trustees of the Leland Stanford Junior University, Palo Alto, CA (US)

(72) Inventors: Christopher Steven Pell, San Rafael, CA (US); Bryan J. Duggan, Ortonville, MI (US); Hattie Zhi Chen Dong, Stanford, CA (US); Thomas Ruby, Mountain View, CA (US); John Avi Roop, Menlo Park, CA (US); Jonathan B. Ticker, Glen Head, NY (US); James N. Lau, Palo Alto, CA (US); Kevin Chao, Palo Alto, CA (US)

(73) Assignee: THE BOARD OF TRUSTEES OF THE LELAND STANDFORD JUNIOR UNIVERSITY, Palo Alto, CA (US)

( * ) Notice: Subject to any disclaimer, the term of this patent is extended or adjusted under 35 U.S.C. 154(b) by 892 days.

(21) Appl. No.: 13/966,197

(22) Filed: Aug. 13, 2013

(65) Prior Publication Data
US 2013/0331646 A1    Dec. 12, 2013

Related U.S. Application Data

(63) Continuation of application No. PCT/US2012/025136, filed on Feb. 14, 2012.
(Continued)

(51) Int. Cl.
*A61B 17/29*  (2006.01)
*A61B 1/313*  (2006.01)
(Continued)

(52) U.S. Cl.
CPC .......... *A61B 1/3132* (2013.01); *A61B 17/29* (2013.01); *A61B 2017/00265* (2013.01);
(Continued)

(58) Field of Classification Search
CPC ............... A61B 17/29; A61B 1/3132; A61B 2017/00265; A61B 2017/00362;
(Continued)

(56) References Cited

U.S. PATENT DOCUMENTS

| 4,572,038 A | 2/1986 | Graham |
| 5,308,358 A | 5/1994 | Bond et al. |

(Continued)

FOREIGN PATENT DOCUMENTS

| WO | WO-2010114634 A1 * | 10/2010 | .............. A61B 17/94 |
| WO | 2011089565 A1 | 7/2011 | |

OTHER PUBLICATIONS

Korean Intellectual Property Office, PCT International Preliminary Report on Patentability for PCT/US2012/025136, Applicant: The Board of Trustees of the Leland Stanford Junior University, Forms PCT/IB/373 and PCT/ISA/237; dated Sep. 19, 2012, 8 pages.

*Primary Examiner* — Kathleen Holwerda
*Assistant Examiner* — Socrates L Boutsikaris
(74) *Attorney, Agent, or Firm* — William A. English; Vista IP Law Group LLP

(57) ABSTRACT

Apparatus, systems, and methods for laparoscopic abdominal surgery are disclosed. For example, a system or kit is provided for performing a procedure within a surgical space within a patient's body that includes a plurality of tool heads, and a tool head carrier including features for removably receiving one or more tool heads, the tool head carrier sized for introduction through a trocar or other port into a surgical space. The system or kit may also include a surgical tool including a tool shaft introduceable into the surgical
(Continued)

space and including features for securing a tool head to the tool. Optionally, the tool head carrier may include a clip for securing the tool head carrier to an endoscope.

18 Claims, 55 Drawing Sheets

Related U.S. Application Data

(60) Provisional application No. 61/442,788, filed on Feb. 14, 2011.

(51) Int. Cl.
*A61B 17/00* (2006.01)
*A61B 90/00* (2016.01)

(52) U.S. Cl.
CPC ............. *A61B 2017/00362* (2013.01); *A61B 2017/00455* (2013.01); *A61B 2017/00473* (2013.01); *A61B 2017/292* (2013.01); *A61B 2017/2927* (2013.01); *A61B 2017/2929* (2013.01); *A61B 2017/2931* (2013.01); *A61B 2017/2936* (2013.01); *A61B 2017/2946* (2013.01); *A61B 2090/031* (2016.02); *A61B 2090/0808* (2016.02); *A61B 2090/0811* (2016.02); *A61B 2090/08021* (2016.02)

(58) Field of Classification Search
CPC .. A61B 2017/00473; A61B 2017/2927; A61B 2017/2929; A61B 2017/2931; A61B 2017/2936; A61B 2017/2946; A61B 2090/031; A61B 2090/0808; A61B 2090/0811
USPC .................................. 606/51, 205; 600/106
See application file for complete search history.

(56) References Cited

U.S. PATENT DOCUMENTS

| | | | |
|---|---|---|---|
| 5,336,238 | A | 8/1994 | Holmes et al. |
| 5,352,219 | A | 10/1994 | Reddy |
| 5,368,606 | A | 11/1994 | Marlow et al. |
| 5,441,059 | A | 8/1995 | Dannan |
| 5,593,402 | A | 1/1997 | Patrick |
| 5,618,303 | A | 4/1997 | Marlow et al. |
| 5,782,748 | A | 7/1998 | Palmer et al. |
| 5,792,165 | A | 8/1998 | Klieman et al. |
| 5,893,875 | A | 4/1999 | O'Connor et al. |
| 6,074,408 | A | 6/2000 | Freeman |
| 6,309,397 | B1 | 10/2001 | Julian et al. |
| 6,558,318 | B1 | 5/2003 | Daniel et al. |
| 6,607,475 | B2 | 8/2003 | Doyle et al. |
| 6,723,043 | B2 | 4/2004 | Kleeman et al. |
| 6,916,314 | B2 | 7/2005 | Schneider et al. |
| 7,122,028 | B2 | 10/2006 | Looper et al. |
| 7,241,290 | B2 | 7/2007 | Doyle et al. |
| 7,429,259 | B2 | 9/2008 | Cadeddu et al. |
| 7,699,835 | B2 | 4/2010 | Lee et al. |
| 7,862,553 | B2 | 1/2011 | Ewaschuk |
| 2003/0060687 | A1 | 3/2003 | Kleeman et al. |
| 2003/0130693 | A1 | 7/2003 | Levin et al. |
| 2005/0165449 | A1 | 7/2005 | Cadeddu et al. |
| 2008/0015552 | A1 | 1/2008 | Doyle et al. |
| 2008/0243106 | A1 | 10/2008 | Coe et al. |
| 2008/0287926 | A1 | 11/2008 | Abou El Kheir |
| 2010/0249700 | A1 | 9/2010 | Spivey |
| 2010/0298774 | A1 | 11/2010 | Igov |
| 2011/0087265 | A1 | 4/2011 | Nobis et al. |
| 2011/0087266 | A1 | 4/2011 | Conlon et al. |
| 2011/0208007 | A1 | 8/2011 | Shohat et al. |
| 2012/0083826 | A1 | 4/2012 | Chao |

\* cited by examiner

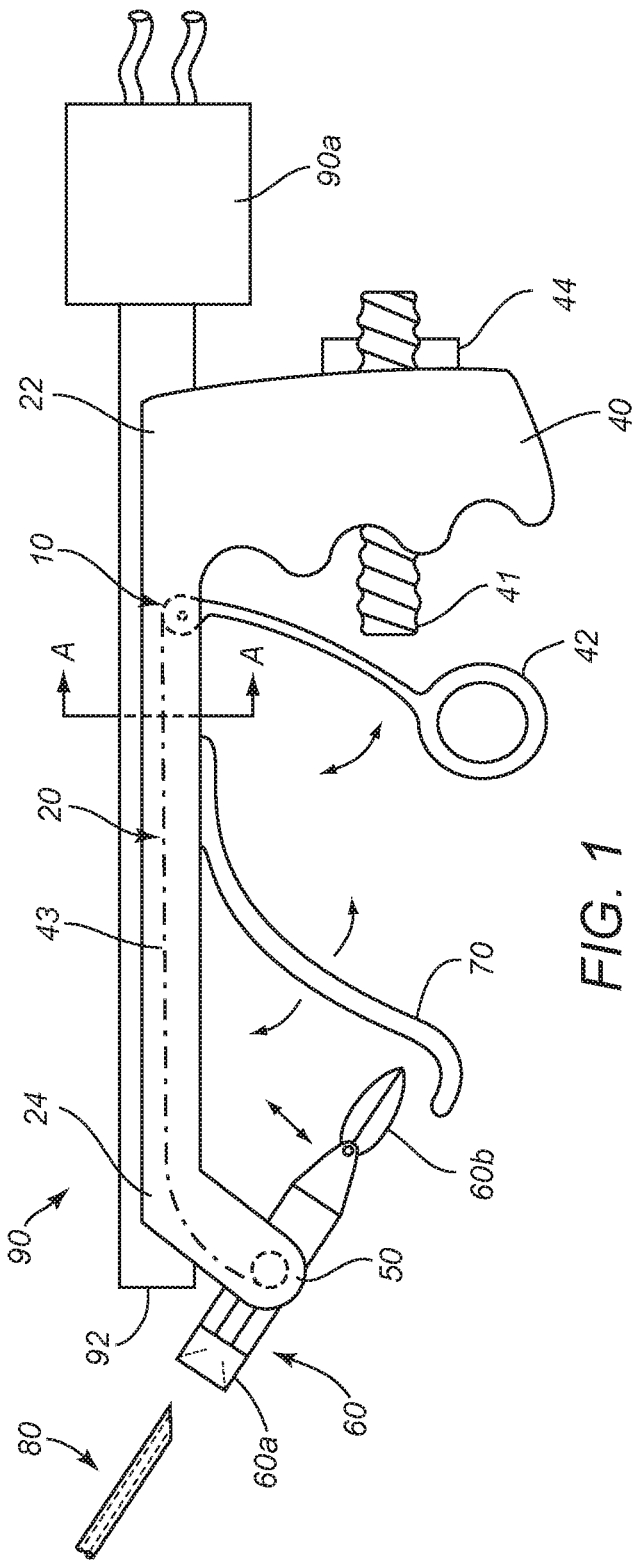
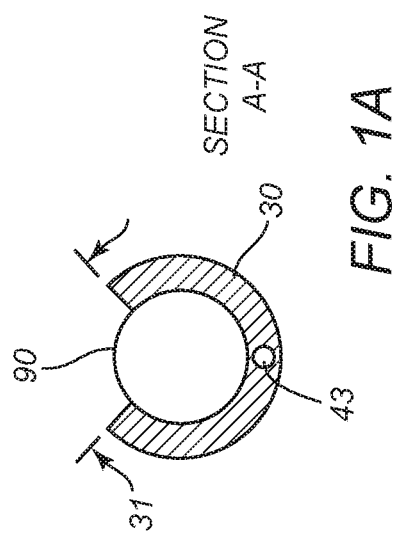
FIG. 1
FIG. 1A
SECTION A-A

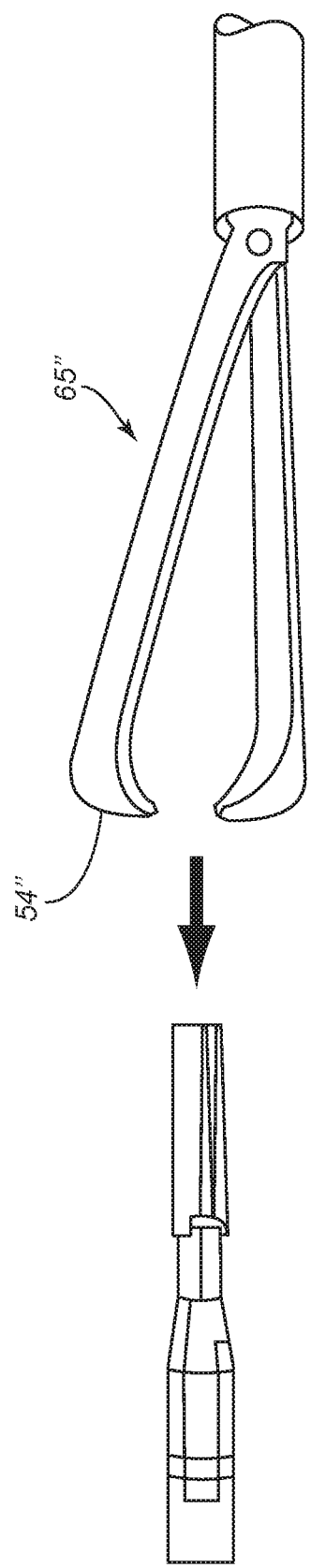
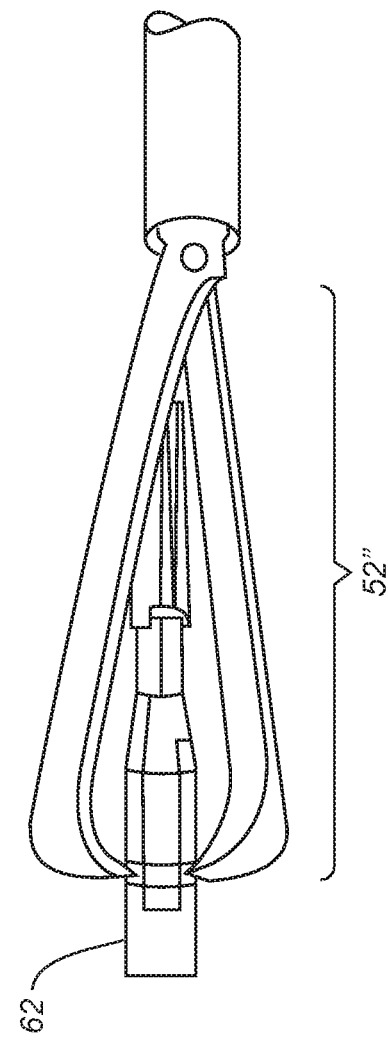
FIG. 3A
FIG. 3B

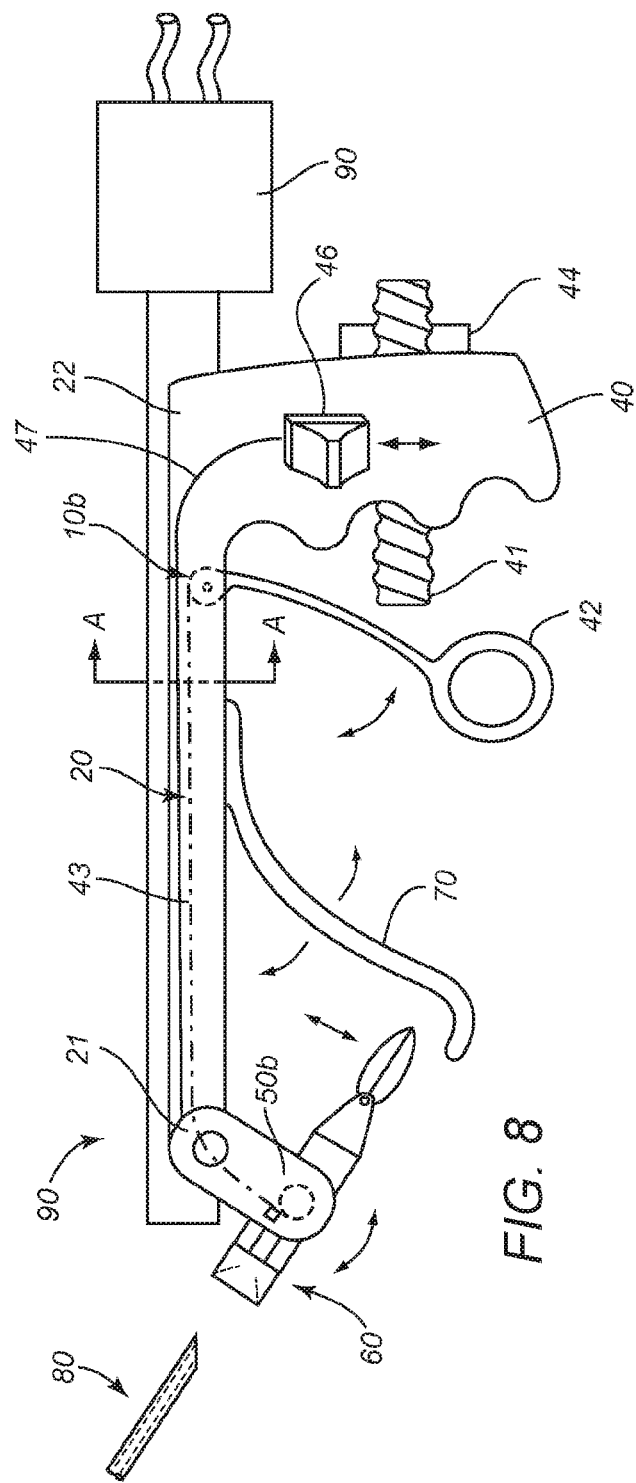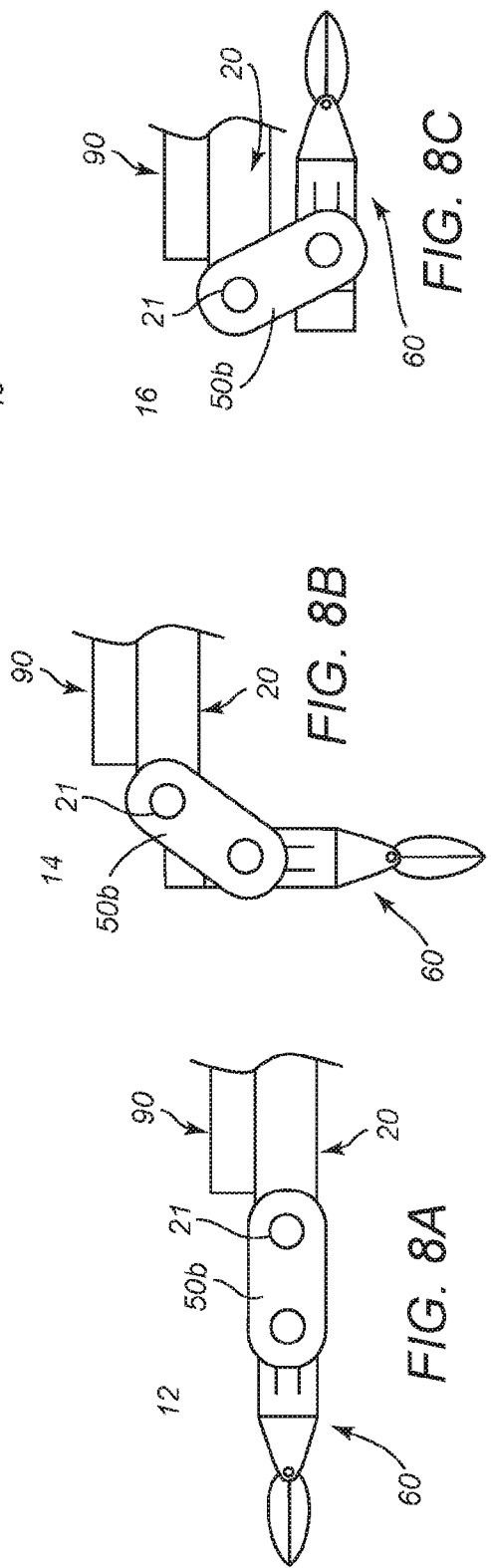

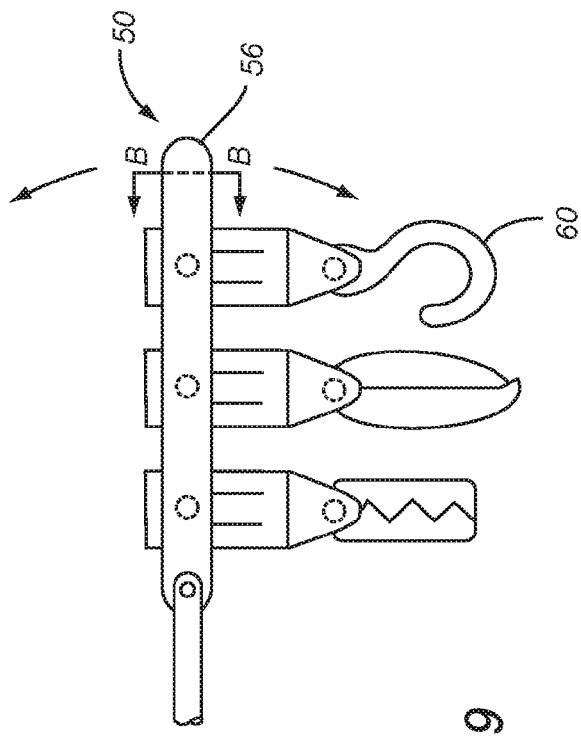
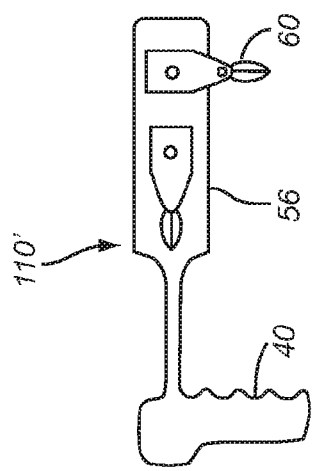
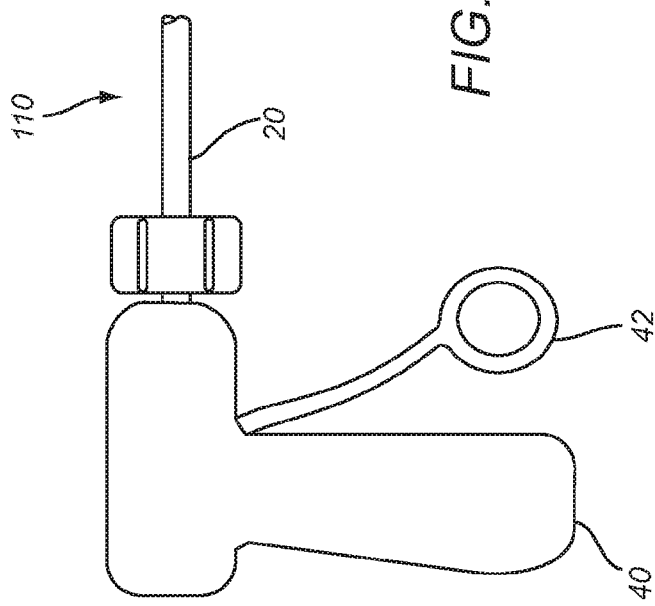
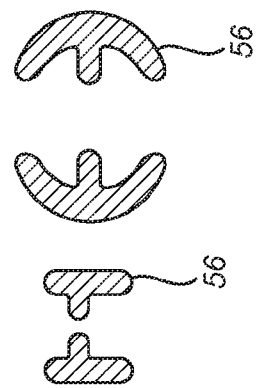
FIG. 9
FIG. 9B
FIG. 9A
SEC. B-B

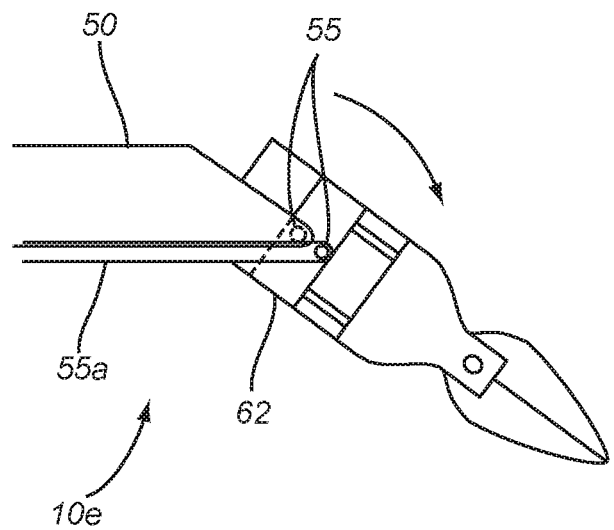
FIG. 19A
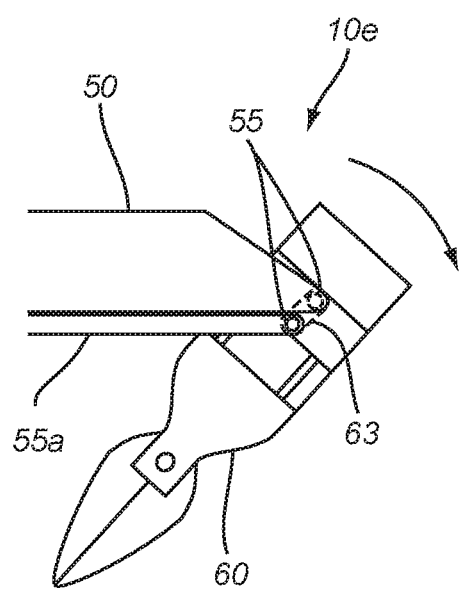
FIG. 19B

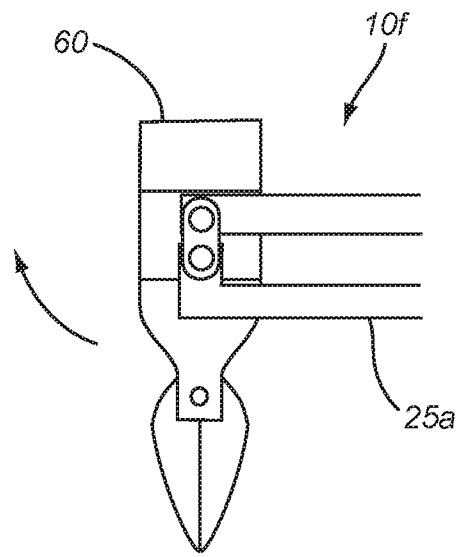
FIG. 20A
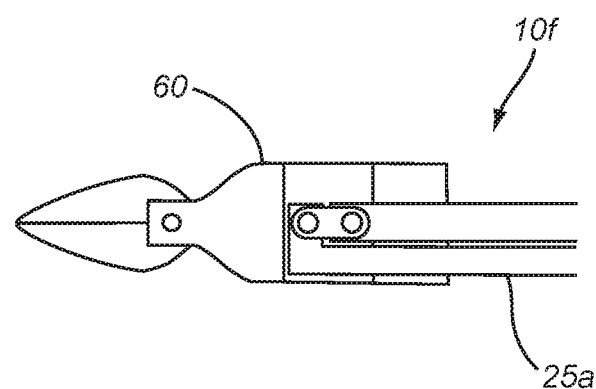
FIG. 20B

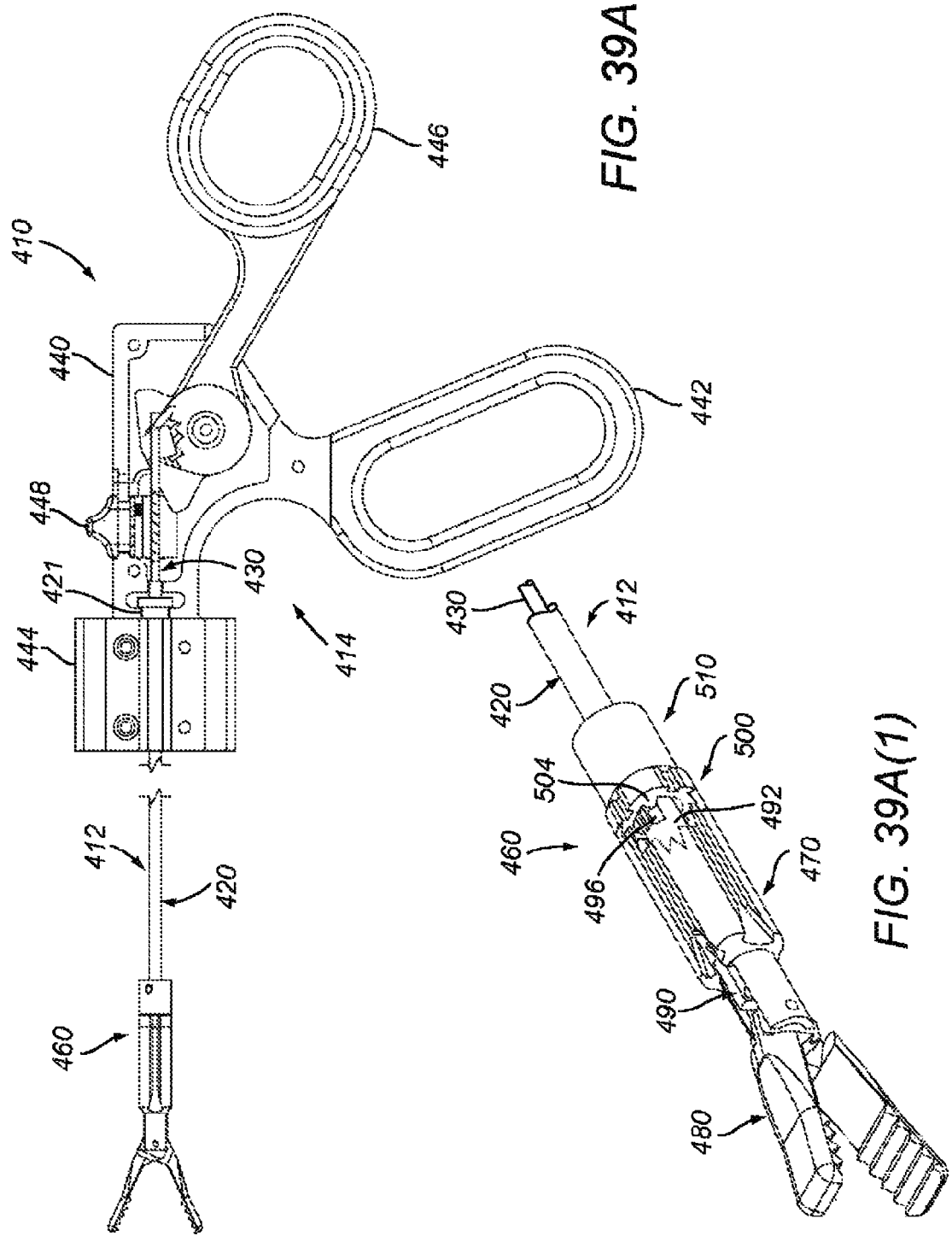

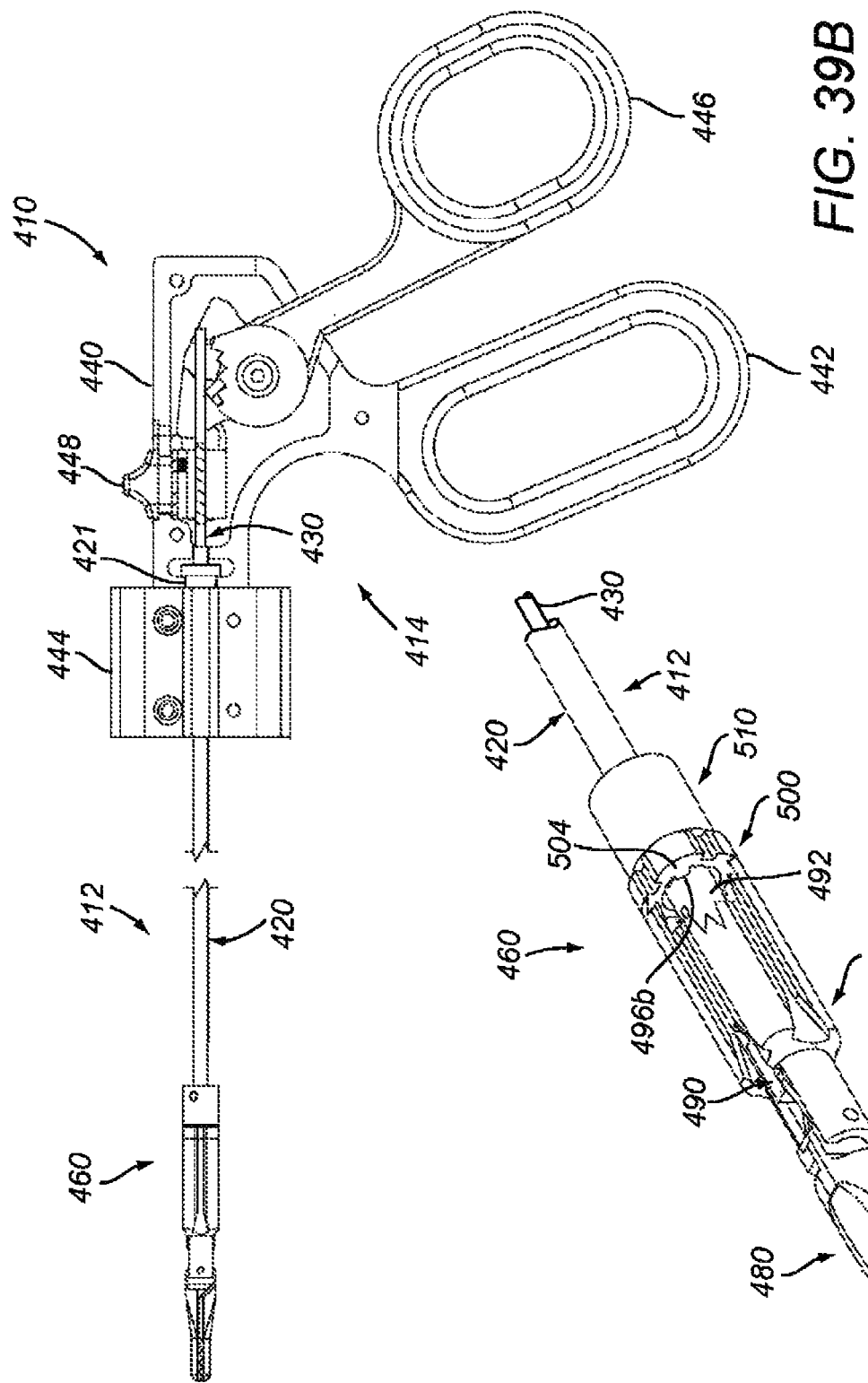

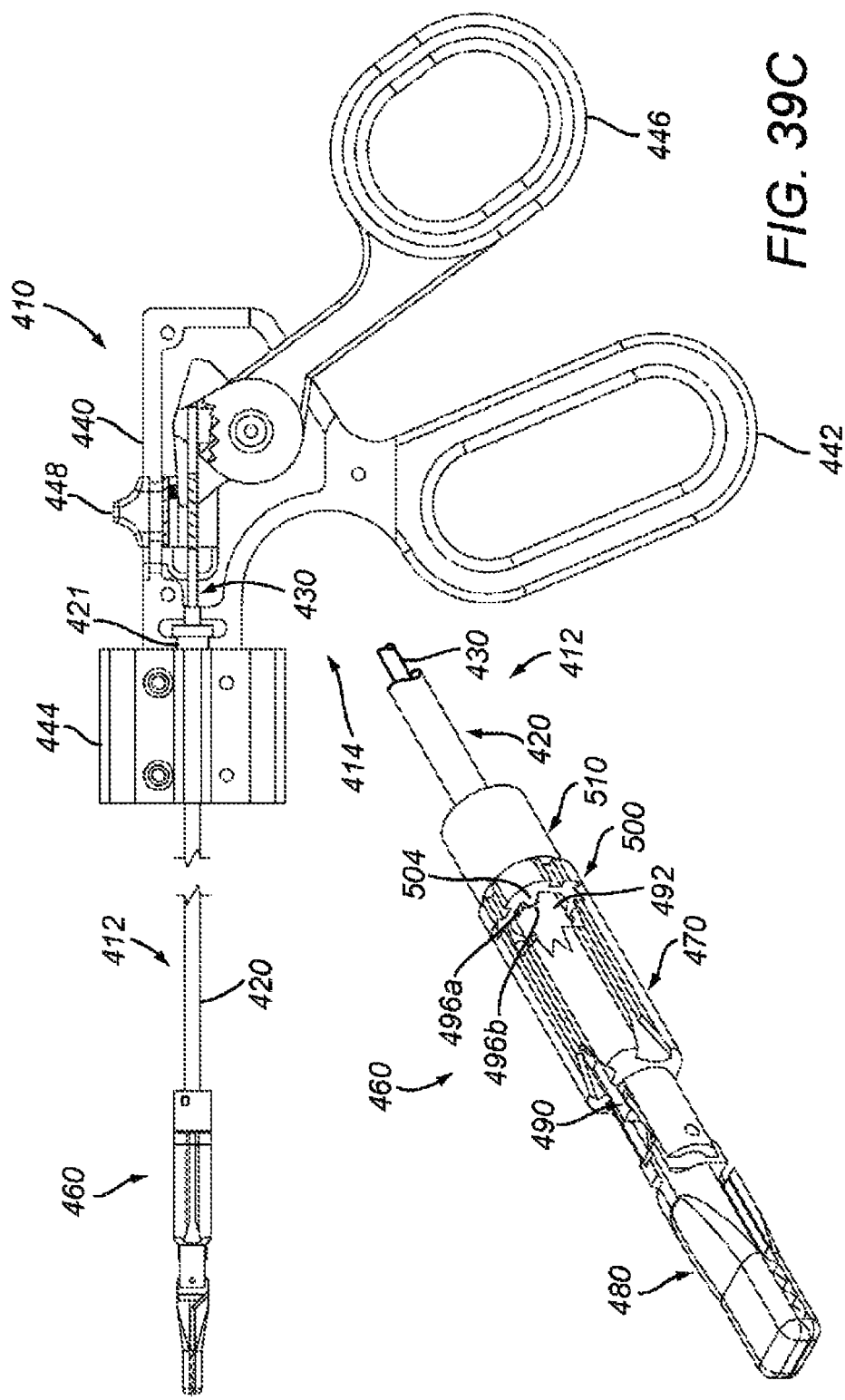

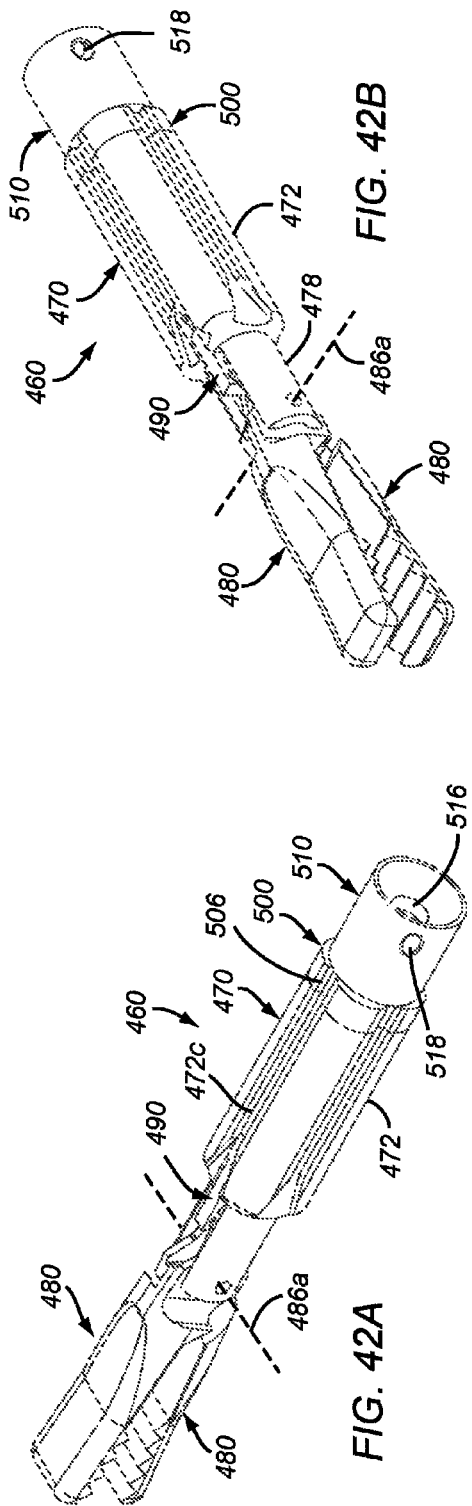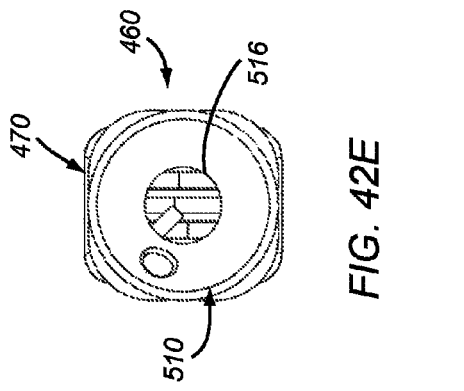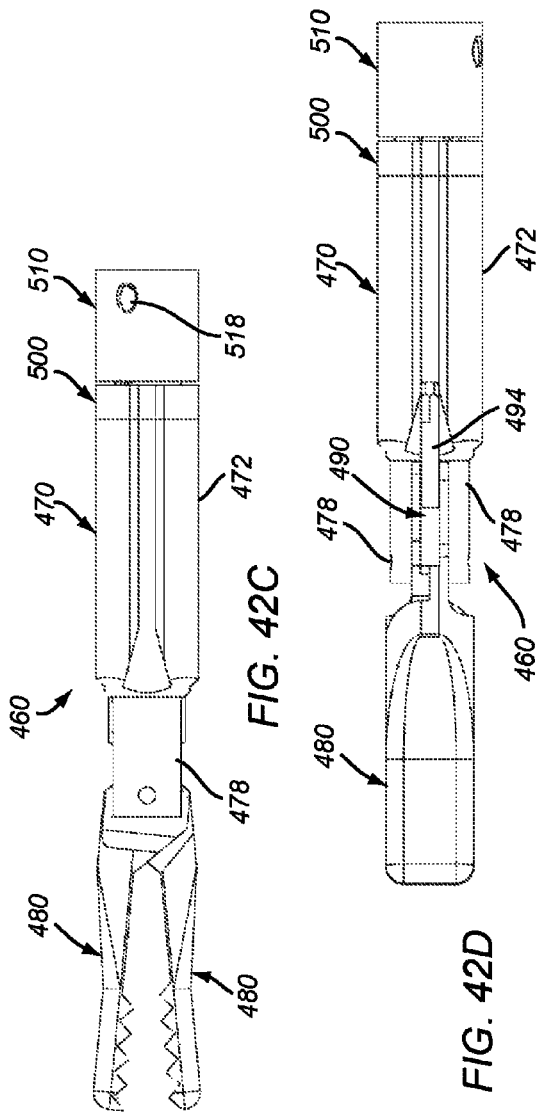

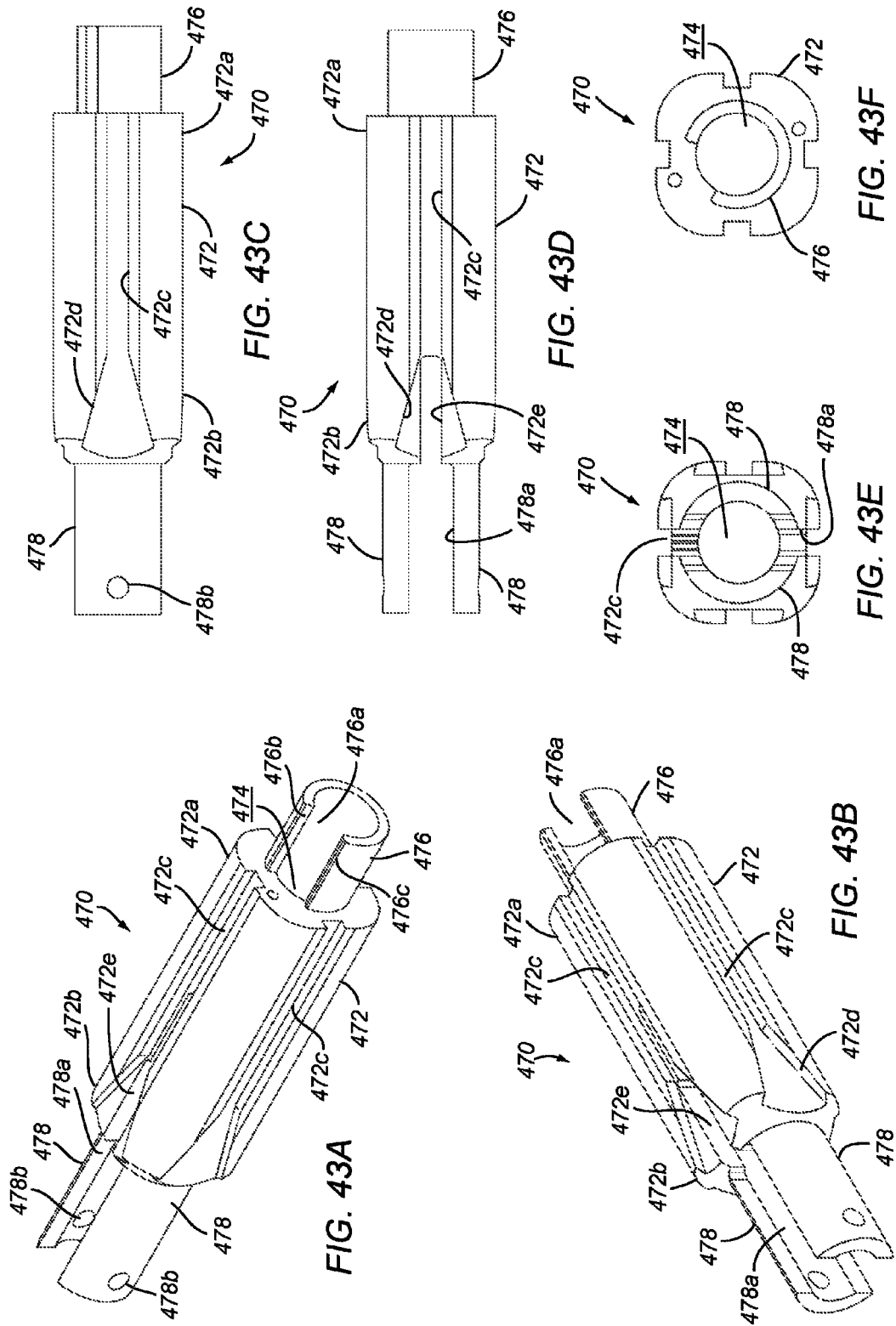

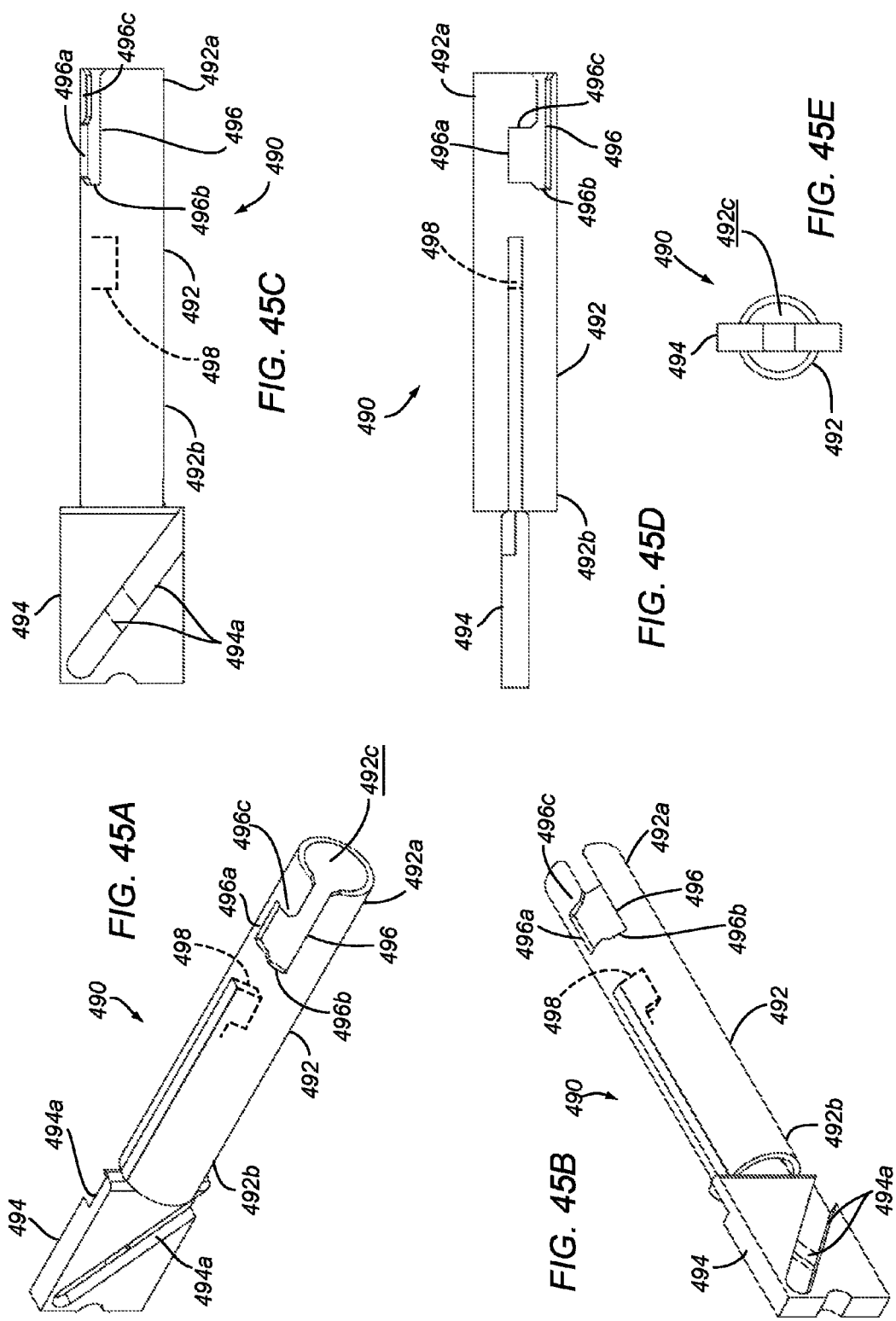

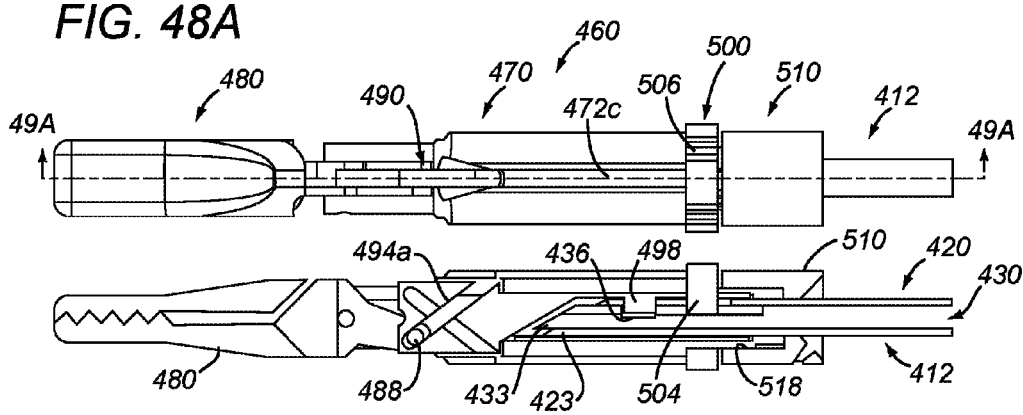
FIG. 48A
FIG. 49A
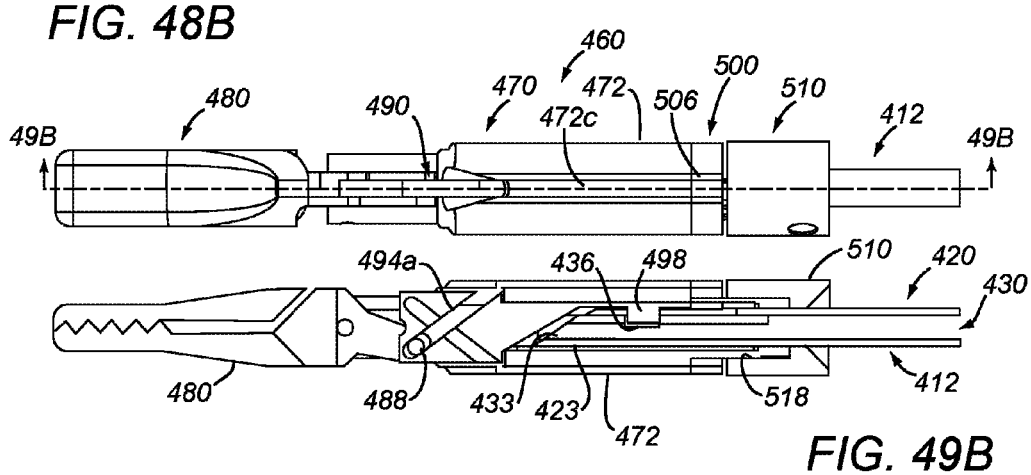
FIG. 48B
FIG. 49B
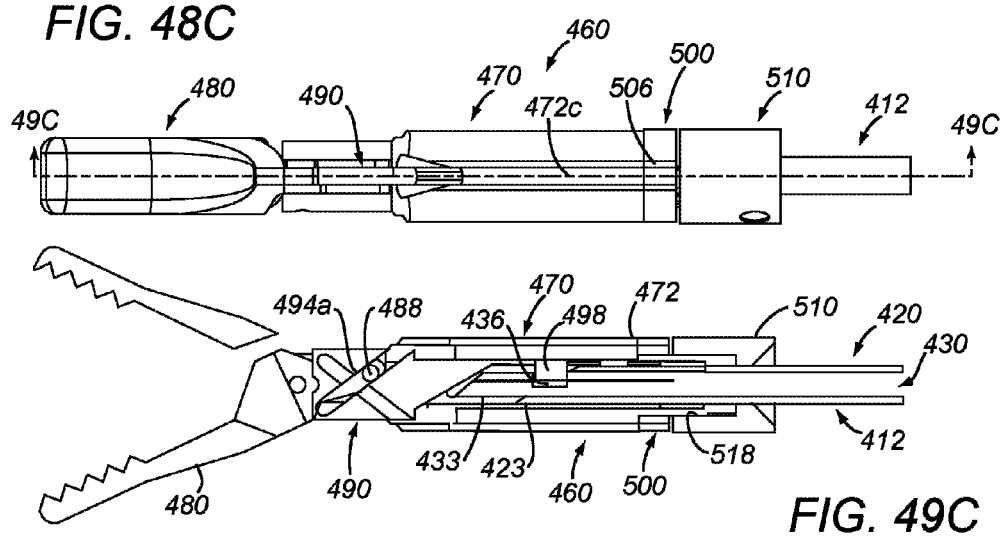
FIG. 48C
FIG. 49C

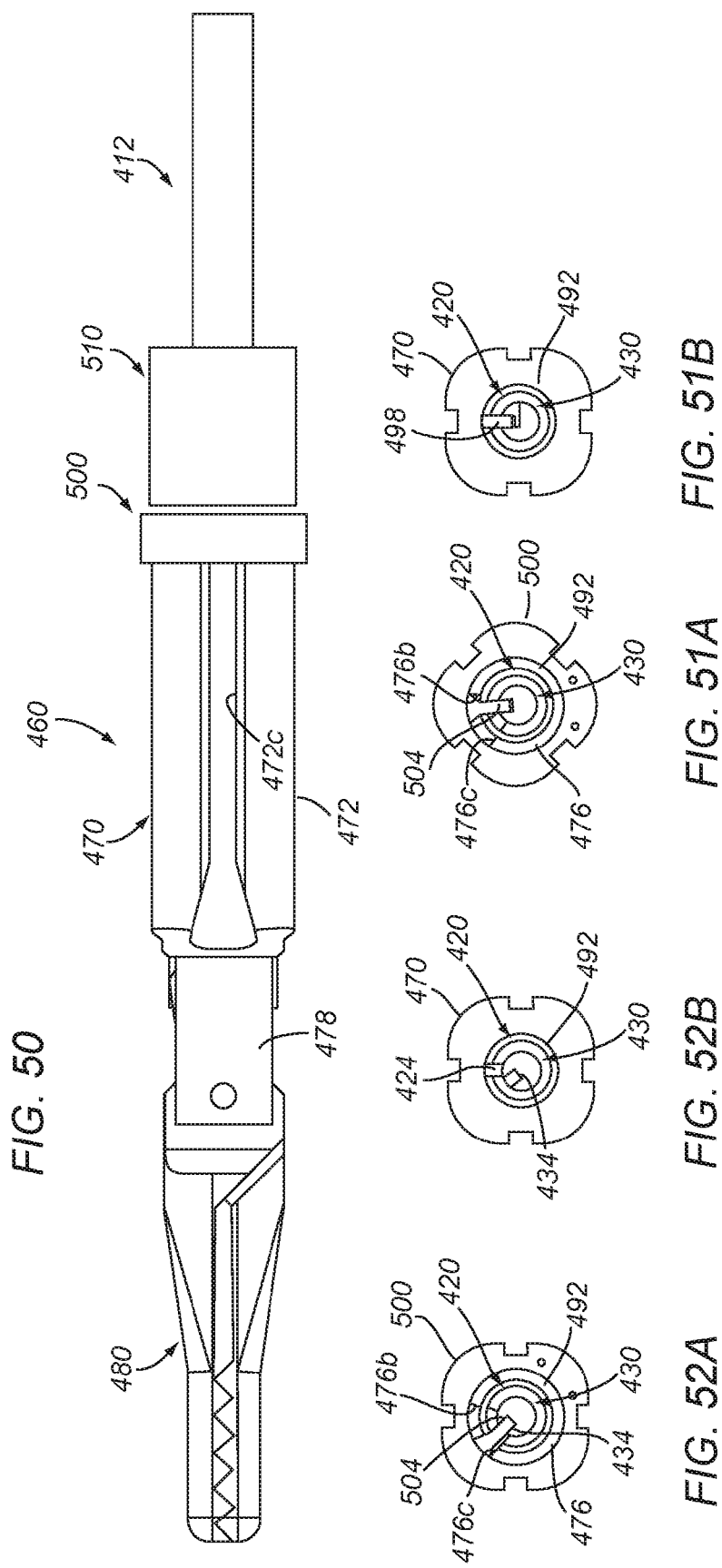

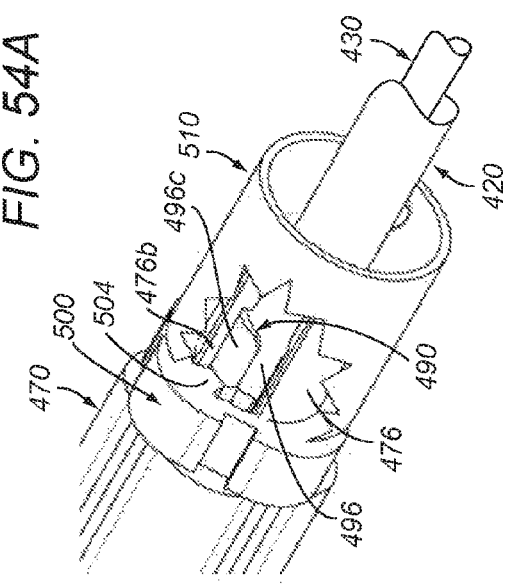
FIG. 54A
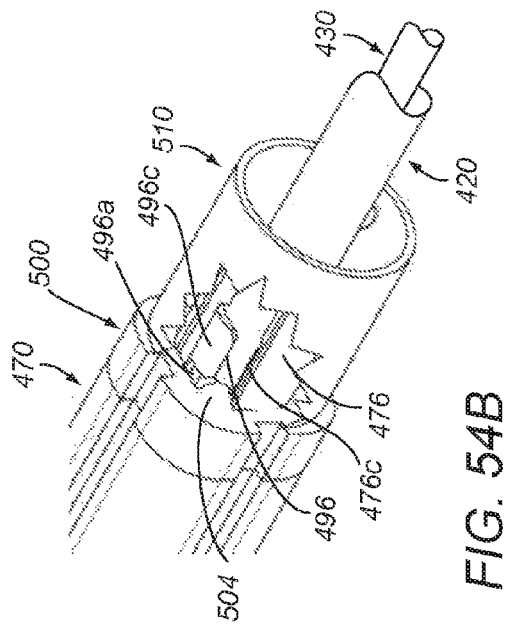
FIG. 54B
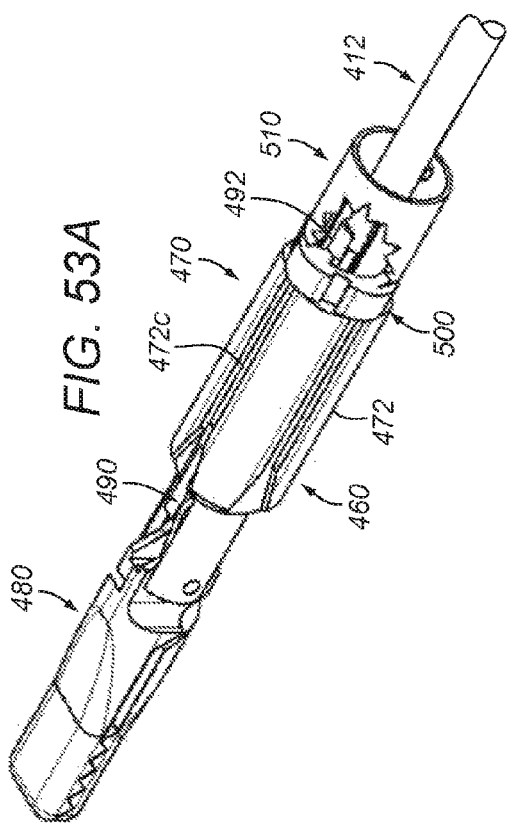
FIG. 53A
FIG. 53B

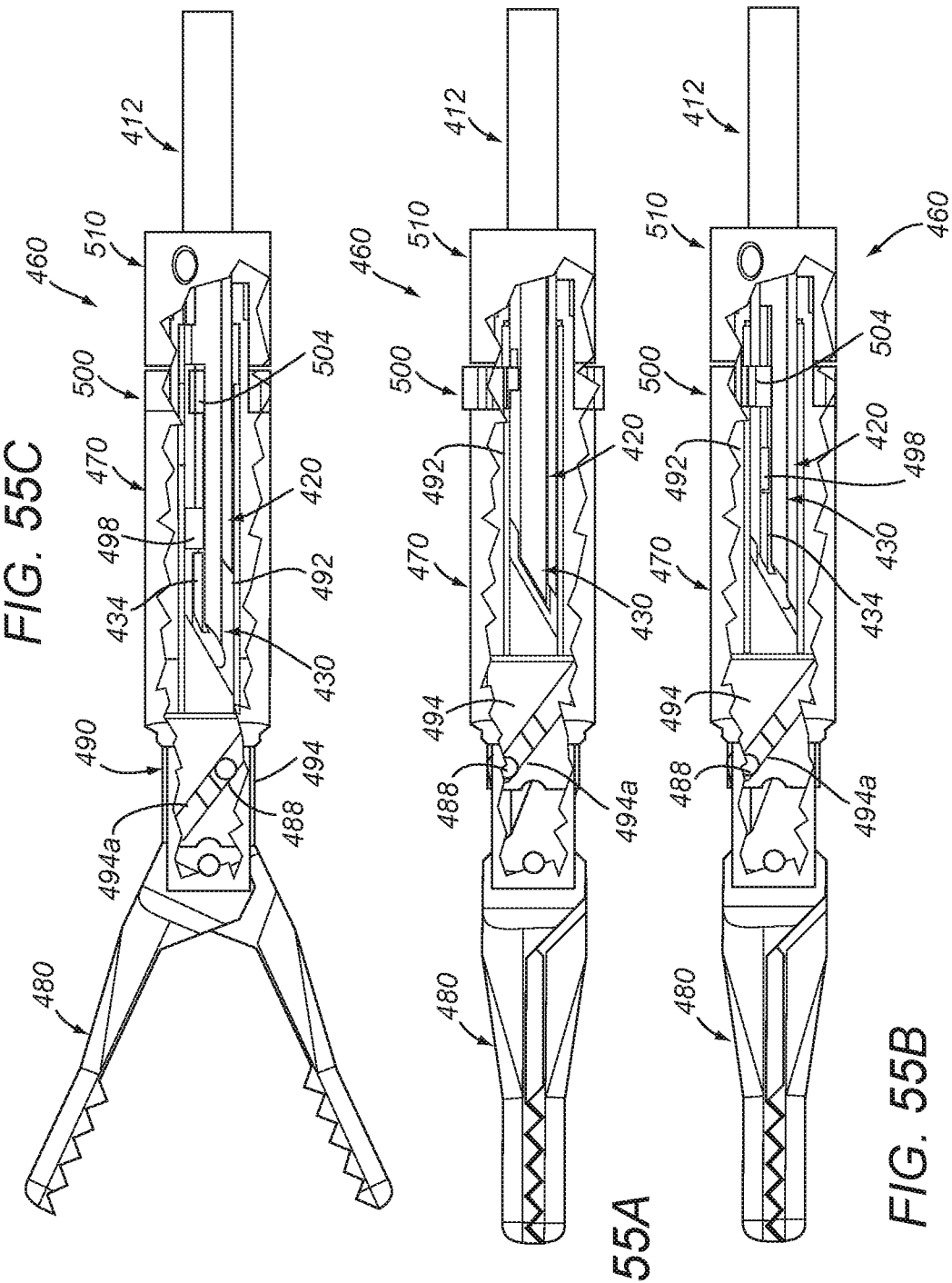

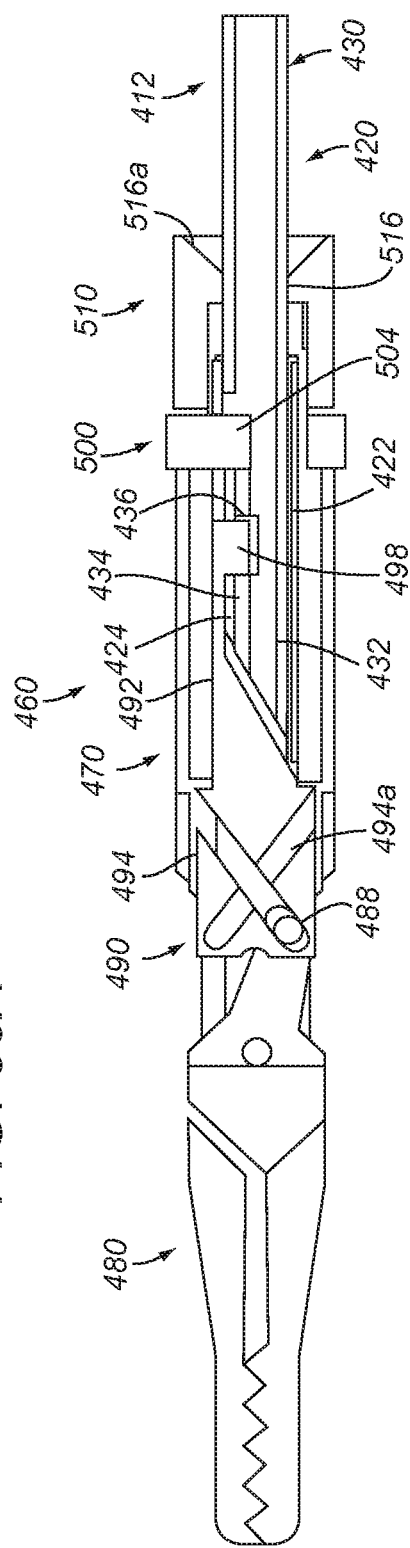
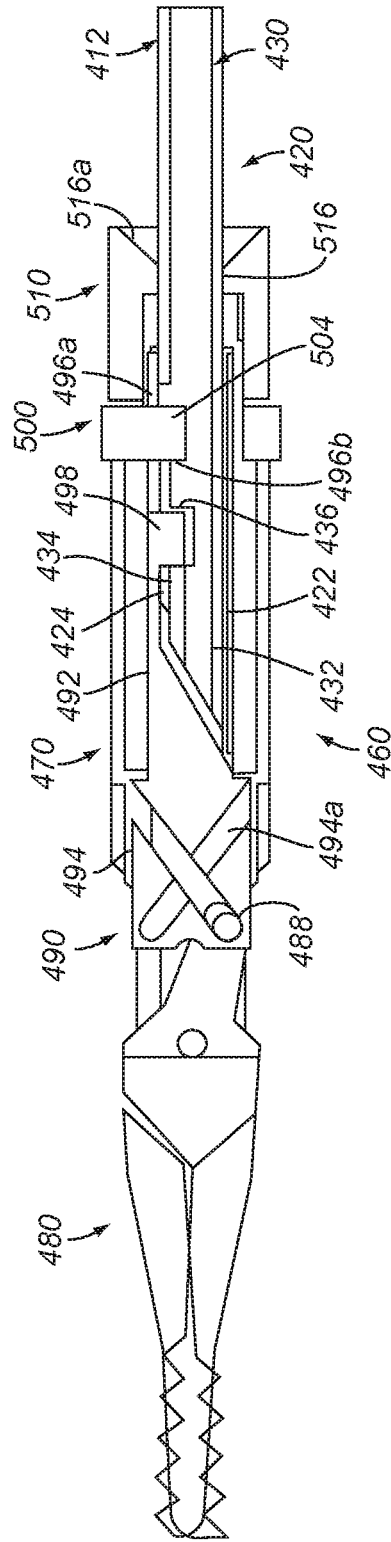

APPARATUS, SYSTEMS, AND METHODS FOR PERFORMING LAPAROSCOPIC SURGERY

RELATED APPLICATION DATA

This application is a continuation of co-pending International Application No. PCT/US2012/025136, filed Feb. 14, 2012, which claims benefit of U.S. provisional application Ser. No. 61/442,788, filed Feb. 14, 2011, the entire disclosures of which are expressly incorporated by reference herein. This application is also related to U.S. provisional application Ser. No. 61/314,595, filed Mar. 17, 2010, and international application no. PCT/US2010/001036, filed Apr. 5, 2010, published as International Publication No. WO 2010/114634, the entire disclosures of which are expressly incorporated by reference herein.

FIELD OF THE INVENTION

The present invention relates generally to apparatus, systems, and methods for performing surgery, e.g., laparoscopic surgery, and more particularly, to laparoscopic surgical tools and to systems and methods including such tools.

BACKGROUND

Surgery has become increasingly less invasive thanks to advances in medical technology. Laparoscopy is the dominant minimally invasive surgical (MIS) approach used today and has replaced many traditional "open" approaches. In laparoscopic surgery, trocars (typically 3-5) are placed at separate points in the surgical field. These trocars serve as ports into a body cavity or other surgical space (such as the abdomen) through which special long and thin instruments can be inserted. Manipulation of these tools from outside the body mechanically translates into motion within the body cavity. Depending on the tool head design, different instruments have different functions. The appropriate instrument is selected based on what the surgeon needs for that step of the procedure.

Minimally Invasive Surgery (MIS) offers several advantages compared to open surgical procedures including minimal trauma to the abdominal wall and hence less postoperative pain, fewer wound complications, earlier patient mobilization, and shorter length of stay. Laparoscopic access to the peritoneal space is the dominant MIS approach when performing minimally invasive abdominal operations.

Recent clinical studies show that further reduction of the size and/or number of incisions may offer added benefits such as faster recovery, less pain, reduced operative time, and improved cosmetic result. Such benefits may have physical and psychological impact.

However, the size of the tool tips on conventional instruments used in laparoscopic procedures generally limit the ability to reduce the size of the incisions and trocars needed for such procedures.

Recent waves of scar-free techniques, including natural orifice trans-luminal endoscopic surgery ("NOTES") and single-port surgery, have emerged to meet the need to further reduce the incisions required for surgical procedures. Ample information explaining the details of these new approaches exists in the public domain. Of the two, single-port surgery is thought among the surgery community to be the more feasible approach given available technology today.

Single-port surgery involves a multi-channel port that is typically placed in the belly button. This results in hidden scar post operatively. Through these channels, standard laparoscopic tools can be inserted. However, manipulation is more challenging because the tight aperture of the belly button and strong connective tissue in the abdominal wall forces all the instruments to move dependent on one another. In addition, the surgeon's hands are crowded together because of these constraints. Triangulation is largely lost. This makes the procedure frustrating to perform compared to other approaches.

A number of commercially available tools have been designed to circumvent some of these limitations. Some are variations of standard laparoscopic instruments but have articulating tool heads. Such designs are intended for re-enabling triangulation. However, constraints of the belly button port may force these articulating tools to cross, thus reversing the left-right motion between what the surgeon does with his hands and what he sees on the video monitor. Also, the complex mechanics behind the articulation may drive the cost up significantly.

The need exists for a revised laparoscopic technique and tools that reduce surgery-induced trauma but preserve the ergonomics and visualization to which surgeons have become accustomed. Such a procedure and tools may be safer for patients. A scar-free or minimal scar result may also appeal more to young adults, and the potential health benefits of a less traumatic approach may be higher for children and the elderly.

The first step during a laparoscopic surgical procedure is to insufflate the body cavity with a harmless gas (such as carbon dioxide) to increase the working space for the tools. The trocars are inserted across the abdominal wall and are designed to prevent excessive leakage of the insufflation gas, which invariably happens with incisions greater than three millimeters (3 mm).

In endoscopic and laparoscopic surgical procedures, a trocar device is used to puncture the patient's body in order to provide an access port through the abdominal wall to allow for the introduction of surgical instruments. A typical trocar requires a one-centimeter incision. Typically, a first trocar is placed above the umbilicus to introduce a camera to allow the surgeons to view the surgical site. The camera view is projected on a screen outside the body, which the surgeon and his or her assistants watch in order to appropriately manipulate the instruments inside the body cavity. Additional trocars are used to introduce surgical instruments, such as grasping tools, scissors, clips, and electrosurgical instruments. Typically, the laparoscopic instruments extend toward the surgical target from either side of the video camera. This "triangulation" of the instruments provides the most ergonomic and intuitive set up for the surgeon.

Patients who undergo laparoscopic surgery may benefit from shorter hospital stays and reduced surgery-inflicted morbidity compared to those who undergo open surgery. But, the number of trocar ports used in an operation is trauma-limited. For many cases, surgeries requiring more than five to seven (5-7) ports may be better performed using an open approach. Surgeons often hesitate to place more ports, even if it would mean making the procedure easier to do, because of the increased risk of wound complications with each additional incision (such as infection, dehiscence, or hernia).

SUMMARY OF THE INVENTION

The present invention is directed to apparatus, systems, and methods for performing surgery, e.g., laparoscopic surgery. More particularly, the present invention is directed to laparoscopic surgical tools and to systems and methods including such tools, e.g., designed to facilitate surgery while minimizing the number and/or size of access sites used and/or minimizing visible scars.

For example, in one embodiment, a modular surgical instrument may be provided that enables standard laparoscopic techniques to be performed through relatively small puncture holes in the body wall of a patient used to access the surgical space. In an exemplary embodiment, the assembled modular instrument may include a handle, a relatively small diameter control shaft (e.g., less than or equal to about 2.5 millimeter diameter), and one or more interchangeable tool heads. The control shaft may include two coaxial shafts, e.g., an outer cannular shaft and an inner "active" shaft, that move relative to one another, e.g., to actuate a tool head attached to the shaft in situ.

The tool head may be introduced into the surgical site independently of the control shaft, e.g., through separate trocar ports, punctures, or other access passages, e.g., located through the umbilicus and the like. The control shaft may be attached to the tool head within the surgical space inside the body. Once the modular instrument is fully assembled, the tool head may be manipulated through the puncture hole, e.g., using an actuator on the handle, to perform one or more procedures within the surgical space.

In an exemplary embodiment, a coaxial locking mechanism is provided between the control shaft and the tool head, e.g., that locks both an outer cannular shaft and the inner "active" shaft on the control shaft with respective elements on the tool head, e.g., as disclosed in International Publication No. WO 2010/114634, incorporated by reference herein.

In accordance with another embodiment, a surgical tool transfer system is provided that includes a tool head; an introduction tool comprising a distal end sized to be introduced into a surgical space; and a surgical tool comprising a control shaft including a distal end sized to be introduced into a surgical space independently of the introduction tool distal end, and comprising a first actuator for coupling the tool head to the control shaft distal end. The tool head may be configured to be coupled to the introduction tool distal end in a first static position and receive the control shaft distal end therein in the first position, whereupon the first actuator may be activated to rotate a portion of the tool head relative to the introduction tool distal end, thereby directing the tool head to a second active position releasing the tool head from the introduction tool distal end.

Optionally, the surgical tool comprises a second actuator, the second actuator coupled to an end effector of the tool head after the first actuator directs the tool head to the second active position, whereupon the second actuator may be activated to operate the end effector. The end effector may be locked with the tool head in the first static position. In an exemplary embodiment, the end effector may include a pair of jaws and the second actuator may be configured for directing the jaws between open and closed positions with the tool head in the second active position, and wherein the jaws may be locked, e.g., in the closed position, with the tool head in the first static position.

In accordance with still another embodiment, a system is provided for performing a procedure within a surgical space within a patient's body that includes a surgical tool including an elongate control shaft including a distal end sized for introduction into a surgical space, and a handle on a distal end; and a tool head connectable to the control shaft distal end. For example, the tool head may include a housing including proximal end for receiving the control shaft distal end therein, and a distal end. An end effector may be movably mounted to the housing distal end, an actuating link may be movable relative to the housing and coupled to the end effector for directing the end effector between first and second positions. The tool head may include a locking element rotatably mounted on the housing, the locking element coupled to the actuator link in the first position for preventing substantial movement of the actuator link and end effector.

The locking element and control shaft distal end may include cooperating connectors, and the surgical tool may include first and second actuators, the first actuator connectable to the locking element for rotating the locking element between a first orientation where the cooperating connectors are disconnected and control shaft distal end is removable from the housing proximal end, and a second orientation where the cooperating connectors substantially fix the control shaft distal end relative to the housing and couple the second actuator to the actuating link while releasing the actuating link from the locking element, the second actuator activatable for directing the actuator link to direct the end effector between the first and second positions.

In accordance with yet another embodiment, a modular tool head is provided for performing a procedure within a surgical space within a patient's body when the tool head is connected to a surgical tool including a control shaft including a distal end sized for introduction into the surgical space. The tool head may include a housing including a proximal end sized for receiving the distal end of the control shaft therein, a distal end, and a pair of opposing end effector elements pivotably coupled to the distal end, and an actuator link movable relative to the housing and coupled to the end effector elements for directing the end effector between open and closed positions. A locking element may be rotatable on the housing and coupled to the actuator link in the first position for preventing substantial movement of the actuator link and end effector elements.

In addition, the locking element may include connectors for engaging one or both of the distal ends of the inner and outer shafts, the locking element rotatable between first and second orientations on the housing, wherein, in the first orientation, the connectors are disconnected from the control shaft distal end such that the control shaft is removable from the housing proximal end and, in the second orientation, the connectors substantially fix the control shaft distal end relative to the housing and couple an actuator on surgical tool to the actuating link while releasing the actuating link from the locking element, the actuator activatable for directing the actuator link to direct the end effector elements between the open and closed positions.

In accordance with yet another embodiment, an apparatus is provided for delivering a tool head into a surgical space within a patient's body being visualized by an endoscope introduced into the surgical space via an access port. Generally, the apparatus includes an elongate shaft including a proximal end and a distal end, the shaft connectable to a shaft of an endoscope such that the shaft is advanceable from a proximal position to a distal position, e.g., such that the distal end is within a field of view of the endoscope. An end effector may be provided on the distal end for releasably engaging a tool head, and a handle may be provided on the proximal end of the shaft including an actuator for operating the end effector to engage and release a tool head.

In accordance with still another embodiment, a system or kit is provided for performing a procedure within a surgical space within a patient's body that includes a plurality of tool heads, and a tool head carrier including features for removably receiving one or more tool heads, the tool head carrier sized for introduction through a trocar or other port into a surgical space. The system or kit may also include a tool shaft introduceable into the surgical space and include features for securing a tool head to the tool. Each tool head may include a proximal end including a connector for coupling the tool head to a distal end of a tool shaft, and a distal end including an end effector for performing a surgical procedure.

Optionally, the tool head carrier may include a clip or other features for securing the tool head carrier to an endoscope and/or an endoscope. In addition, the system or kit may include one or more wires or rails, and a snare for capturing the wire or rail after being introduced into a surgical space. The wire may be attachable to a tool head carried by the tool carrier for guiding the tool head towards a tool shaft.

In accordance with still another embodiment, a system or kit is provided for performing a procedure within a surgical space within a patient's body that includes a plurality of tool heads, and a tool head carrier including a plurality of sockets, each socket including one or more features for removably receiving a respective tool head.

In accordance with yet another embodiment, a method is provided for performing a procedure within a surgical space within a patient's body that includes introducing a tool head into a surgical space through a trocar or other port, and securing the tool head to a tool shaft for performing a procedure within the surgical space. The tool head may be introduced into the surgical space on a tool head carrier, which may carry one or more tool heads, e.g., along an endoscope.

In accordance with still another embodiment, a method is provided for performing surgery within a surgical space within a patient's body that includes introducing a distal end of a wire into the surgical space adjacent a tool shaft via a first port; introducing a snare into the surgical space via a second port, and capturing the distal end of the wire with the snare. The snare is withdrawn to remove the distal end of the wire from the patient's body via the second port, and the distal end of the wire is coupled to a modular tool head. The tool head is introduced into the surgical space via the second port, the wire is manipulated to guide the tool head to a distal end of a tool shaft introduced into the surgical space via the first port, and the tool head is coupled to the distal end of the tool shaft.

Other aspects and features of the present invention will become apparent from consideration of the following description taken in conjunction with the accompanying drawings.

BRIEF DESCRIPTION OF THE DRAWINGS

It will be appreciated that the exemplary apparatus shown in the drawings are not necessarily drawn to scale, with emphasis instead being placed on illustrating the various aspects and features of the illustrated embodiments.

FIG. 1 is a side view of a first exemplary embodiment of a carrier tool coupled to an endoscope for introducing a tool head into a surgical space.

FIG. 1A is a cross-sectional view of the carrier tool of FIG. 1 taken along line A-A.

FIGS. 3A and 3B are side views of an alternative embodiment of a set of jaws that may be provided on the carrier tool of FIG. 2, showing a tool head being secured to the jaws.

FIG. 8 is a side view of yet another exemplary embodiment of a carrier tool coupled to an endoscope for introducing a tool head into a surgical space.

FIGS. 8A-8C are details of a distal end of the carrier tool of FIG. 8, showing the tool head being directed into different orientations by the carrier tool.

FIG. 9 is a side view of an exemplary embodiment of a carrier tool for introducing a plurality of tool heads into a surgical space.

FIG. 9A is a cross-section of a housing of the carrier tool of FIG. 9, taken along line B-B.

FIG. 9B is a side view of an alternative embodiment of a carrier tool for introducing a plurality of tool heads into a surgical space.

FIGS. 19A and 19B are details of a distal end of a tool carrier showing a mechanism on the tool carrier directing a tool head carried thereby between proximal and distal orientations, respectively.

FIGS. 20A and 20B are details of a distal end of a tool carrier showing another mechanism on the tool carrier directing a tool head carried thereby between transverse and substantially axial orientations, respectively.

FIGS. 23-29 show alternatively embodiments of introduction features that may be provided on the tool carrier of FIG. 22 or other tool carriers herein for carrying a tool head. For example, FIG. 23 shows an exemplary embodiment of an introduction ring that may be carried by a tube shaft.

FIG. 27 is a cross-sectional view of another embodiment of an introduction ring carried by an endoscope and engaged with corresponding features on a tool head.

28A and 28B are perspective views of another embodiment of an introduction ring including a biasing mechanism that biases the introduction ring to a desired orientation relative to a shaft of a carrier tool.

FIGS. 39A and 39B are side views of an exemplary embodiment of a surgical tool including a handle and control shaft with a modular tool head coupled to the shaft, showing an end effector of the tool head in open and fully closed positions, respectively.

FIG. 39C is a side view of the surgical tool of FIGS. 39A and 39B with an actuator on the handle directed to an alignment position (from the operational position shown in FIGS. 39A and 39B) in which the tool head may be coupled or removed from the shaft.

FIGS. 39A(1)-39C(1) are details of the tool head of FIGS. 39A-39C, respectively, showing relative alignment of internal features of the tool head and control shaft.

FIGS. 42A and 42B are perspective views of an exemplary embodiment of a tool head that may be coupled to the surgical tool of FIGS. 39A-39C. FIGS. 42C-42E are side, top, and end views, respectively, of the tool head of FIGS. 42A and 42B.

FIGS. 43A-43F show exemplary embodiments of components of the tool head of FIGS. 42A-42E. For example, FIGS. 43A and 43B are perspective views of an exemplary embodiment of a housing of the tool head. FIGS. 43C-43F are side, top, and distal and proximal end views, respectively, of the housing.

FIGS. 45A and 45B are perspective views of an exemplary embodiment of an actuating link that may be received within the housing and coupled to the end effector of the tool head. FIGS. 45C-45E are side, top, and end views of the actuating link.

FIGS. 48A-48C are top views of the tool head of FIGS. 42A-42E being coupled to a control shaft, such as that shown in FIGS. 40A-41B.

FIGS. 49A-49C are cross-sectional views of the tool head and control shaft shown in FIGS. 48A-48C, respectively.

FIG. 50 is a side view of the tool head and control shaft of FIGS. 48A-49C. FIGS. 51A and 51B are cross-sections taken at A-A and B-B, respectively, before the tool head is coupled to the control shaft (in the disengaged position). FIGS. 52A and 52B are cross-sections taken at A-A and B-B, respectively, after the tool head is coupled to the control shaft (in the engaged position).

FIGS. 53A-53C are perspective views of the tool head and control shaft with the end effector locked in a closed position before the tool head is coupled to the control shaft (FIG. 53A), with the end effector unlocked and in a closed position after the tool head is coupled to the control shaft (FIG. 53B), and with the end effector unlocked and in an open position (FIG. 53C).

FIGS. 54A-54C are perspective details of the FIGS. 53A-53C, respectively, showing the relative position of a locking tooth and pocket on the locking collar and actuating link in the different positions.

FIGS. 55A-55C are partial cross-sectional views of the tool head in the positions shown in FIGS. 53A-53C, respectively.

FIGS. 56A and 56B are cross-sectional details of the tool head and control shaft of FIGS. 53A-53C, showing the actuating link in an alignment position that enables disengaging the tool head from the control shaft (FIG. 56A) and an operational position with the end effector in a closed position (FIG. 56B).

Figure 2:
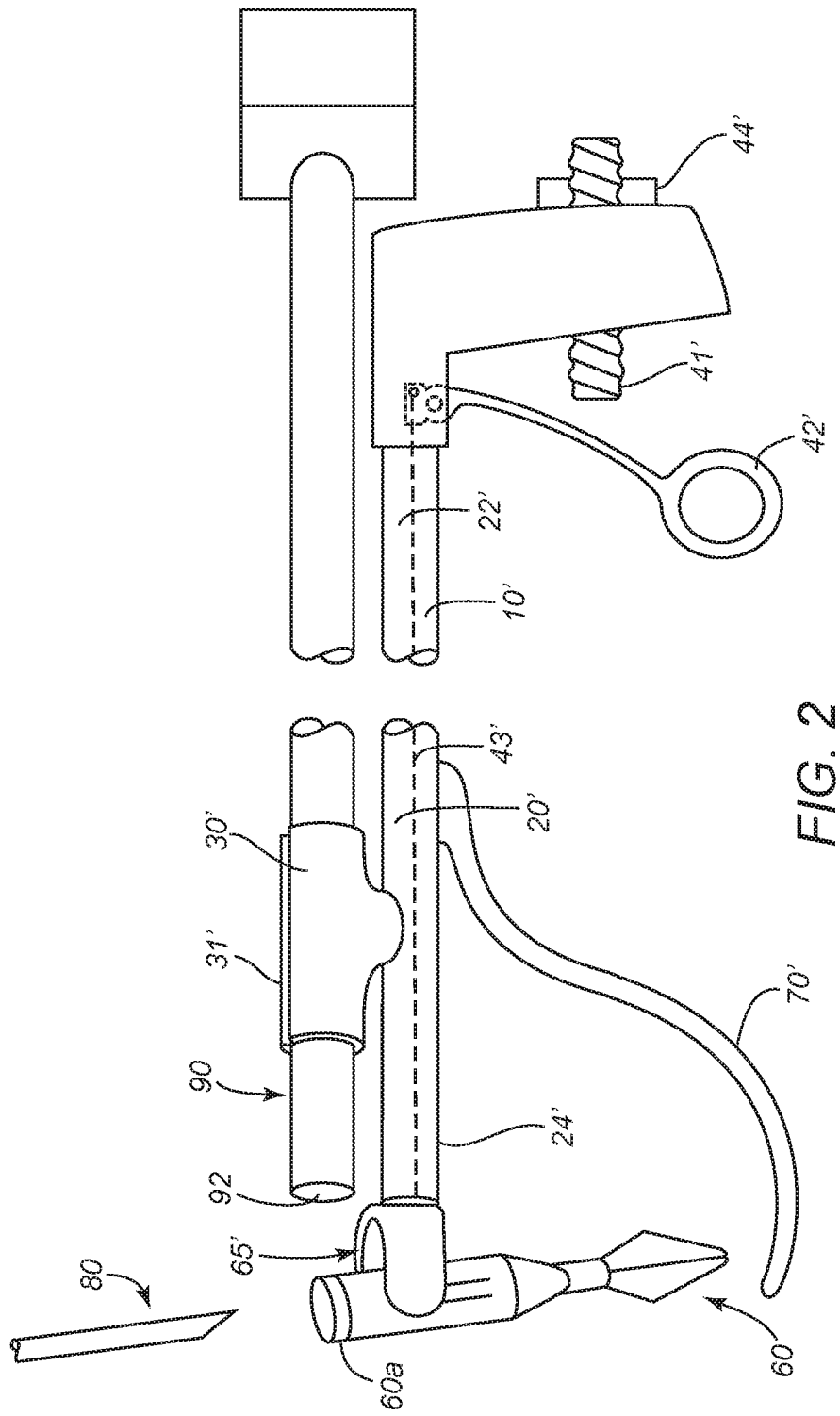
FIG. 2 is a side view of another exemplary embodiment of a carrier tool coupled to an endoscope for introducing a tool head into a surgical space.

DETAILED DESCRIPTION OF THE
EXEMPLARY EMBODIMENTS

Turning to the drawings, FIG. 1 shows an exemplary embodiment of an introduction apparatus 10 that includes an elongate shaft 20 including a proximal end 22 and a distal end 24, one or more clip elements 30 for slidably securing the shaft 20 to an endoscope 90, a handle 40 on the proximal end 22, and a housing 50 on the distal end 24 for releasably engaging a tool head 60. The handle 40 may include a trigger or other actuator 42, e.g., for operating the housing 50 to engage and/or release a tool head 60 with a connecting or actuating wire or rod 43.

As best seen in FIG. 1A, the shaft 20 includes a generally "U" or "C" shaped cross-section, e.g., having a periphery greater than one hundred eighty degrees (180°), thereby defining opposing clip elements 30 for securing the shaft 20 to the housing 50. The shaft 20 and/or clip elements 30 may be formed from substantially rigid or semi-rigid material, e.g., plastic, metal, or composite materials, having sufficient rigidity to maintain the position of the housing 50 relative to the shaft 20 and/or relative to a lens 92 of the endoscope 90. As shown, the clip elements 30 may extend substantially the entire distance between the proximal and distal ends 22, 24 of the shaft 20. Alternatively, the clip elements 30 may extend only partially between the proximal and distal ends 22, 24 or a plurality of clip elements 30 may be provided that are spaced apart from one another along a length of the shaft 20 (not shown).

The internal diameter of the clip elements 30 may be sized to mate closely with the outer diameter of the endoscope 90, while allowing the shaft 20 to be directed axially relative to the endoscope 90, if desired. Alternatively, the clip elements 30 may engage the endoscope 90 sufficiently to limit substantial axial movement of the shaft 20 relative to the endoscope 90, while allowing the shaft 20 to be removed from the endoscope 90, if desired, as described further below. The clip elements 30 may define a slit or a slot 31 therebetween, e.g., such that the shaft 20 may be loaded onto the endoscope 90 laterally from the side. For example, the material of the clip elements 30 and/or shaft 20 may be sufficiently elastic to temporarily deform to clip onto the endoscope 90, yet sufficiently rigid to maintain its shape and/or orientation relative to the endoscope 90.

The shaft 20 may have sufficient length such that the handle 40 is located adjacent a proximal housing 90a of the endoscope 90 while the housing 50 is disposed adjacent the lens 92, e.g., such that the handle 40 extends outside a patient's body while the lens 92 and housing 50 are located within a surgical space within the patient's body. The handle 40 allows the surgeon or other user to clip the entire apparatus 10 onto the endoscope 90, and/or advance the apparatus 10 relative to the endoscope 90, e.g., into the patient's body, and into the field of view of the lens 92 of the endoscope 90.

Optionally, the apparatus 10 may include a stop 41, e.g., within or otherwise coupled to the handle 40, that limits distal movement, e.g., when the apparatus 10 has been introduced to an appropriate depth relative to the endoscope 90. The stop length may be manually adjustable by the surgeon, e.g., with a thumbwheel or other actuator 44. In addition or alternatively, a stop may be provided on the endoscope (not shown) that may limit distal advancement of the apparatus 10 relative to the endoscope. In addition, the handle 40 may also allow the surgeon to remove the apparatus 40 at least partially from the surgical space relative to the endoscope 90.

The housing 50 is attached to or otherwise provided on the distal end 24 of the shaft 20. The housing 50 may be configured for one or more purposes, e.g., a) to lock the tool head 60 to the housing 50 until it is unlocked by the cannular tube or shaft 80, b) to orient the tool head 60, and/or c) to shroud the ends of the tool head 60, as described further below. Optionally, the shroud 70 may be provided on the shaft 20, e.g., on the distal end 24 or between the proximal and distal ends 22, 24, i.e., proximal to the housing 50, to shroud the tool head 60 with proximal and/or distal conical, curved, or otherwise tapered features, e.g., to facilitate insertion and/or removal of the tool head 60 carried by the apparatus 10 into and out of the patient's body.

The tool head 60 is locked into the housing 50 by an operator outside of the patient's body, e.g., by loading and rotating the tool head 60 relative to the housing 50. The orientation of the tool head 60 when fully captured within the housing 50 may be such that the proximal end 60a of the tool head 60 is in the field of view of the lens 92 of the endoscope 90 when the apparatus 10 is advanced to its distal position.

Turning to FIG. 2, an alternative embodiment of an introduction apparatus 10' is shown that includes a surgical jaw or forceps 65' on the distal end 24' instead of the housing 50.' Generally, the apparatus 10' includes an elongate shaft 20' including a proximal end 22' and a distal end 24,' one or more clip elements 30' for securing the shaft 20' to an endoscope 90, and a moveable handle 40' on the proximal end 22,' similar to the apparatus 10 of FIG. 1, but includes a surgical jaw 65' on the distal end 24' for releasably engaging a tool head 60 instead of the housing 50.' The handle 40' may include a trigger or other actuator 42,' e.g., for operating the surgical jaw 65' to engage and/or release the tool head 60. Optionally, the handle 40' may include a pin or other locking element (not shown) for releasably securing the trigger 42' in its closed and/or open position, e.g., to engage the tool head 60 without requiring the surgeon to continue to pull the trigger 42.'

Unlike the previous embodiment, the clip 30' includes a sleeve having a "U" or "C" shaped cross-section that is attached to the shaft 20.' Similar to the previous embodiment, the clip 30' may be resiliently expandable such that the sleeve may be applied laterally to the endoscope 90 to capture the endoscope 90 within the sleeve, thereby slidably or fixedly securing the shaft 20' relative to the endoscope 90. Also similar to the previous embodiment, the shaft 20' may be sufficiently rigid to maintain the position of the jaw 65' relative to the clip 30' and/or relative to the lens 92 of the endoscope 90.

For example, the internal diameter of the clip 30' may be sized to mate closely with the outer diameter of the endoscope lens 90. The clip 30' may define a slit or a slot 31' such that the sleeve of the clip 30' may be loaded onto the endoscope 90 from the side. The material of the clip 30' may be sufficiently elastic to temporarily deform to allow the sleeve to expand to receive the endoscope 90 therein and resilient such that sleeve closes around the endoscope 90. The material of the clip 30' may be sufficiently rigid to maintain its shape and/or orientation relative to the endoscope 90. Once received on the endoscope 90, the clip 30' may be slidable axially, e.g., to allow the shaft 20' to be directed between proximal and distal positions, similar to the previous embodiment. Alternatively, the clip 30' may engage the endoscope with sufficient frictional force such that there is minimal axial movement of the clip 30' relative to the endoscope 90. In this alternative, the shaft 20' may be movable axially and/or rotationally relative to the clip 30', e.g., between proximal and distal positions, to allow the surgical jaw 65' to be advanced into the field of view of the lens 92, as described further below.

The shaft 20' generally has sufficient length such that the handle 40' is located outside of the patient's body and next to the endoscope 90. The trigger 42' on the handle 40' may be activated to actuate the surgical jaw 65. The handle 40 may facilitate clipping the apparatus 10' onto the endoscope 90, advance the apparatus 10' into the patient's body and/or into the field of view of the endoscope 90, and/or remove the apparatus 10' from the patient's body. After the tool head 60 is in the field of view of the endoscope 90, the handle 40' may allow further manipulation of the position of the tool head 60, e.g., rotationally and/or axially relative to the field of view. Optionally, the apparatus 10' may include a stop 41,' e.g., within or otherwise provided on the handle 40,' the apparatus 10' encountering the stop when the apparatus 10' has been introduced to the appropriate depth relative to the endoscope 90. If desired, the length and/or position of the rigid stop 41' may be adjustable, e.g., by a thumbwheel or other actuator 44.'

The surgical jaw 65' may be attached to or otherwise provided on the distal end 24' of the shaft 20.' The surgical jaw or forceps 65' may be moveable, e.g., by actuation of the trigger 42' on the handle 40' from outside the patient's body, which may transmit corresponding motion from the trigger 42' to one or both jaws of the surgical jaw 64,' e.g., by axial motion of an actuating rod or wire 43.' Similar to the previous embodiment, a shroud 70' may be provided to at least partially cover the tool head 60 with proximal and/or distal conical, curved, or otherwise tapered features, e.g., to facilitate insertion into and/or removal from the patient's body. The surgical jaw 65' may provide one or more purposes, e.g., to lock the tool head 60 to the jaw 65' until it is unlocked by the control shaft 80, orient the tool head 60 such that the surgeon is able to see the appropriate end of the tool head 60 for assembly, and/or shroud the ends of the tool head 60. The jaw 65' may grip the tool head 60 in a predetermined orientation relative to the longitudinal axis of the shaft 20,' e.g., with substantially coaxial or perpendicular alignment.

The tool head 60 may be locked or otherwise secured into the surgical jaw 65' by an operator outside of the patient's body, e.g., by loading and rotating the tool head 60 relative to the jaw 65.' When secured within the jaw 65,' the tool head 60 may be oriented transversely relative to a longitudinal axis of the shaft 20,' e.g., such that a proximal end 60a of the tool head 60 is in the field of view of the endoscope 90 when the apparatus 10' is advanced to its distal position and/or otherwise manipulated, e.g., by surgeon actuation of the handle 40.'

Turning to FIGS. 3A and 3B, another embodiment of a surgical jaw 65" is shown, e.g., that may be provided on the apparatus 10' of FIG. 2. Unlike the previous jaw 65,' the jaw 65" incorporates a relatively longer jaw with increased reach 52" and/or special tines 54" to engage mating features on the tool head 60, for example, similar to a dissector or grasper tip.

Figure 16:
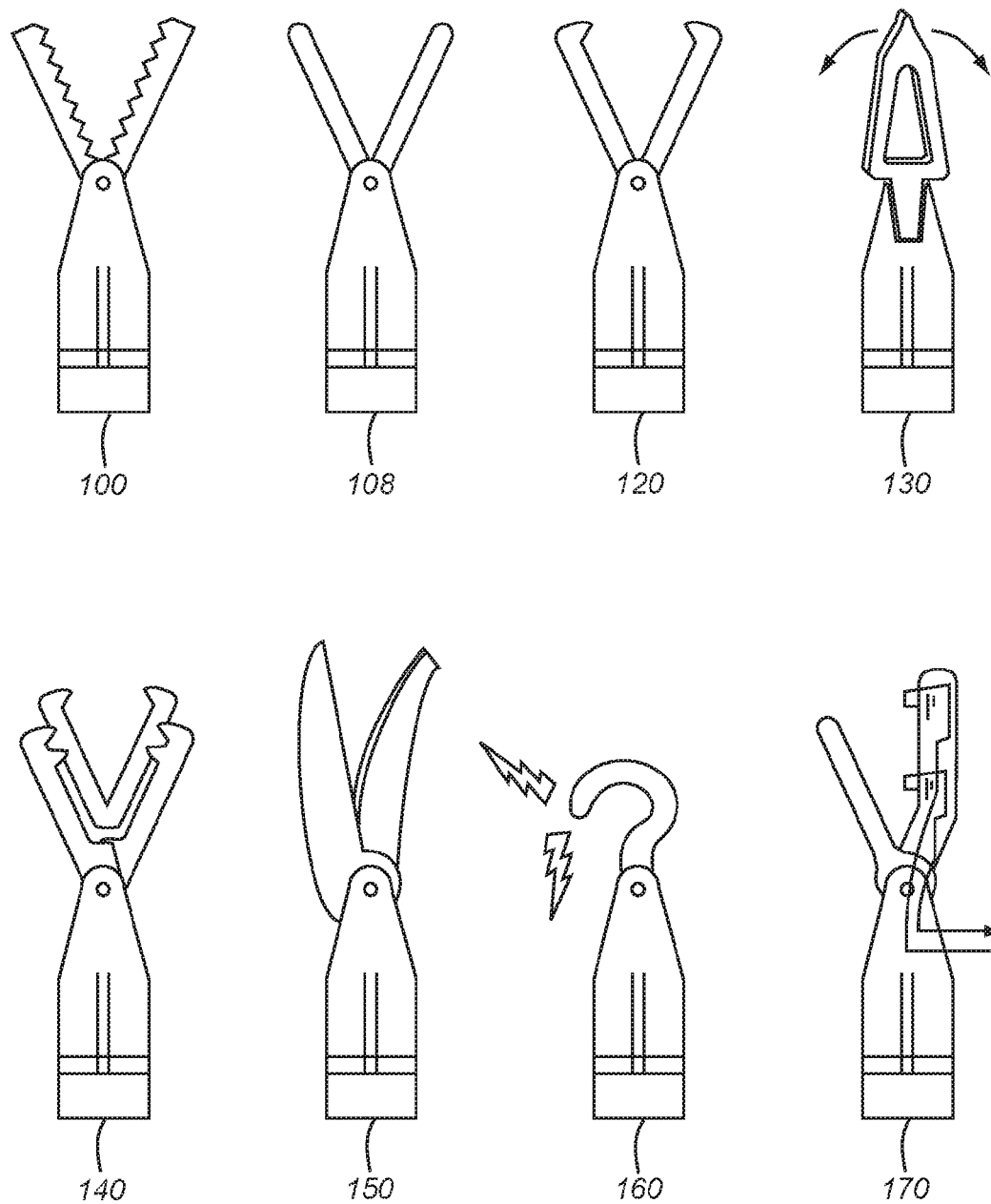
FIG. 16 shows a plurality of exemplary tool heads that may be introduced using the apparatus, systems, and methods described herein.

Alternatively, the surgical jaw 65" may be configured similar to existing standard tools as long as the surgical jaw 65" is capable of holding the tool head 60 safely and securely during the introduction process. For example, any grasper tip or dissector 130 (e.g., as shown in FIG. 16) with extended front jaws may be used with limited modification to the jaw 65" design shown and described herein, e.g., similar to the jaw 65" shown in FIGS. 3A and 3B with extended front teeth.

For example, if a standard tool is identified as having long enough jaws 65 so that the front tines 54 can reach the locking ring 62 of the tool head 60, then the tool head 60 may be inserted into the grasper jaws, e.g., as shown in FIGS. 3A and 3B, to minimize the exterior size envelope and make it easier to pass through a port.

Figure 4:
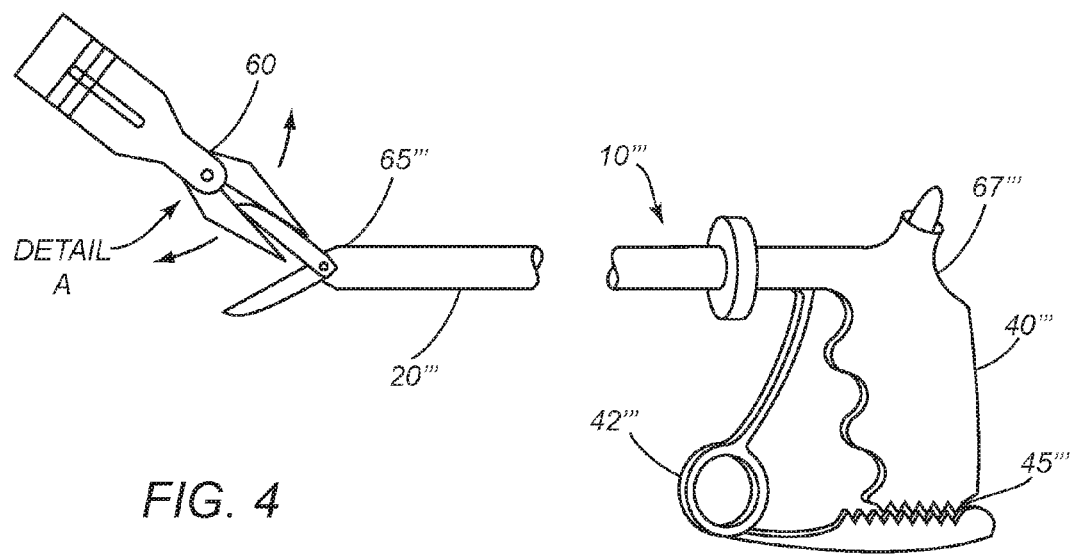
FIG. 4 is a perspective view of another embodiment of a carrier tool to which a modular tool head may be secured.
Figure 5A:
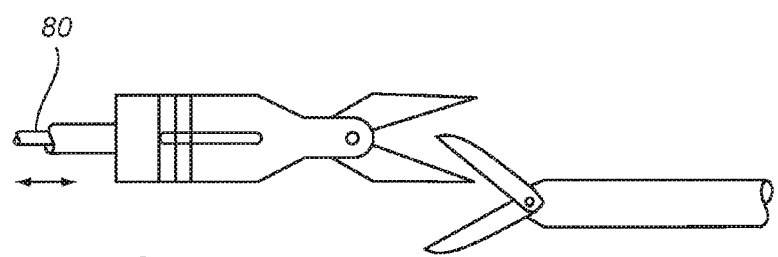
FIGS. 5A and 5B show jaws of the modular tool head being opened and closed to allow the tool head to be secured to jaws of the carrier tool.
Figure 5B:
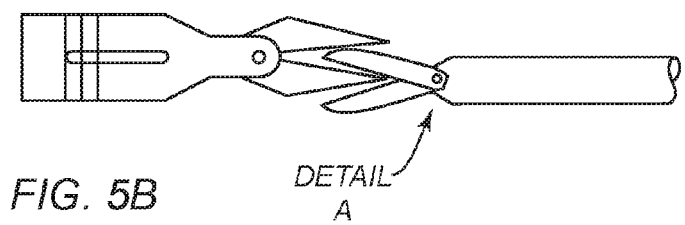

Turning to FIG. 4, another embodiment of a set of jaws 65''' is shown, which may be provided on a carrier tool, e.g., a standard tool 10,''' to introduce a modular tool head 60. The jaws 65''' may be used to introduce the tool head 60 using a method that involves engaging or grasping one of the jaws 65''' of the standard tool 10''' with the jaws of the modular tool head 60. For example, the modular tool head 60 may be constrained to one of the jaws 65''' of the standard tool 10,''' e.g., by actuating a set of forceps or other tool on the tool head 60 to close the tool head 60 onto one of the jaws 65,''' as shown in FIGS. 5A and 5B. Once introduced into a surgical space, the orientation and/or location of the tool head 60 may be adjusted by opening or closing the jaws 65''' of the standard tool e.g., to vary the angle of the modular tool head 60 relative to the standard tool 10.'''

Figure 5C:
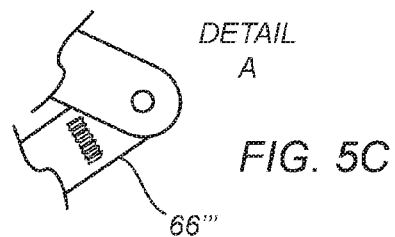
FIG. 5C is a detail of optional detents that may be provided on either or both jaws.

Optionally, to ensure effective locking of the modular tool head 60 to the standard tool jaws 65,''' detents 66''' may be provided on either or both the modular tool head 60 or/and the standard tool jaws 65,''', as shown in FIG. 5C. The detents 66''' on the modular tool head 60 may be sufficient to maintain engagement to the standard jaw 65,''' e.g., until the control shaft 80 activates the modular tool head 60 and overcomes the detents 66.''' The detents 66''' on the standard jaw 65 may be sufficient to maintain engagement to the modular tool 60 until the handle 67''' of the standard tool 10''' overcomes the detents 66.'''

Figure 6:
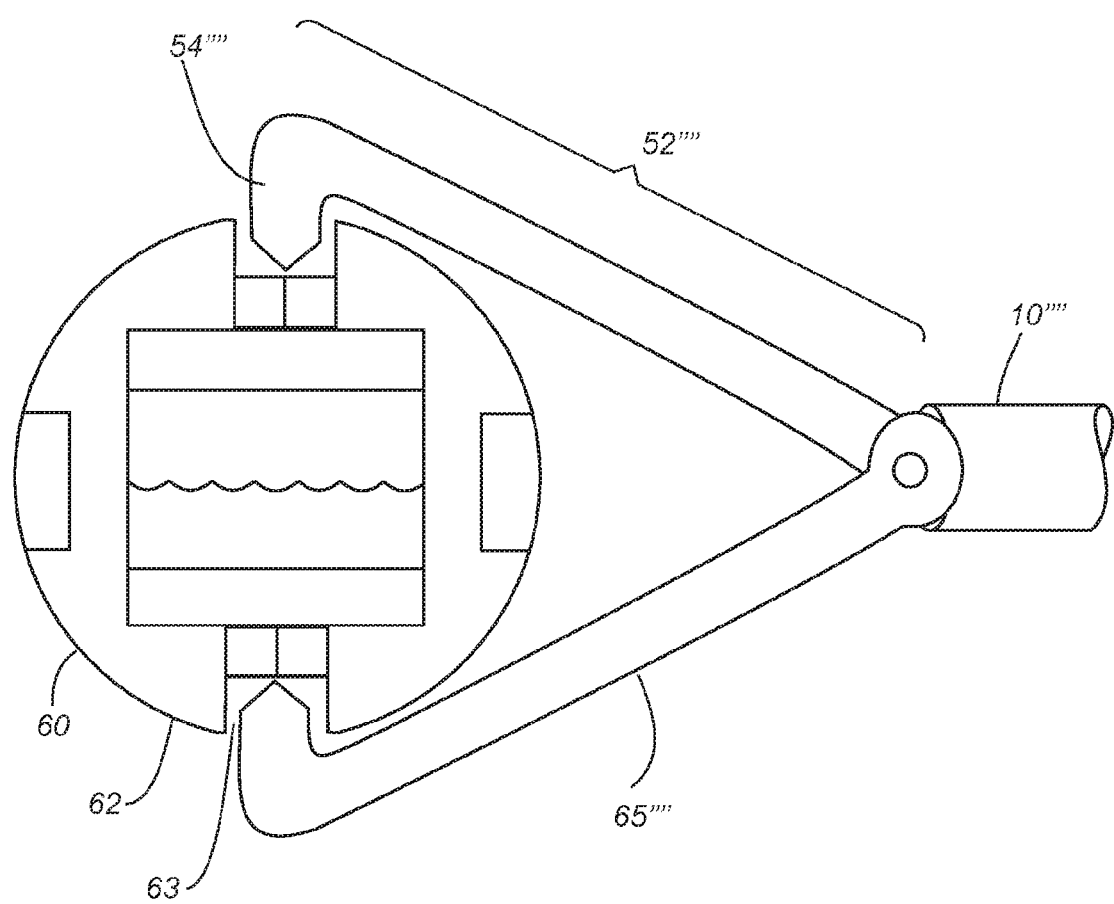
FIG. 6 is a side view of a distal end of yet another embodiment of a carrier tool including jaws with features for securing a modular tool head to the carrier tool.

Turning to FIG. 6, a distal end of yet another carrier tool 10'''' is shown that includes a set of jaws 65'''' that may be used to secure a modular tool head 60 to the carrier tool 10'''' with a transverse, e.g., substantially perpendicular, alignment relative to a longitudinal axis of the carrier tool 10.'''' An embodiment of the surgical jaw 65'''' may include a lengthened jaw with expanded reach 52'''' and/or special tines 54'''' that may engage mating features on the tool head 60. For example, the jaws 65'''' may be configured such that existing standard tools can hold the tool head 60 safely and securely during the introduction process, similar to the previous embodiment.

For example, as shown, the tool head 60 may include a locking ring 62 with grooves 63 sized such that the lengthened jaw 65'''' with expanded reach 52'''' may be in a fully open position when the front tines 54'''' and the locking ring 62 are engaged. Such an embodiment may reduce the risk of the tool head 60 being accidentally released prematurely, since the jaws 65'''' cannot be opened further to release the tool head 60, while maintaining operating principles similar to the previous embodiments.

Optionally, any of the embodiments herein, e.g., the embodiments of FIGS. 3, 4, and 6, may incorporate a grip locking function, similar to the grip locking features 45'''' shown on the handle 40'''' of FIG. 4. The grip locking features 45'''' may be configured to lock the surgical jaw 65''' closed around the tool head 60. While the surgical jaw 65''' is locked on the tool head 60, the tool head 60 may still be unlocked from the surgical jaw 65,''' e.g., by the control shaft 80 of a laparoscopic tool introduced into the surgical space to receive the tool head 60, as described elsewhere herein or in the applications incorporated by reference herein. The grip locking features 45''' may lock the relative position of the surgical jaws 65''' relative to the shaft 20''' and/or each other. Optionally, any of the embodiments herein, e.g., the embodiments of FIGS. 3, 4, and 6, may incorporate four jaws instead of two jaws (not shown).

Figure 7A:
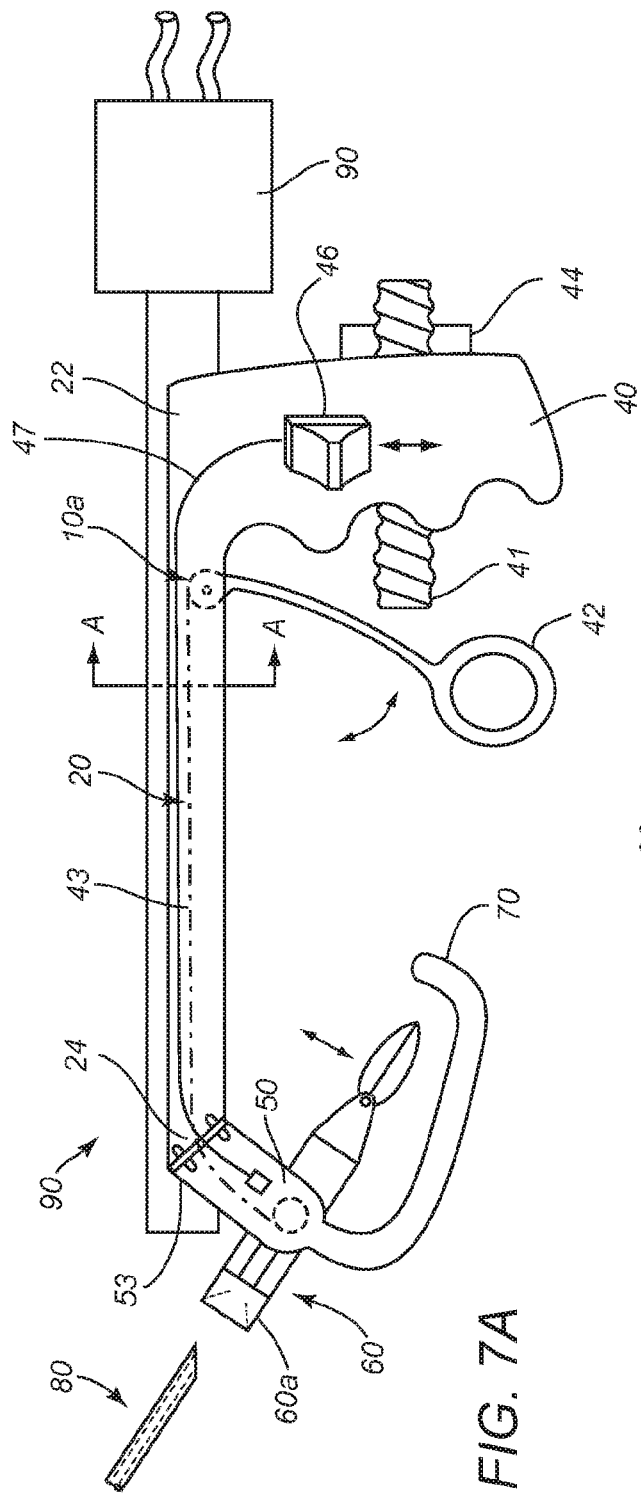
FIG. 7A is a side view of still another exemplary embodiment of a carrier tool coupled to an endoscope for introducing a tool head into a surgical space.

Turning to FIG. 7A, another embodiment of an introduction apparatus or carrier tool 10*a* is shown that incorporates a substantially cylindrical sheath 20 with a housing 50 including two or more protruding ears 51 extending adjacent an endoscope 90 to which the apparatus 10*a* may be secured. Generally, the apparatus 10*a* includes an elongate sheath 20 including a proximal end 22 and a distal end 24, a moveable handle 40 on the proximal end 22, and two or more protruding ears 51 on the distal end 24 for carrying and/or rotating a tool head 60. Rotating the tool head 60 may be achieved by manipulating a trigger or first actuator 42, thereby actuating a connecting rod or wire 43. The handle 40 may include a thumb slide or other second actuator 46 for operating the protruding ears 51 to engage and/or release the tool head 60, e.g., by actuating a connecting rod or wire 47. The housing 50 may include a hinge 53 that is connected to thumb slide 46 via connecting rod or wire 47. When the thumb slide 46 is manipulated by the surgeon, the ears 51 of the housing 50 may selectively open and close to engage or release the tool head 60.

The cylindrical sheath 20 may be configured to at least partially surround the endoscope 90 and carry the housing 50 and protruding ears 51. Similar to previous embodiments, the sheath 20 may have a desired length and/or be sufficiently rigid to maintain the position of the ears 51 relative to the endoscope lens 90. Also similar to the previous embodiments, the sheath 20 may be movable longitudinally along the endoscope 90 and/or rotatable at least partially around the endoscope 90.

The sheath 20 may have a length such that the handle 40 is disposed outside of the patient's body and next to the endoscope 90. The handle 40 may include a trigger or other first actuator 42 and/or a thumb slide or other second actuator 46, which may be actuated to actuate the protruding ears 51. The handle 40 may allow the surgeon to slide the entire apparatus 10*a* onto the endoscope 90, advance the apparatus 10*a* into the patient's body and into the field of view of the endoscope 90, and/or remove the apparatus 10*a* from the patient's body or otherwise relative to the endoscope 90. Once the tool head 60 is in the field of view of the endoscope 90, actuation of the handle 40 may also allow the surgeon to manipulate the position of the tool head 60 within the field of view. Optionally, the apparatus 10*a* may include a stop 41, e.g., within or otherwise coupled to the handle 40 when the apparatus 10*a* has been introduced to the appropriate depth relative to the endoscope 90.

The protruding ears 51 may be attached to or otherwise carried by the housing 50 and/or the distal end 24 of the sheath 20. The ears 51 may be moveable by actuation of the trigger 42 and/or thumb slide 46 attached to handle 40, e.g., such that the ears 51 may be manipulated by the surgeon from outside the patient's body. The ears 51 may include one or more shroud elements 70 to at least partially cover the standard sized tool head 60, e.g., including proximal and/or distal conical or other tapered features to facilitate insertion and/or removal from the patient's body. For example, similar to the previous embodiments, the ears 51 may be configured to serve one or more purposes, e.g., lock the tool head 60 to the housing 50 until it is unlocked by the control shaft or it is released by the thumb slide 46, orient the tool head 60 by actuating trigger 42 such that the surgeon is able to see the appropriate end of the tool head 60 for assembly, and/or at least partially cover the tool head with the shroud 70.

The tool head 60 may be locked into the ears 51 by an operator outside of the patient's body, e.g., by loading and rotating the tool head 60 relative to the ears 51. The orientation of the tool head 60 with respect to the ears 51 may be such that a proximal end 60*a* of the tool head 60 is in the field of view of the endoscope 90 when the apparatus 10*a* is advanced to its final position and manipulated by actuation of the handle 40 and trigger 42. Optionally, the tool head 60 may be rotated or otherwise reoriented with respect to the ears 50, e.g., via mechanisms such as pulling/pushing of rods or geared hinges (not shown) on the housing 50, similar to other embodiments herein. Movement of the sheath 20 and/or tool head 60 may facilitate proper alignment of the tool head 60 relative to a thin cannular tube or shaft 80 of a surgical tool introduced into the surgical space to receive the tool head 60.

Turning to FIG. 8, another embodiment of a carrier tool 10*b* is shown that includes a shaft 20 and handle 40, similar to previous embodiments, and a movable distal housing 50*b* for carrying a tool head 60. The housing 50*b* may be rotated about a rotational axis transverse to the longitudinal axis of the shaft 20, e.g., via actuation of a thumb slide or other first actuator 46 around hinge 21, and the tool head 60 may be further rotatable, e.g., by actuation of trigger or other second actuator 42. When the operator manipulates the thumb slide

46 and/or trigger 46, the tool head 60 may be directed between a substantially coaxial-to-the-endoscope state 12, a substantially perpendicular-to-the-endoscope state 14, and a substantially parallel-to-the-endoscope state 16, as shown in FIGS. 8A-8C, respectively.

Figure 10A:
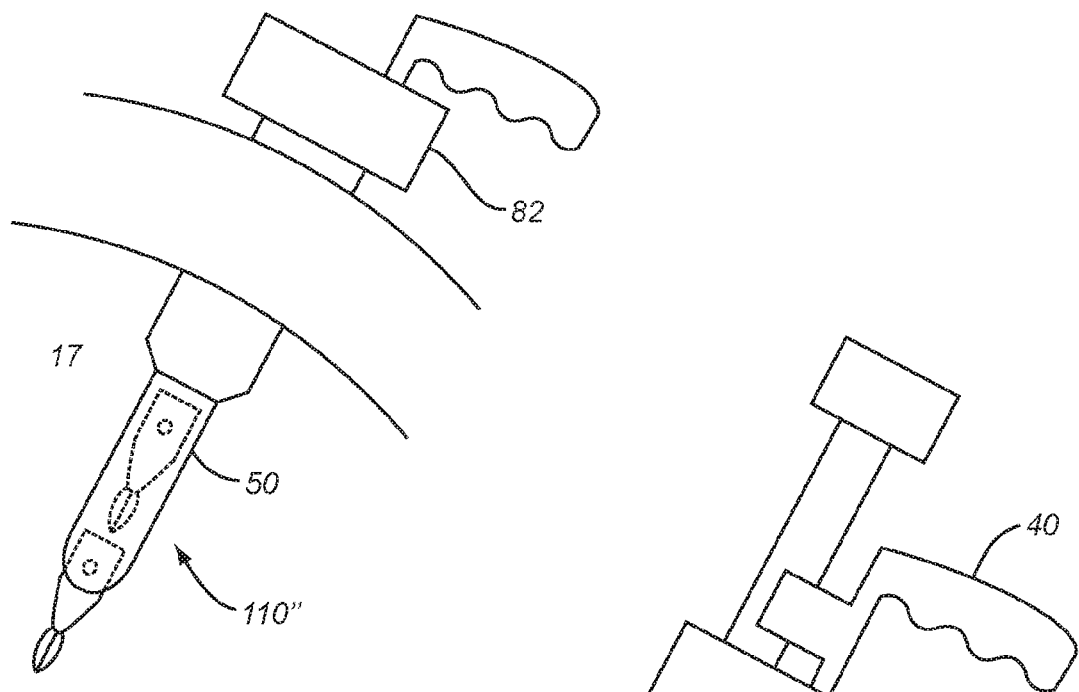
FIG. 10A is a cross-sectional view of a patient's body showing a carrier tool with a substantially straight housing carrying a plurality of tool heads being introduced into a surgical space through a trocar.

Turning to FIG. 9, another exemplary embodiment of a tool carrier 110 is shown that includes a tool holding housing 50 capable of holding multiple tool heads 60, e.g., in a rail or spline 56 coupled to an elongate shaft 20 by a hinge 21. As shown, the spline 56 may include a pair of spaced apart elongate members defining a generally circular cross section (or alternatively, a rectangular, square, or other polygonal cross-section), e.g., as shown in FIG. 9A, between which the tool heads 60 may be secured. Optionally, the tool carrier 110 may include one or more clip elements (not shown) for slidably securing a shaft of the tool carrier 110 to an endoscope (also not shown). Alternatively, the housing 50 of the tool carrier 110 may be introducible into a surgical space independently of an endoscope, e.g., through a trocar or other port, as shown in FIG. 10A. In addition or alternatively, the carrier tool 110 may include similar advancement and/or actuation features as previously described, e.g., including trigger 42 on handle 40.

In an alternative embodiment, the housing 50 may be eliminated altogether by holding the tool heads 60 on rails or splines 56 in a carrier tool 110,' as shown in FIG. 9B. The method of using a rail 56 and eliminating the housing 50 also demonstrates a way by which the "tool holder" and "housing" 50 are one in the same and thus eliminates concern surrounding a connection between the two.

Figure 10B:
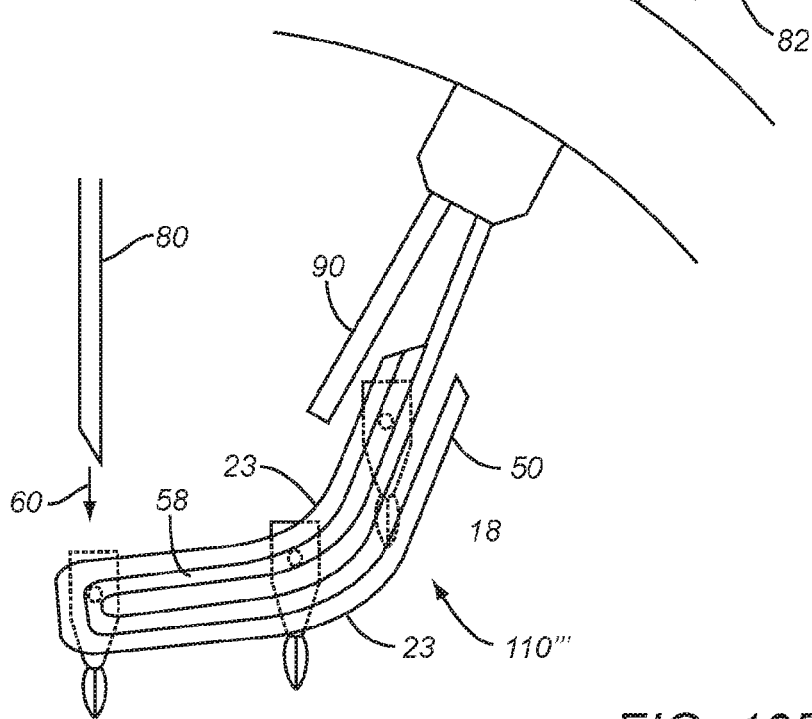
FIG. 10B is a cross-sectional view of a patient's body showing a carrier tool with a curved housing carrying a plurality of tool heads attached to an endoscope and being introduced into a surgical space through a trocar.

Turning to FIGS. 10A and 10B, the housing 50 of the carrier tool 110," 110''' may be substantially rigid or malleable, e.g., to provide a desired shape or configuration for the housing 50 and/or to accommodate different levels of space availability in the surgical cavity, e.g., within an abdomen. For example, FIG. 10A shows a carrier tool 110" including a housing 50 having a substantially straight shape 17, e.g., extending substantially parallel to a longitudinal axis of the carrier tool, while FIG. 10B shows a carrier tool 110''' including a housing 50 having a curved or "L" shape 18. Any of these carrier tools may be attached to an endoscope 90 via various mechanisms, such as the clip elements described elsewhere herein.

In a straight formation, e.g., as shown in FIG. 10A, each tool head 60 may have its own compartment 23 and may be rotated in one or more degrees of freedom, allowing for accurate alignment with the control shaft 80 (not shown, see, e.g., FIG. 10B).

In a curved configuration, e.g., as shown in FIG. 10B, the tool heads 60 may be movable along a conveyer belt 58, e.g., to a tip of the housing 50, to facilitate attachment to the control shaft 80. The rotation and/or exchange of the tool heads 60 may be actuated from the proximal end of the carrier tool 110,''' e.g., using an actuator (not shown) on the handle 40. For example, a ratchet-type actuator may cause a sliding action, advancing the tool heads around the conveyor track 58 until the desired tool is presented, e.g., within the field of view of the endoscope 90.

Figure 11A:
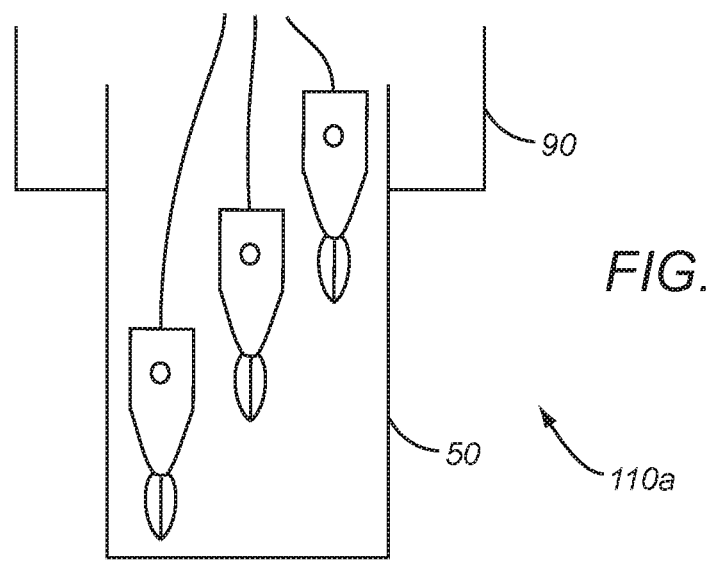
FIGS. 11A and 11B are side views of a distal end of another embodiment of a carrier tool including a housing carrying a plurality of tool heads, showing the tool heads retracted within and deployed from the housing, respectively.
Figure 11B:
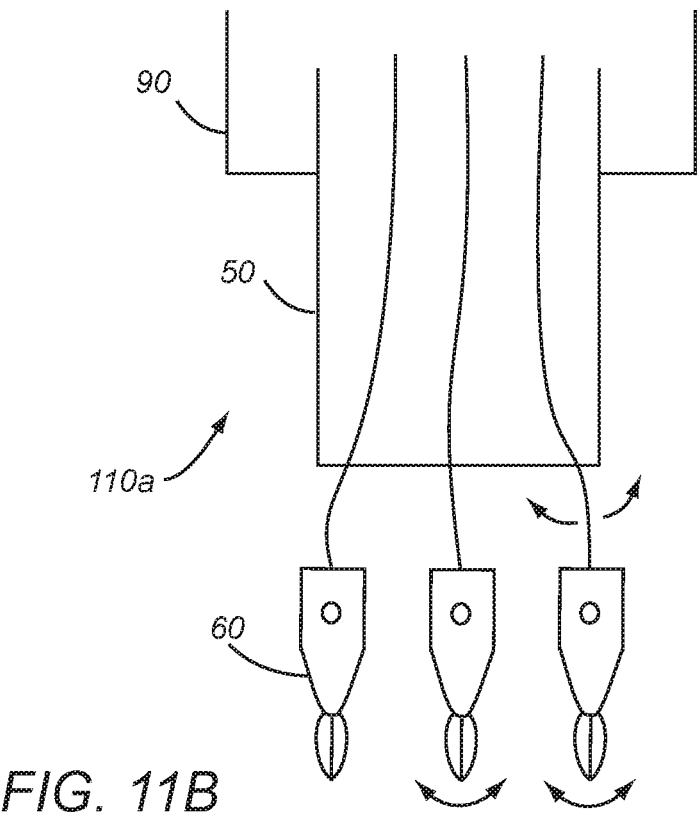

Turning to FIGS. 11A and 11B, another embodiment of a carrier tool 110a is shown that includes multiple tool heads 60 carried within a housing 50, which may be provided on a distal end of a shaft (not shown) and/or include other features similar to other embodiments herein. Each tool head 60 may be releasably carried by a cable or other elongate member, which may be biased away from one another yet may be resiliently straightened within the housing 50. For example, as shown in FIG. 11A, the tool heads 60 may be collapsed substantially in single file longitudinally inside the housing 50, e.g., such that a cross-sectional profile of the housing 50 may be minimized. As shown in FIG. 11B, the cluster of tool heads 60 may be advanceable from the housing 50, whereupon one or more of the tool heads 60 may be directed away from the others within the surgical space to facilitate selecting and/or attaching a desired tool to a control shaft of a surgical tool (not shown). Optionally, each tool head 60 may have one or more degrees of freedom, e.g., to allow the tool heads 60 to rotate and/or otherwise align with the control shaft.

Figure 12A:
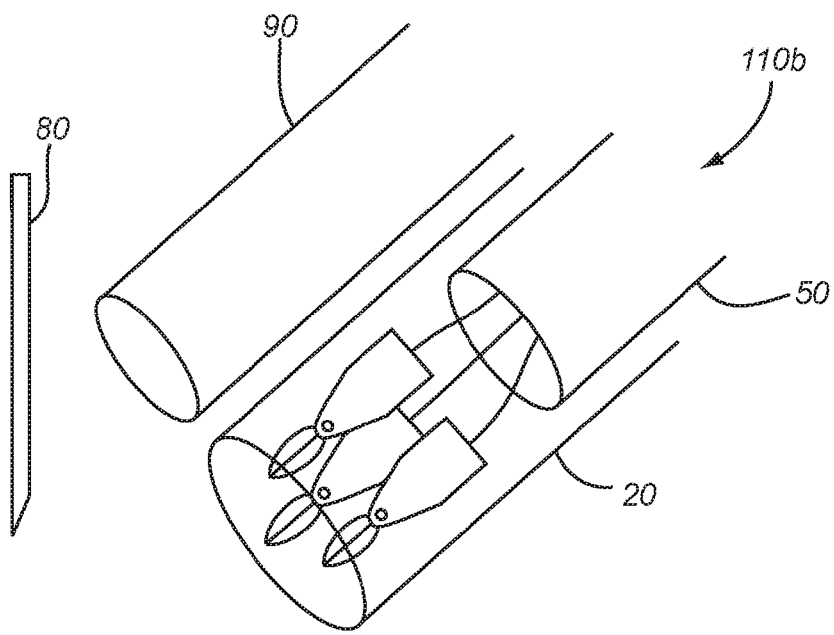
FIGS. 12A and 12B are perspective views of a distal end of yet another embodiment of a carrier tool including a housing carrying a plurality of tool heads and attached to an endoscope, showing the tool heads retracted within and deployed from the housing, respectively.
Figure 12B:
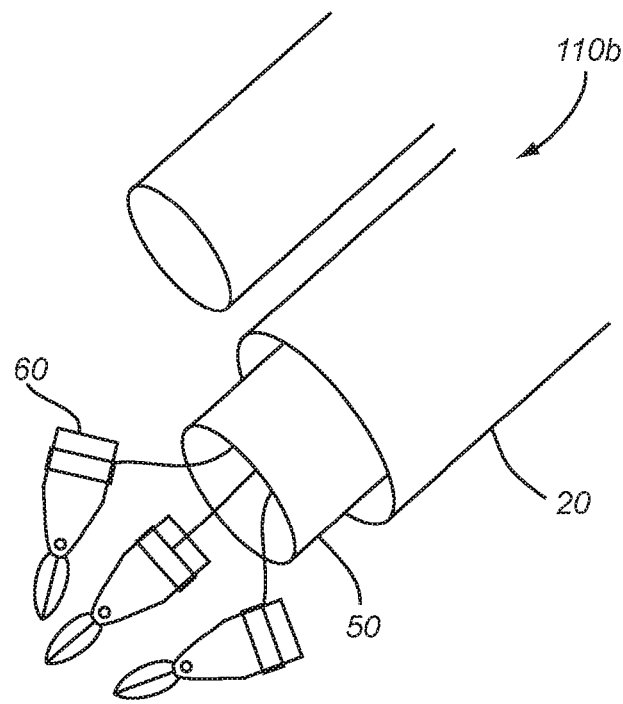

Turning to FIGS. 12A and 12B, an alternative embodiment of a carrier tool 110b is shown that includes a delivery housing 50 connected to an introduction shaft 20 that holds multiple tool tips 60 that expand in a radial fashion from a central axis. The tool heads 60 may be aligned substantially in single file longitudinally or in other orientations as part of the delivery housing 50 in front of the endoscope 90, as shown in FIG. 12A. As shown in FIG. 12B, after the tool heads 60 have been advanced from the delivery housing 50, the tool heads 60 may expand outwardly, exposing each tool head 60. The housing 50 may be rotated to position one of the tool heads 60 within the field of view of the endoscope 90, e.g., to facilitate attaching the selected tool head 60 to the control shaft 80. Each tool head 60 may have one or more degrees of freedom to pivot and/or rotate, e.g., to facilitate align a desired tool head 60 with the control shaft 80.

Figure 13:
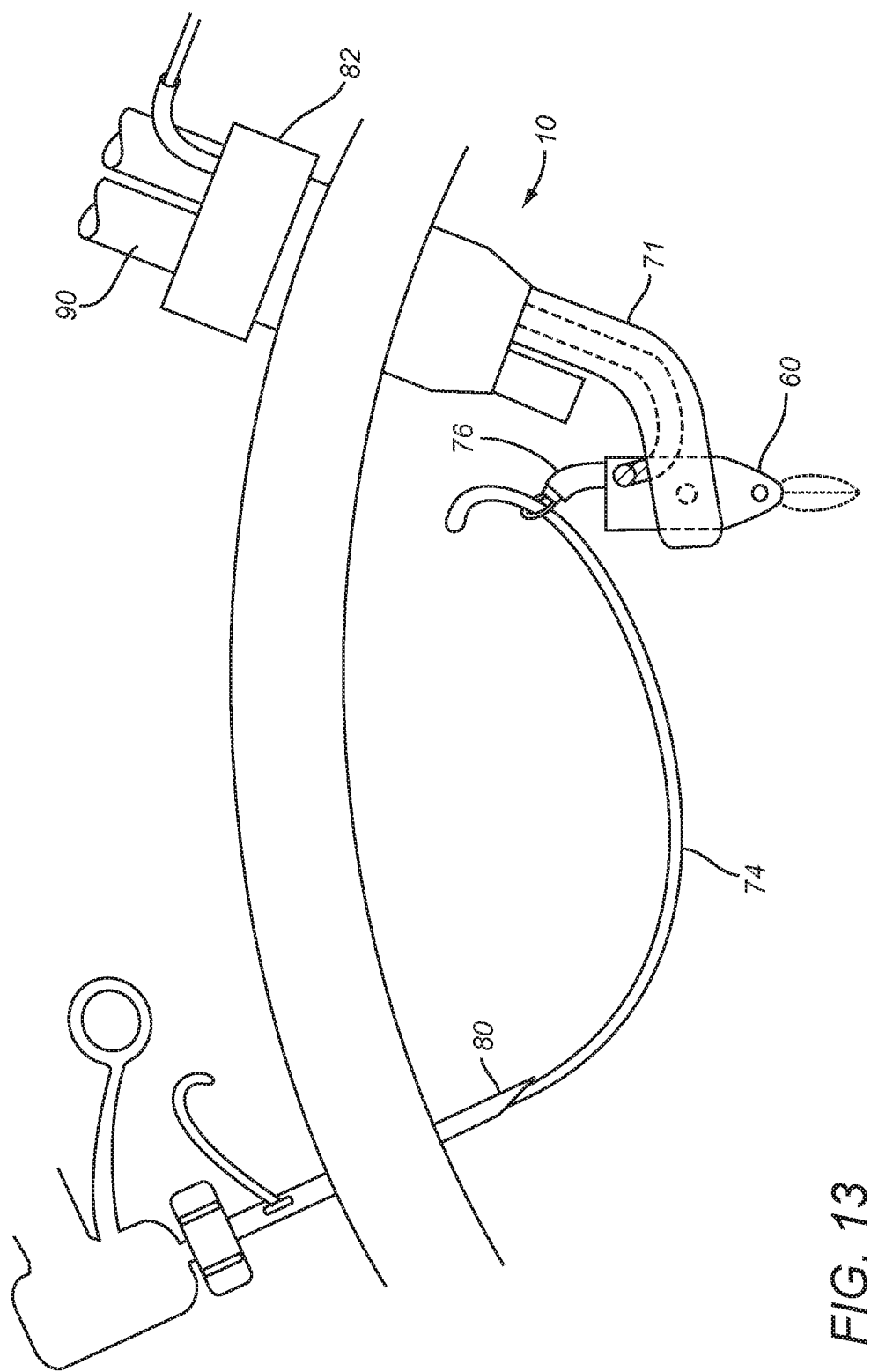
FIG. 13 is a cross-sectional view of a patient's body showing a carrier tool introduced into a surgical space through a trocar along with an endoscope, and including a wire rail to facilitate attaching a tool head carried by the carrier tool to a control shaft.

Turning to FIG. 13, an exemplary embodiment of a system and method are shown for introducing a tool head 60 into a surgical space and attaching the tool head 60 to a control shaft 80 for performing a surgical procedure within the surgical space. Generally, the system includes a carrier tool 10, which may be any of the embodiments described elsewhere herein, e.g., attached to an endoscope 90 such that the carrier tool 10 and endoscope 90 may be introduced together through a trocar 82 into the surgical space. As shown, the system includes a wire rail 74 to assist in assembly of the tool head 60 and the control shaft 80. Optionally, this system may use a wire rail 74 in addition to or instead of a mechanism at the end of the endoscope 90.

The procedure to placing the wire rail 74 may be similar to procedures used to place a percutaneous gastric feeding tube. For example, the following steps may be used:

1) a wire 74 may be placed through or otherwise adjacent the percutaneous control shaft 80;
2) a snare 76 may be passed next to the endoscope 90 and used to grab the end of the wire 74;
3) the snare 76 and, consequently, the wire 74 may be pulled out of the umbilicus, e.g., adjacent the endoscope;
4) the tool head 60 may be threaded onto the wire 74 and introduced into the body cavity via the umbilicus, e.g., using a flexible introduction tube 71 (or alternatively, any of the carrier tools described herein) advanced along the endoscope 90 or independently of the endoscope 90. For example, as shown, the tool head 60 may ride in the end of the flexible introduction tube 71;
5) the operator may push the tube 71 and/or the wire 74 may be manipulated to guide the tool head 60 towards the control shaft 80, e.g., until they mate up at the end of the percutaneous control shaft 80; and
6) the tool head 60 may be loaded onto the percutaneous control shaft 80, e.g., as described elsewhere herein and in the applications incorporated by reference above.

Figure 14:
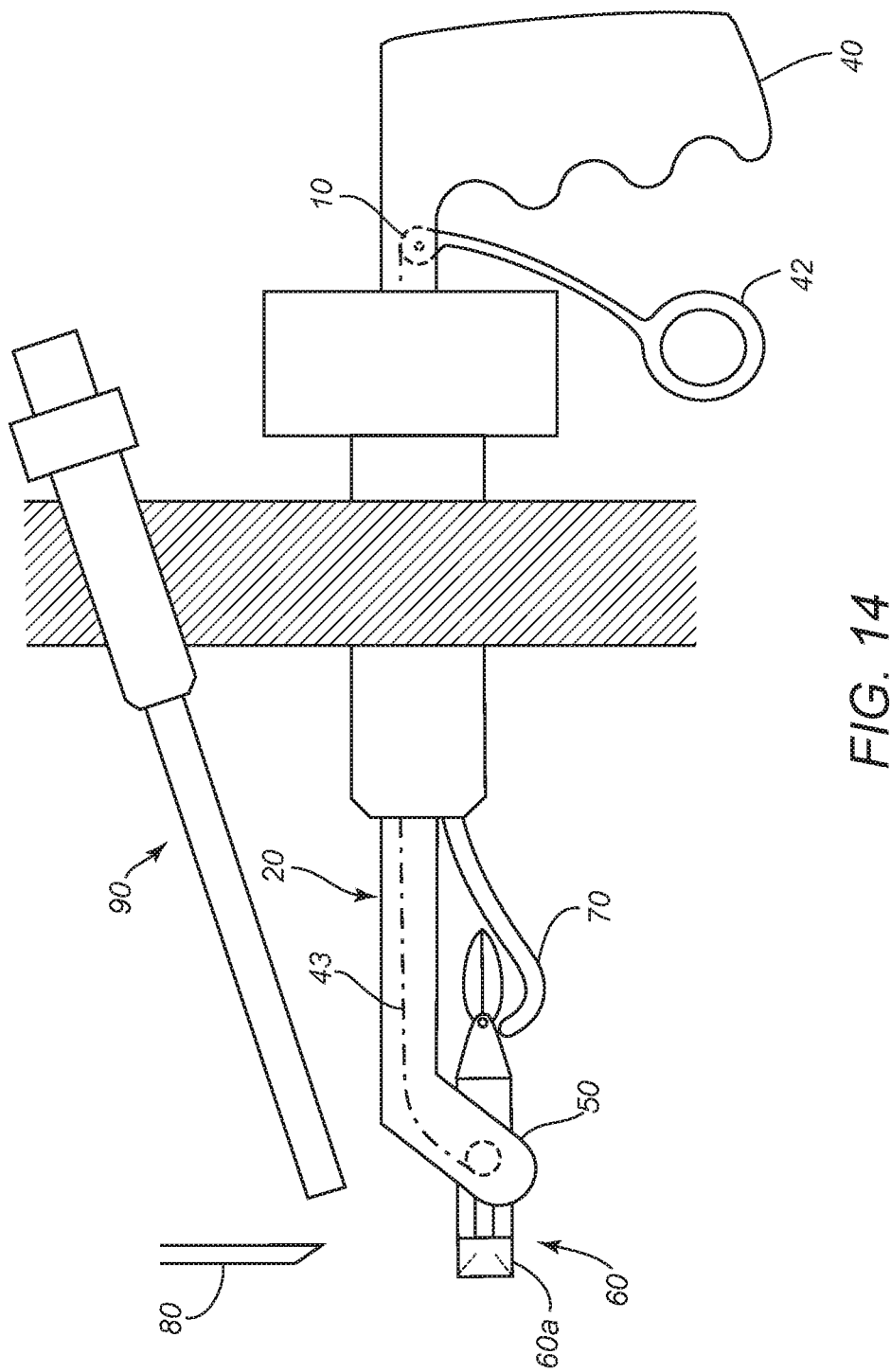
FIG. 14 is a cross-sectional view of a patient's body showing a carrier tool introduced into a surgical space through a trocar independent of an endoscope, showing a method for attaching a tool head carried by the carrier tool to a control shaft.

Turning to FIG. 14, a system is shown for introducing a tool head 60 into a surgical space and/or connecting the tool head 60 to a control shaft 80. Unlike previous embodiments, the introduction apparatus 10 may be introduced at a separate location from where the endoscope 90 is introduced into the patient's body. The introduction apparatus 10 may generally include a shaft 20, a handle 40, and a housing 50, e.g., similar to other embodiments described elsewhere herein, but without clip elements to attach to the endoscope 90. The housing 50 of the apparatus 10 may carry the tool head 60, e.g., by locking onto the tool head 60 and/or orienting the tool head 60 relative to the endoscope 90. Thus, the surgeon may be able to see the appropriate end of the tool head 60 intended for assembly, e.g., by manipulation of a trigger or other actuator 42, thereby actuating a connecting rod or wire 43 within the shaft 20. As shown, the introduction apparatus 10 may be introduced through a separate trocar or other port than the endoscope 90.

As shown, the handle 40 may extend outside of the patient's body when the housing 50 and tool head 60 are disposed within the surgical space. The handle 40 may allow the surgeon to advance the apparatus 10 into the body, into the field of view of the endoscope 90, and/or to remove the apparatus 10 from the patient's body.

The housing 50 may be attached to or otherwise provided on the distal end of the shaft 20, similar to other embodiments herein. Thus, the housing 50 may serve one or more purposes similar to other embodiments herein, e.g., lock the tool head 60 to the housing 50 until it is unlocked by the control shaft 80, orient the tool head 60, and/or shroud the ends of the tool head 60. Optionally, a shroud 70 may be provided to at least partially cover the tool head 60, e.g., with proximal and/or distal conical or other tapered features, e.g., to facilitate insertion into and/or removal from the patient's body.

During use, the tool head 60 may be locked into the housing 50 by an operator outside of the patient's body, e.g., by loading and rotating the tool head 60 relative to the housing 50. The orientation of the tool head 60 within the housing 50 may be such that the proximal end 60a of the tool head 60 is in the field of view of the endoscope 90 when it is advanced to its distal position, as described elsewhere herein.

Any of the apparatus herein may be used to perform one or more surgical or other procedures within a patient's body, e.g., within a surgical space within the patient's abdomen or within other locations. For example, turning to FIG. 15, an exemplary method will now be described with reference to the apparatus 10 of FIG. 1, although it will be appreciated that similar methods may be performed with any of the embodiments herein. Generally, the apparatus 10 may include an elongate shaft 20, a handle 40, a trigger 42, a stop 41, a connecting wire or rod 43, a housing 50, and/or a slotted clip 30, e.g., similar to other embodiments described elsewhere herein.

Figure 15:
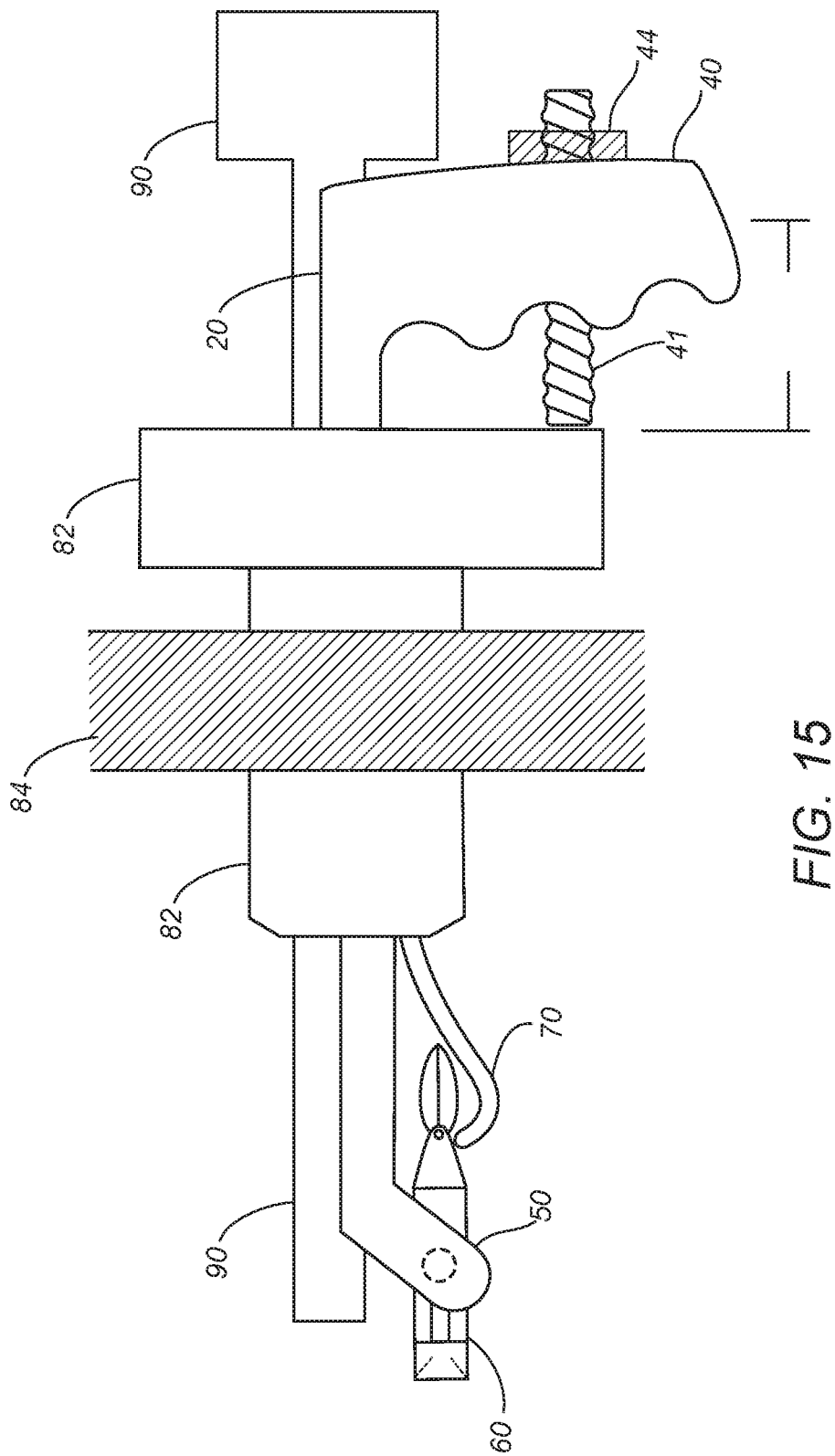
FIG. 15 is a cross-sectional view of a patient's body showing a method for attaching a tool head carried by the carrier tool of FIG. 1 to a control shaft.

Initially, the surgeon may load a desired tool head 60 into the housing 50. The surgeon may then check the ability to manipulate the tool head 60 by grasping the handle 40 and actuating the trigger 42. Next, the surgeon may introduce the endoscope 90 into a surgical space within the patient's body, e.g., using a trocar or other port 82 to cross the abdominal wall 84, e.g., as shown in FIG. 15. After the surgeon is comfortable with the state of the abdomen, she may remove the endoscope 90 from the trocar 82 and load the shaft 20 onto the endoscope 90, e.g., utilizing clip features similar to the clip 30 shown in FIGS. 1 and 1A. Next, the surgeon may adjust the depth of the stop 41, e.g., with the thumb wheel 44. Next, she may shroud the tool head 60 with the shroud 70 and introduce the entire assembly into the abdomen, e.g., until the stop 41 hits abdominal tissue or trocar 82. After the apparatus 10 is in the abdomen, the shroud 70 may release and the surgeon may be able to rotate the tool head 60 into the field of view of the endoscope 90.

Subsequently, the control shaft 80 may be introduced into the surgical space, e.g., through another trocar or other port (not shown), and inserted into the tool head 60, e.g., while monitoring the procedure within the field of view of the endoscope 90. With the tool head 60 coupled to the control shaft 80, the tool head 60 may be used to perform a procedure, e.g., one or more steps of a surgical procedure, such as those described elsewhere herein and in the applications incorporated by reference herein. If desired, at any time, the tool head 60 may be removed from the control shaft 80, e.g., by recoupling the tool head 60 to the carrier tool 10, and, optionally, another tool head 60 may be introduced and coupled to the control shaft 80 in a similar manner. Thus, one or more tool heads may be introduced sequentially into a surgical space to perform a series of steps or procedures, as desired. Once the desired procedure(s) is completed, the carrier tool 10, control shaft 80, endoscope 90, and/or any other devices may be removed from the patient's body using conventional methods.

Alternatively, with additional reference to FIG. 2, the apparatus 10' may be used in a similar manner. As described above, the apparatus 10' may include an elongate shaft 20, a handle 40, a trigger 42,' a stop 41,' a connecting wire or rod 43,' a standard surgical jaw or forceps 65,' and a slotted clip 30' attached in parallel to the introduction shaft 20.' The surgeon may first load a tool head 60 into the surgical jaw 65.' The surgeon may then check the ability to manipulate the tool head 60 by grasping the handle 40' and actuating the trigger 42,' Next, the surgeon may introduce the endoscope 90 into the body, e.g., using a trocar or other port 82 to cross the abdominal wall 84, as shown in FIG. 15.

After the surgeon is comfortable with the state of the abdomen, she may remove the endoscope 90 from the trocar 82 and load the shaft 20' onto the endoscope 90, e.g., utilizing clip 30.' Next, the surgeon may adjust the depth of the stop 41,' e.g., with the thumb wheel 44.' Next, she may shroud the tool head 60 with the shroud 70 and introduce the entire assembly into the abdomen, e.g., until the stop 41' hits abdominal tissue or trocar 82. After the apparatus 10' is in the abdomen, the shroud 70' may release and the surgeon may rotate or otherwise manipulate the apparatus 10' to position the tool head 60 within the field of view of the endoscope 90, e.g., by actuating jaw 65' with trigger 42.' Subsequently, the control shaft 80 may be inserted into the tool head 60 in the field of view of the endoscope 90, and coupled to the tool head 60, similar to other embodiments herein.

Turning to FIG. 3, alternatively, the lengthened jaw 65" with extended reach 52" and special tines 54" may be incorporated into the apparatus 10' shown in FIG. 2. It will be appreciated that extending the reach and/or incorporating special tines may facilitate engaging and introducing a variety of tool heads, such as any of the tool heads shown in FIG. 16. The special tines 54" may mate with corresponding features in a locking ring 62 of the tool head 60, as shown in FIG. 3.

Turning to FIG. 4, an alternative embodiment of an apparatus 10''' may be used that includes a detent controlled engagement system, which may be provided on any of the embodiments herein to facilitate introduction and/or manipulation of a tool head 60. As shown, the apparatus 10''' may include first and second sets of detent locks 66,''' 45.''' The first set of detent locks 45''' may be included on the handle 67''' and trigger 42.''' The saw-tooth like detents 45''' may provide a friction interface between the manipulation trigger 42''' and the handle 67,''' allowing the trigger 42''' to be pulled towards the handle 67''' while preventing subsequent movement away until the detents 45''' are affirmatively disengaged by the user.

Thus, the first detent locks 45''' may allow the surgeon to control the position of surgical jaw 65.''' The second detent lock 66''' may be provided between the jaws of the tool head 60. This second detent lock 66''' may allow the surgeon to rigidly attach the tool head 60 to the surgical jaw 65.''' For example, once the tool head 60 is introduced into the body, the second detent system 66''' may be overcome, e.g., by coupling the tool head 60 to the control shaft 80 and manipulating the jaws of the tool head 60 by actuation of control shaft 80.

Turning to FIG. 6, an alternative carrier tool 10'''' may be used in a similar manner to the embodiments of FIGS. 2-4, e.g., by engaging and releasing the tool head 60 with the surgical jaw 65.'''' The carrier tool 10'''' may carry a tool head 60 in a predetermined orientation, e.g., substantially perpendicular to the shaft, which may be facilitated by the lengthened jaws with extended reach 52'''' and/or the special tines 54,'''' which may be configured to be received in corresponding tool head grooves 63 and/or otherwise engage the locking ring 62.

Figure 7B:
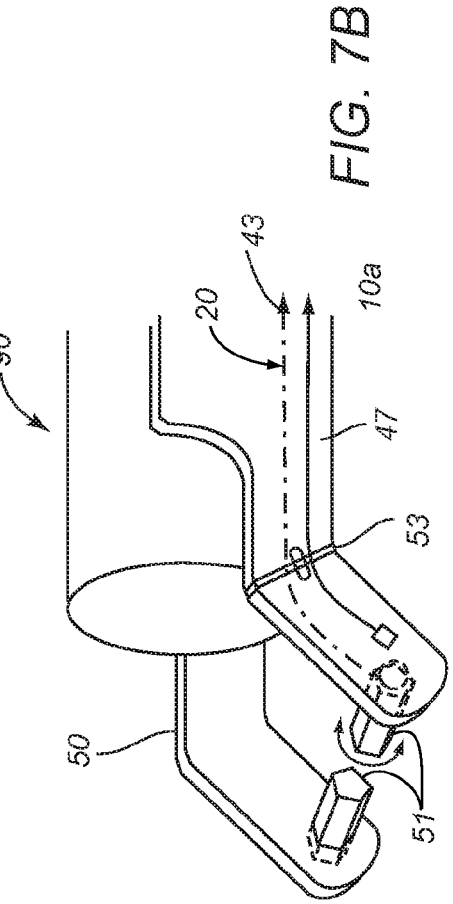
FIG. 7B is a detail of a distal end of the carrier tool and endoscope of FIG. 7A.

Turning to FIGS. 7A and 7B, the apparatus 10a may also used in a similar manner. As described above, the apparatus 10a includes an elongate shaft 20, a handle 40, a trigger 42, a thumb slide 46, a stop 41, a tool head manipulation connecting wire or rod 43, a housing hinge 53 manipulation connecting wire or rod 47, a housing 50, a tool head shroud 70 attached to hinge 50, protruding ears 51 that engage locking ring 62 and are sufficiently featured to transmit rotation generated by trigger 42, a rigid stop 41, a thumb wheel 44, and a slotted clip 30. The surgeon may first load a tool head 60 into the housing 50 and protruding ears 51, e.g., by sliding the tool head 60 into the housing 50 and/or by opening the housing 50, e.g., by activating the housing hinge 53 by sliding the thumb slide 46. The surgeon may load the tool head 60 until the ears 51 mate with corresponding features on the locking ring 62 of the tool head 60. If the surgeon used thumb slide 46 to activate housing hinge 53, then she may reverse the position of the thumb slide 46 and close housing 50.

The surgeon may then check the ability to manipulate the tool head 60, e.g., by grasping the handle 40 and actuating the trigger 42. Next, the surgeon may introduce the endoscope 90 into the patient's body, e.g., using a trocar 82 to cross the abdominal wall 84, as shown in FIG. 15. After the surgeon is comfortable with the state of the abdomen, she may remove the endoscope 90 from the trocar 82 and load the shaft 20 onto the endoscope 90, e.g., utilizing the clip 30 (e.g., as shown in FIG. 1A). Next, the surgeon may adjust the depth of the stop 41, e.g., with the thumb wheel 44. Next, she may shroud the tool head 60 with the shroud 70, and introduce the entire assembly into the abdomen, e.g., until the stop 41 hits abdominal tissue or the trocar 82. After the apparatus 10a is in the abdomen, the shroud 70 may release and the surgeon may rotate and/or otherwise manipulate the tool head 60 into the field of view of the endoscope 90. Subsequently, the control shaft 80 may be inserted into the tool head 60 in the field of view of the endoscope 90.

Turning to FIG. 8, the apparatus 10b may be used generally in a similar manner. Unlike the previous embodiments, the housing 50b may be rotated, e.g., by actuation of a thumb slide 46 around hinge 21 and/or the tool head 60 may be rotated, e.g., by actuation of trigger 42. When the operator actuates the thumb slide 46 and/or trigger 41, the tool head 60 may be directed to a desired orientation, e.g., between a substantially coaxial-to-the-endoscope state 12 as shown in FIG. 8A, a substantially perpendicular-to-the-endoscope state 14 as shown in FIG. 8B, or a substantially parallel-to-the-endoscope state 16 as shown in FIG. 8C. The freedom to move between all three positions (or anywhere in between) may facilitate use by the surgeon, e.g., to accommodate the introduction method of apparatus 10b into the patient's body, whether with a trocar 82 or without to cross the abdominal wall 84, and/or to facilitate adaptation to variable anatomy within the abdomen.

Turning to FIG. 9, as described above, a carrier tool 110 may be used that includes a housing 50 capable of holding multiple tool heads 60, e.g., in a rail or spline 56. The surgeon may desire to have multiple tool heads available together within the surgical space, e.g., to reduce time in the operating room, e.g., reducing the exchange time to change tool heads on the control shaft of a surgical tool being used during the procedure. A single rail or spline 56 may hold all or some of the necessary tools required to complete a surgical procedure.

For example, an exemplary procedure that includes multiple tools is gall bladder removal. Such a procedure may involve using multiple end effectors, such as those shown on the tool heads 100-170 in FIG. 16, namely a serrated grasper 100, an atraumatic grasper 108, a dissector 130, a clip applier 140, a scissor 140 a monopolar hook-cautery tool 160, and/or a bipolar cut-cautery tool 170. Carrier tools, such as tool 110, may allow all or some of these modular tool heads to be introduced together and be readily available to avoid having to remove the carrier tool and/or endoscope in order to exchange one tool head for another, which may reduce the duration of the procedure.

Optionally, the carrier tool 110 and housing 50 holding multiple tool heads 60 may be attached to the endoscope 90 using via various mechanisms and methods. For example, the carrier tool 110 may include clip elements (not shown) that allow the carrier tool 110 to be attached laterally onto an endoscope 90, or slid axially over the endoscope 90, e.g., similar to the embodiments of FIGS. 1 and 2. As described elsewhere herein, the selected housing 50 may be straight or curved, e.g., as shown in FIGS. 10A and 10B, to accommodate different levels of space availability and/or space geometry within the surgical space. If the housing 50 includes a conveyer belt 58, as shown in FIG. 10B, the conveyor belt 58 may be actuated from outside the patient's body to present the desired tool head 60 within the field of view of the surgeon and move the other tools out of the field of view.

Turning to FIGS. 11A-12B, alternative controlled arrays of tool heads 60 may be provided to allow multiple tool heads 60 to be introduced together. As explained above, these arrays may resiliently expand when they are advanced from the housing 50. The expansion of the array may allow the surgeon to orient a desired tool head 60 within the field of view of the endoscope 90 to facilitate mating the desired tool head 60 with the control shaft 80.

Turning to FIG. 13, an alternative method is shown for coupling a tool head 60 to a control shaft 80, e.g., using a wire-based connection between the control shaft 80 and the carrier tool 10. First, a distal end of a wire 74 may be introduced into the abdomen or other surgical space, e.g., through or adjacent a control shaft 80 and/or a first port (not shown), and a snare 76 may be introduced independently into the surgical space, e.g., adjacent the endoscope 90 and/or a second port (also not shown), to snare the distal end of the wire 74. The snare 76 may be withdrawn to pull the wire 74 out of the surgical space, and then the wire 74 may be secured to the desired tool head 60. The tool head 60 may then be introduced into the surgical space using a flexible introduction tube 71 or other carrier tool via the second port (not shown) and the wire 74 may be manipulated to guide the tube 71 and tool head 60 to the control shaft 80. Thus, the wire rail system may facilitate mating the control shaft 80 and the tool head 60. Exemplary apparatus and methods for snaring and manipulating wires are disclosed in U.S. Pat. No. 6,379,319, the entire disclosure of which is expressly incorporated by reference herein.

Turning to FIG. 14, an alternative method is shown in which the carrier tool 10 is introduced through a trocar 82 at a different point in the abdominal wall 84 than the endoscope 90. One advantage of such a procedure is that it may provide more degrees of motion freedom.

Figure 17:
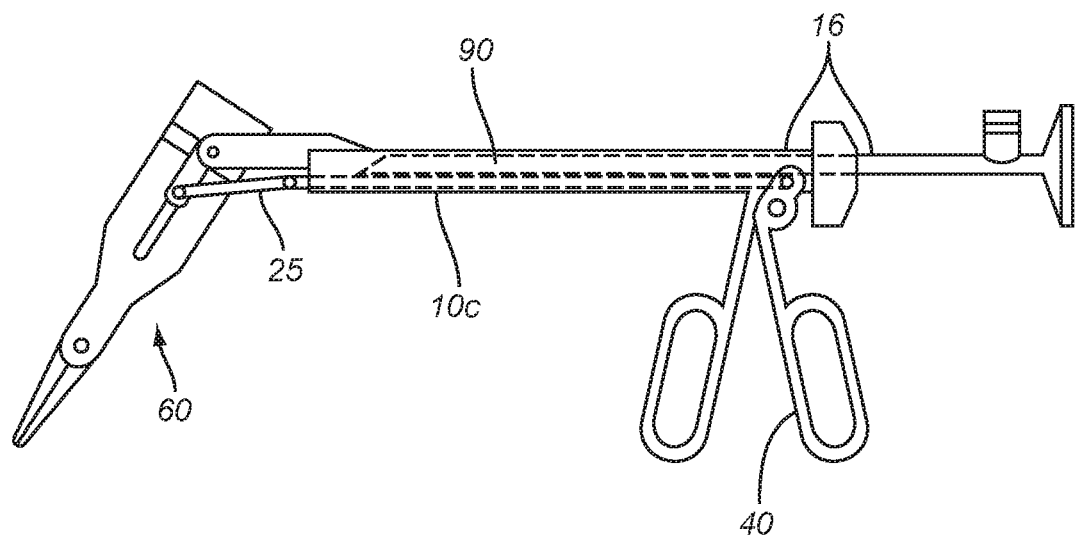
FIG. 17 is a side view of another embodiment of a carrier tool coupled to an endoscope for introducing a tool head into a surgical space, the carrier tool including a plurality of linkages for controlling an orientation of the tool head.

Turning to FIG. 17, another exemplary embodiment of a tool carrier or introduction apparatus 10c (which may be any of the embodiments herein) is shown, which may allow a tool head 60 carried thereby to be actively positioned using an actuating handle 40 connected by a series of linkages 25. This introduction apparatus 10c may be placed over an endoscope 90, e.g., as shown above, or placed separate from the endoscope 90 in a parallel manner 16 through a location near the endoscope 90 such as the umbilicus or through an alternative port site (not shown) away from that of the endoscope 90.

Figure 18:
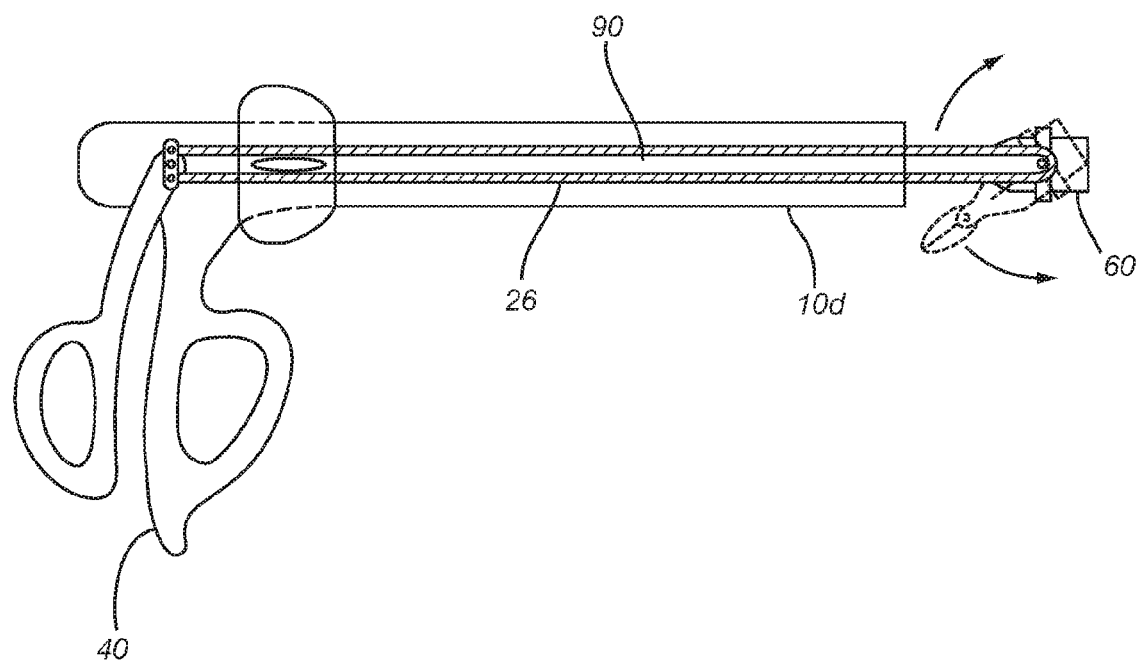
FIG. 18 is a cross-sectional side view of an alternative embodiment of a carrier tool coupled to an endoscope for introducing a tool head into a surgical space, the carrier tool including one or more control wires or cables for controlling an orientation of the tool head.

As shown in FIG. 18, another embodiment of a tool carrier 10d is shown that includes an alternative embodiment of an actuator 26. The actuator 26 may allow repositioning of the tool head, e.g., using tension members such as one or more wires or cords, e.g., rather than the linkages 25 shown in FIG. 17 and described above.

Turning to FIGS. 19A and 19B, an alternative embodiment of a tool carrier 10e is shown that include one or more rotating tooth features or hinges 55, e.g., that correspond to a groove 63 in a locking ring 62 of the tool head 60. As shown, two circular features 55 may be provided that are offset from one another such that axial movement of at least one of the features 55 relative to the other, e.g., by actuating rod 55a relative to the housing 50, rotates the tool head 60, e.g., between the orientations shown in FIGS. 19A and 19B.

Turning to FIGS. 20 and 20B, yet another embodiment of a mechanism is shown that may be provided on a tool carrier or introduction apparatus 10f for carrying a tool head 60 and/or adjusted an orientation of the tool head 60. For example, to allow the tool head 60 to be positioned substantially in-line with the shaft 20 of the introduction apparatus 10f, a solid linkage 25a may be provided such that, at complete rotation, the components of the solid linkage 25a do not interfere with each other while maintaining a relatively small cross-sectional envelope.

Figure 21A:
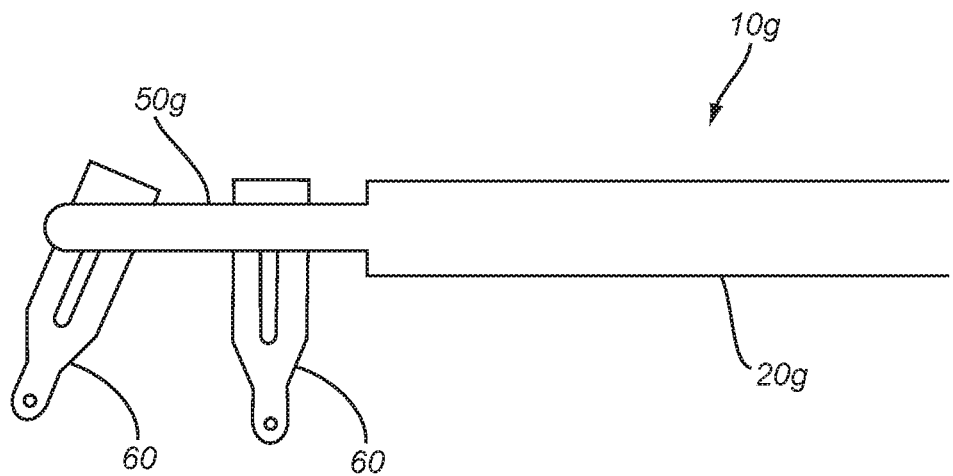
FIGS. 21A and 21B are perspective and side views, respectively, of an introducer tube or tool carrier including a pair of elongate members defining a track for receiving a plurality of tool heads inserted through the introducer tube onto the track.
Figure 21B:
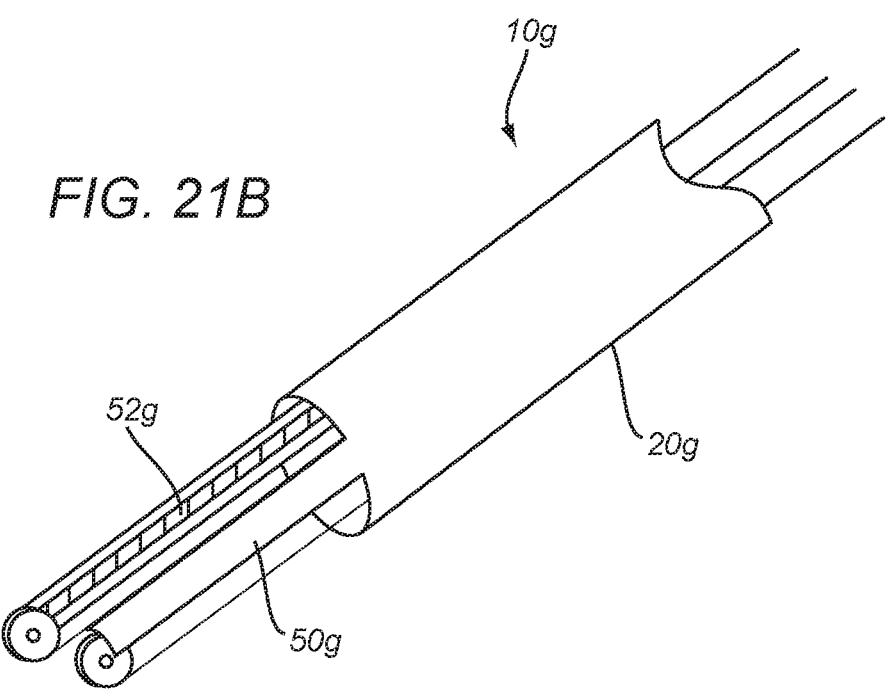

Turning to FIGS. 21A and 21B, another exemplary embodiment of a tool carrier 10g is shown that includes an elongate introducer tube 20g including a distal end size for introduction into a surgical space, e.g., via a trocar or port (not shown). A pair of spaced apart elongate rails 50g extend from the distal end of the introducer tube 20g, thereby providing a track 52g for receiving a plurality of tool heads 60. One or more tool heads 60 may be introduced into the introducer tube 20g, e.g., via an insertion tool (not shown) or simply by sliding the tool head(s) 60 through a bore of the introducer tube 20g such that features on the tool heads 60 are slidably captured within the track 52g and are exposed beyond the introducer tube 20g. Thus, tool heads 60 may be dropped down the introducer tube 20g and held by the track 52g to allow a control shaft (not shown) to connect to a desired tool head 60 carried by the track 52g. Optionally, the tool heads 60 may be coupled to cables, belts, or another mechanical features (not shown), e.g., to facilitate insertion or removal of the tool heads 60 from the track 52g and/or introducer tube 20g.

Figure 22:
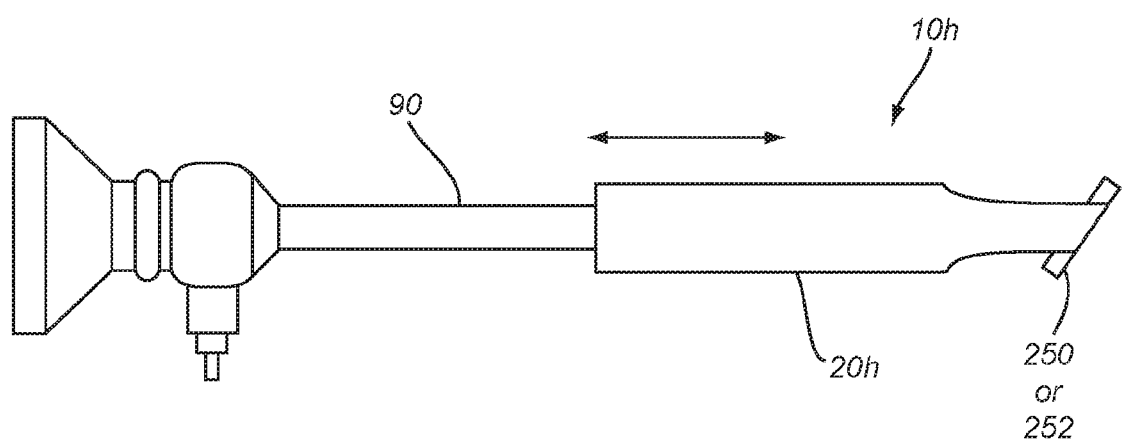
FIG. 22 is a side view of another embodiment of a tool carrier including a sleeve that may be directed over a distal end of an endoscope and an introduction feature on a distal end of the sleeve for carrying a tool head.

Turning to FIG. 22, another embodiment of a tool carrier or introduction apparatus 10h is shown that may include a tube shaft 20h that slidably fits over an endoscope 90. This tube shaft 20h may be slid forwards or backwards along the endoscope 90 during use, e.g., to adjust the relative distance between the endoscope 90 and a tool head 60 (not shown) carried on an introduction feature 250, 252 on a distal end of the tube shaft 20h. Once the tool head 60 is removed from introduction feature of the introduction apparatus 10h, e.g., after being secured to a control shaft (not shown), the tube shaft 20h may be retracted so that the endoscope 90 has full visibility with minimal or no obstruction from the introduction feature. The distal end of the tube shaft 20h may include one or more introduction features 250, e.g., an introduction ring 252, that are sized to capture a tool head 60 and pass over the distal end of the endoscope 90 when the tube shaft 20h is retracted after locking the tool head 60 onto a control shaft. The introduction ring 252 may be static or movable relative to the tube shaft 20h, as described in the various embodiments below.

Figure 23:
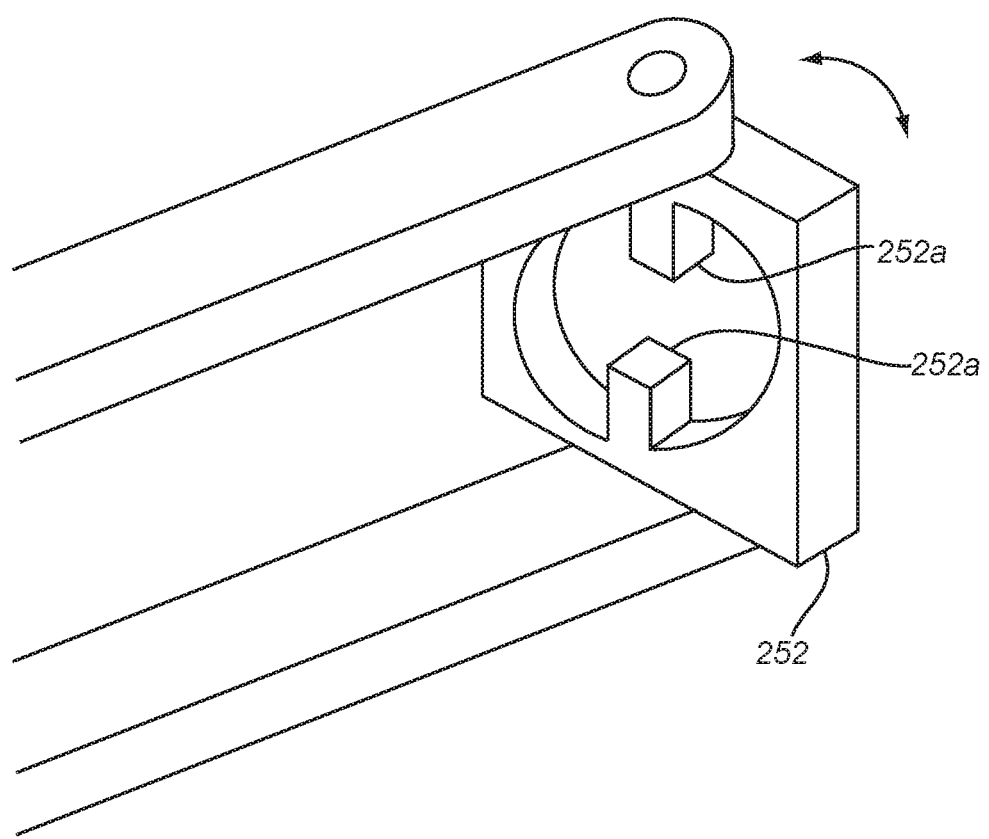

For example, FIG. 23 shows an exemplary embodiment of an introduction feature or ring 252 that may be carried by the tube shaft 20h (not shown). As shown, the introduction ring 252 includes a pair of opposing tines, tabs, or other locking features 252a that may be received in corresponding features on a tool head, such as the grooves 63a, 63b of the tool head 60 shown in FIG. 30 or other embodiments herein. Alternatively, the introduction ring 252 may include one, three, four, or more locking features (not shown) spaced apart from one another extending into or otherwise around an aperture through the introduction ring 252 through which the tool head 60 may be received.

Figure 30:
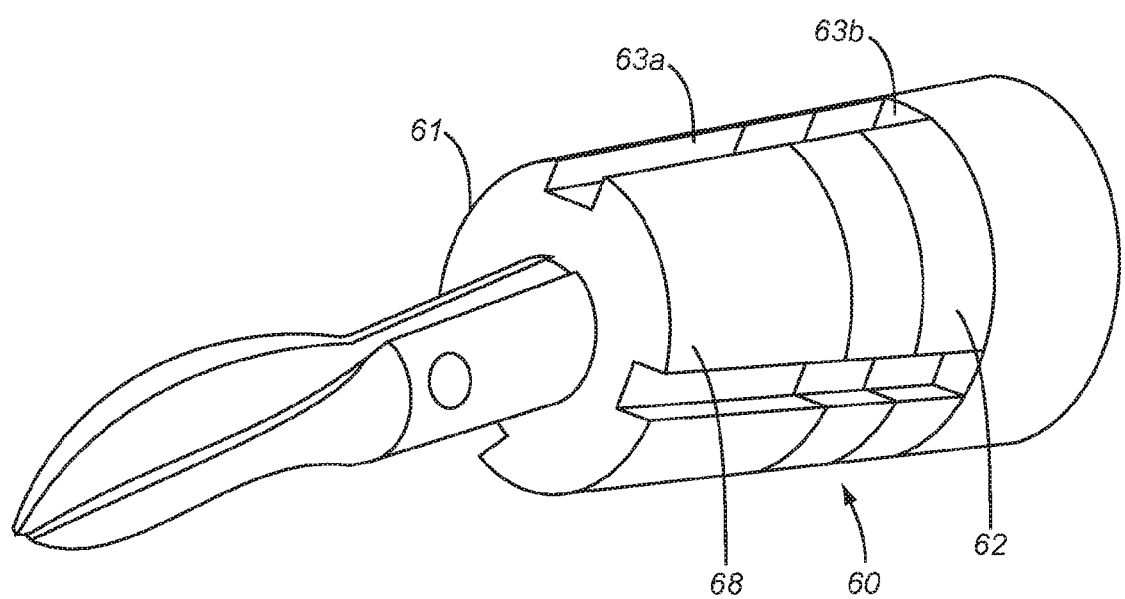
FIG. 30 is a perspective view of an exemplary embodiment of a modular tool head having a tapered shape.

In an exemplary embodiment, the introduction ring 252 and/or locking features may have a length similar to or less than a locking element on a tool head, e.g., shorter than a rotating locking ring 62 of the tool head 60 shown in FIG. 30, such that the locking features do not interfere with rotation of the locking ring 62 relative to a housing 68 or other components of the tool head 60, similar to other embodiments herein. For example, the width of the locking features 252a may allow the locking features 252a to slide into the grooves 63a, 63b of the tool head 60 of FIG. 30 (without being removable other than from the ends of the grooves 63a), and the length may accommodate the locking features 252a being received in the grooves 63b without impacting the ability of the locking ring 62 to rotate relative to the housing 68.

The introduction ring 252 may be passively mobile, e.g., may freely pivot about an axis transverse to the longitudinal axis of the tube shaft 20h, e.g., accommodating multiple angles of entry. Thus, the introduction ring 252 may carry a tool head 60 (not shown) such the tool head 60 may rotate freely to accommodate aligning a control shaft with the tool head 60. The introduction ring 252 may also freely rotate to allow the introduction ring 252 to pass over the distal end of the endoscope 90 when the tube shaft 20h is retracted after removing the tool head 60.

Figure 24A:
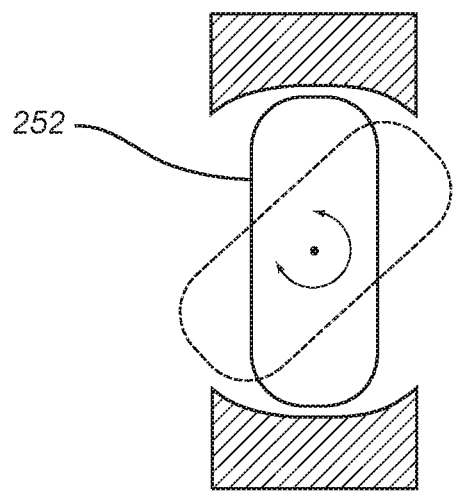
FIGS. 24A and 24B show another embodiment of an introduction ring that may be carried by a tube shaft.
Figure 24B:
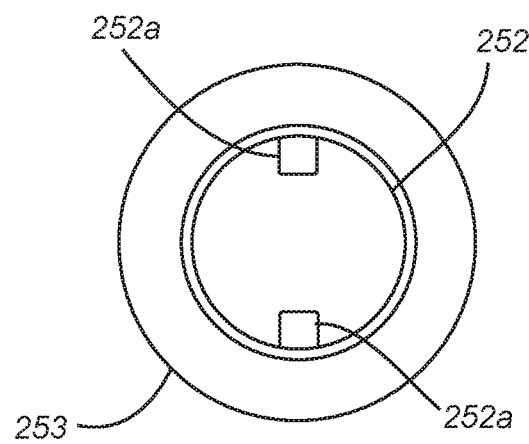

In another embodiment, shown in FIGS. 24A and 24B, an introduction ring 252, generally similar to the embodiment of FIG. 23, may be configured to pivot about at least one axis, e.g., to aid with alignment of the tool head and control shaft (not shown). Alternatively, the introduction ring 252 may also be held within a spherical bearing surface 253 that allows the introduction ring 252 to move freely in any direction rather than pivoting about a single axis.

Figure 25A:
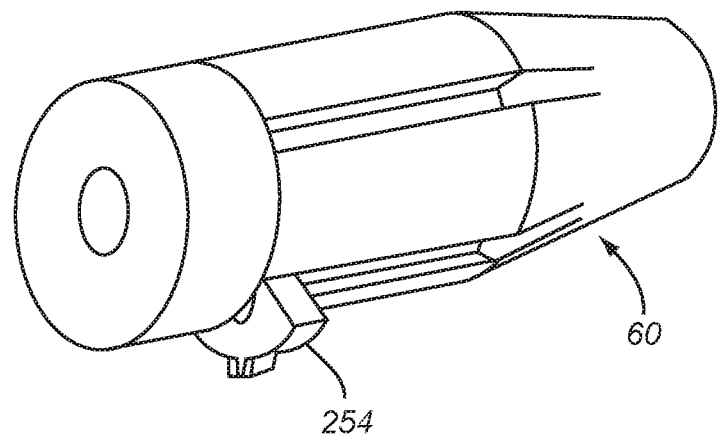
FIGS. 25A and 25B are perspective and cross-sectional views of another embodiment of an introduction feature for carrying a tool head.
Figure 25B:
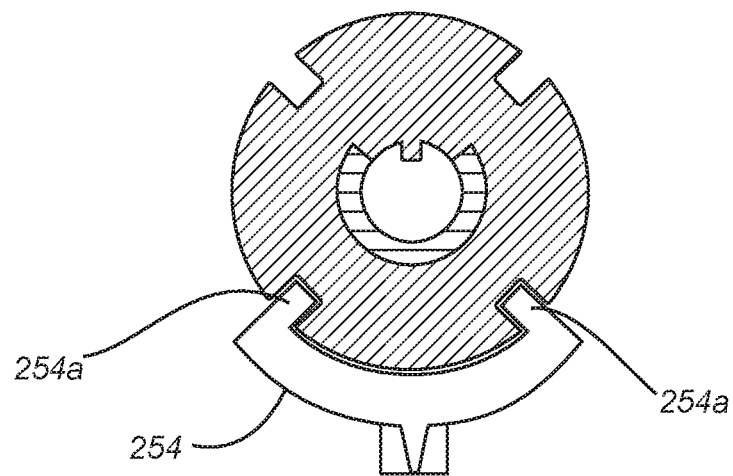

Turning to FIGS. 25A and 25B, another embodiment of an introduction feature or clip 254 is shown that includes two adjacent alignment and locking features 254a for releasably securing a tool head 60 to the introduction feature 254. Alternatively, the introduction feature 254 may also encompass a single locking feature, which may provide multiple points of contact on the outside of the tool head 60.

Figure 26A:
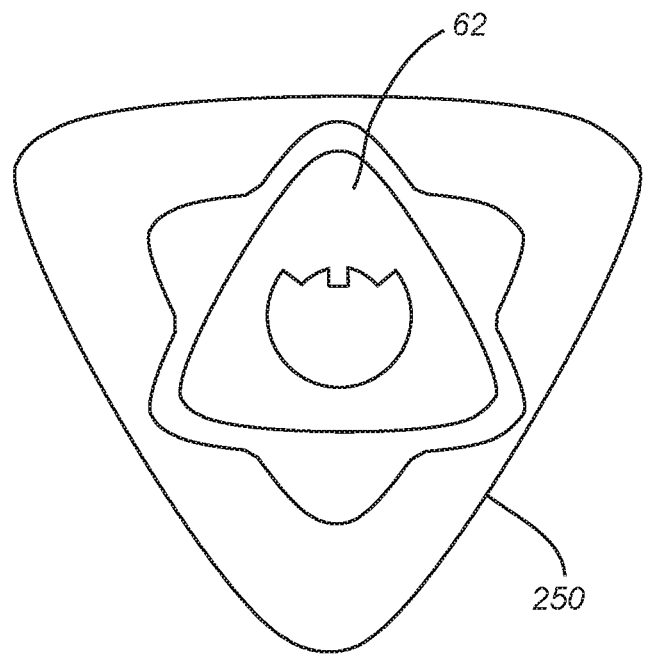
FIGS. 26A and 26B are cross-sectional views of alternative embodiments of introduction rings that may be provided on a tool head carried by corresponding introduction features that may be provided on a tool carrier.
Figure 26B:
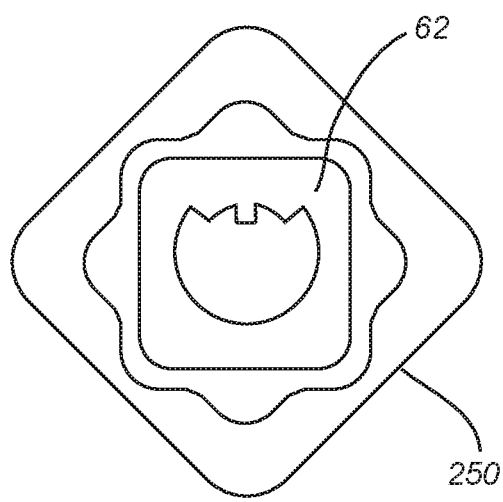

FIGS. 26A and 26B show alternative embodiments of introduction features 250 and corresponding locking rings 62 that may be provided without slots and/or as a non-circular shape. It will be appreciated that any shape may be provided to interface the introduction feature 250 to a similarly shaped locking ring 62 of a tool head, including cams, polygons, eccentrics, etc. Optionally, the introduction feature 250 may also encompass extra openings (not shown) to engage mating features on the locking ring 62.

Figure 27:
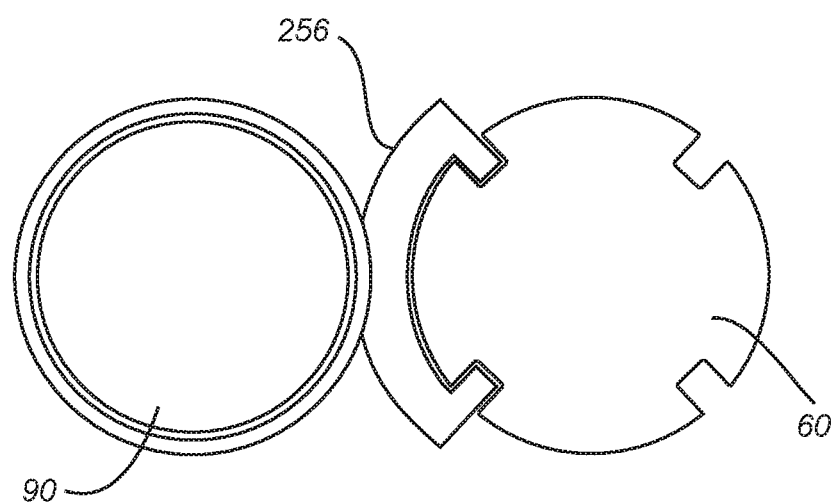

Turning to FIG. 27, another embodiment of an introduction feature or ring 256 is shown. The introduction ring 256 may allow a tool head 60 to be placed through a trocar or other port (not shown), substantially in parallel with a standard endoscope 90. As shown, the introduction ring 256 is a "C" shaped clip extending from a sleeve coupled to the endoscope 90 such that the sleeve is fixed or slidable relative to the endoscope 90. The introduction ring 256 may have a one quarter pivot in one axis, e.g., to facilitate aligning a tool head 60 carried by the introduction ring 256 with a control shaft (not shown). Because the introduction ring 256 includes fingers or prongs that are captured in or otherwise engaged to mating features in the tool head 60, e.g., to locking ring (not shown), the height or profile of the introduction ring 256 relative to the endoscope 90 may be minimized.

Figure 28A:
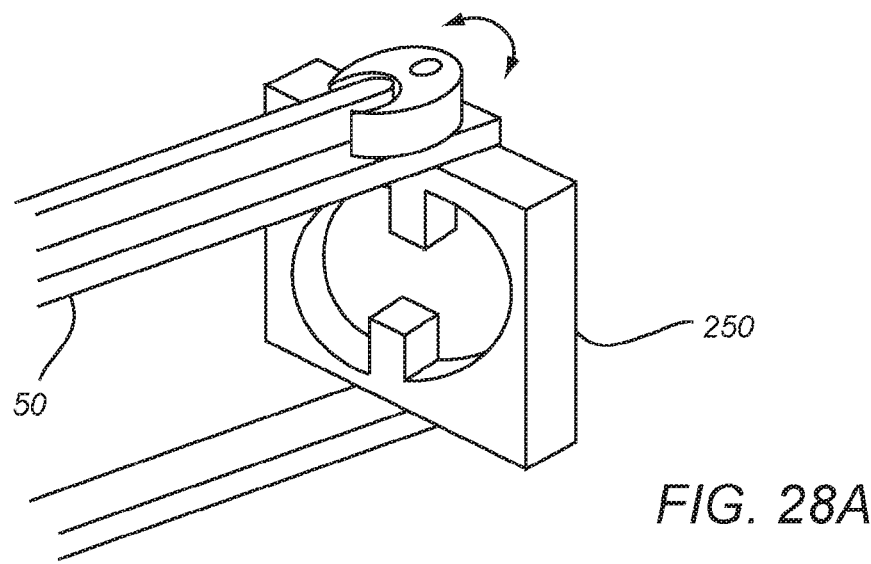
Figure 28B:
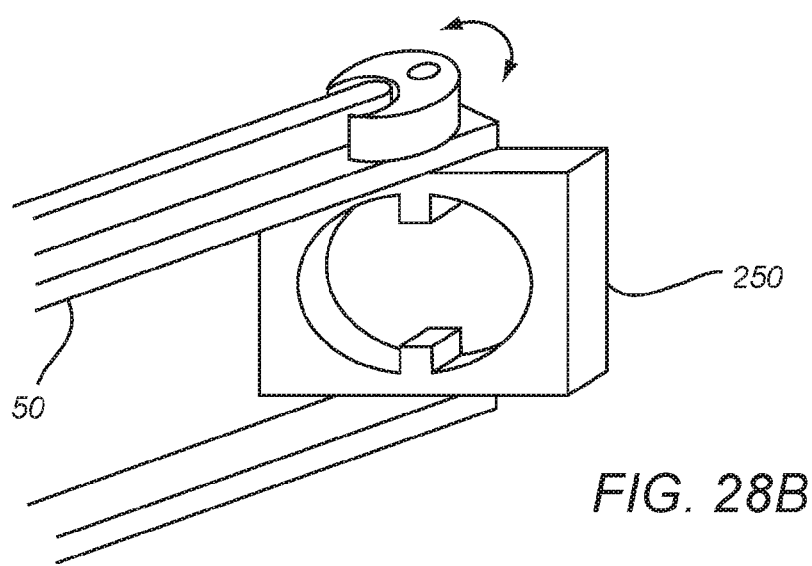
Figure 28C:
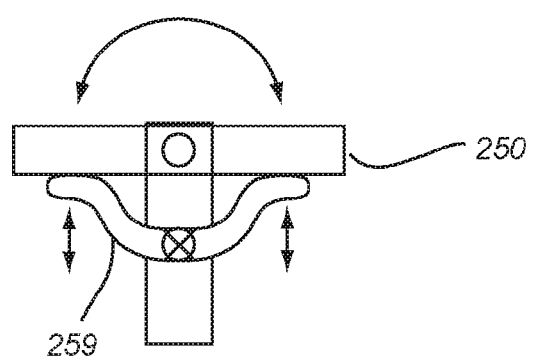
FIG. 28C is a top view of the introduction ring of FIGS. 28A and 28B showing an exemplary biasing mechanism.
Figure 28D:
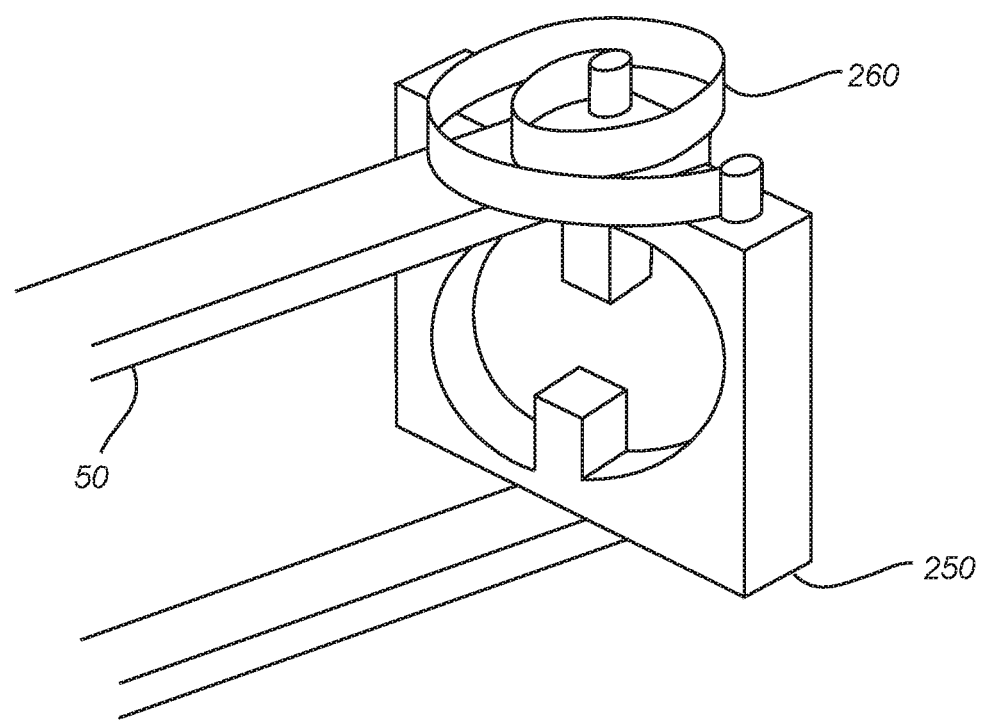
FIG. 28D is a perspective view of the introduction ring of FIGS. 28A and 28B with a cover removed to show another exemplary biasing mechanism.

Turning to FIGS. 28A-28D, additional embodiments of an introduction feature or ring 250 are shown that include a spring element coupled to the introduction feature 250 for biasing the introduction feature 250 towards a neutral position but allowing the introduction feature 250 to rotate slightly, e.g., to facilitate aligning a control shaft (not shown) with the tool head 60. In exemplary embodiments, the spring element 258 may be a flat spring 259, as shown in FIG. 28C, a clock spring 260, as shown in FIG. 28D, or the compliance may be designed into a tool housing structure 50 of the introduction ring 250. Once the tool head 60 has been removed or replaced, the introduction feature 250 may automatically return to its neutral position, e.g., to facilitate retracting the introduction feature 250 over the endoscope 90.

Figure 29A:
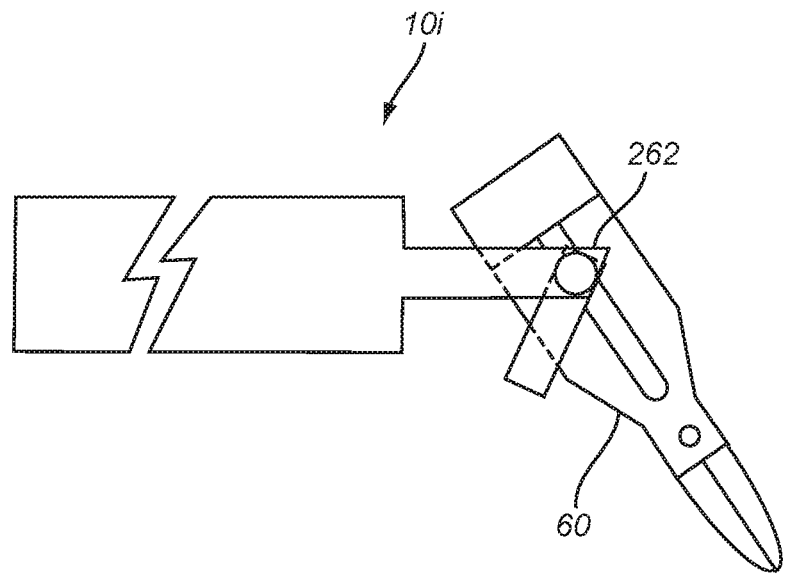
FIG. 29A is a side view of another embodiment of a tool carrier and introduction feature carrying a tool head.
Figure 29B:
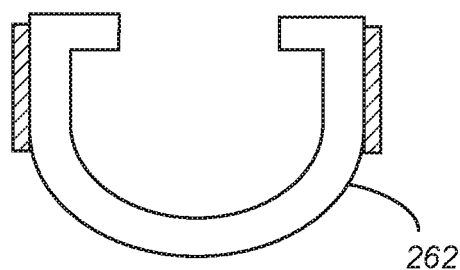
FIG. 29B is a side view of the introduction feature of FIG. 29A.

Turning to FIGS. 29A and 29B, another embodiment of a carrier tool 10i is shown including a introduction feature 262 that includes a generally "U" shaped member for capturing a tool head 60. The introduction feature 262 may be designed to allow some rotation while the tool head 60 is locked inside of it, e.g., about a single transverse axis. For example, the introduction ring 262 or the introduction apparatus 10i may limit rotation of the tool head 60 locked thereto to allow for some angular positioning. The introduction ring 262 may not completely surround the tool head 60, but may only extend less than one hundred eighty degrees) (180°) around the tool head 60, e.g., if features on the introduction ring 262 are engaged with mating features on the tool head 60.

Turning to FIG. 30, an exemplary embodiment of a tool head 60 is shown that includes a non-tapered or blunt front surface 61, e.g., which may reduce the likelihood of wedging the tool head 60 into the interior of a tool carrier or introduction apparatus (not shown), which may be any of the embodiments herein.

Figure 31B:
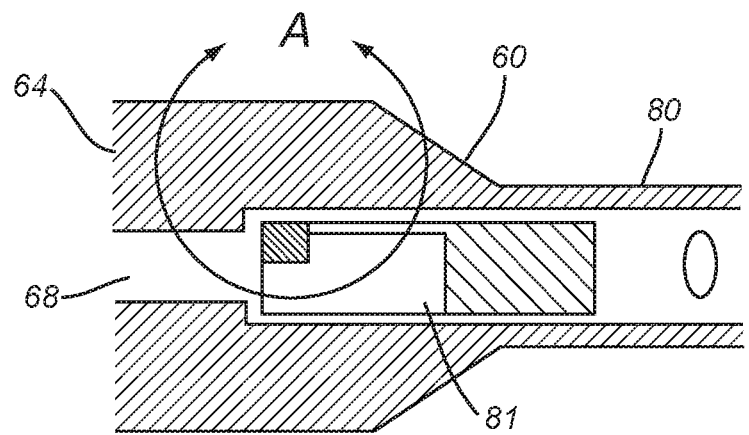
FIGS. 31A and 31B are details of a detent that may be engaged between a modular tool head and a control shaft of a surgical tool to prevent premature actuation of jaws on the tool head during connection of the tool head to the control shaft.
Figure 31A:
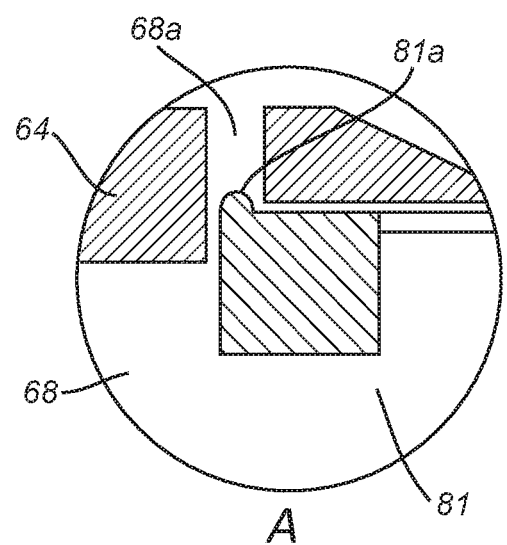

Turning to FIGS. 31A and 31B, to prevent jaws 64 of a tool head 60 from opening prematurely due to friction between the control shaft 80 and an actuating link 81 of the tool head 60, e.g., when the tool head 60 is coupled to the control shaft 80, a detent or similar feature may be provided between the actuating link 81 and the housing 68 of the tool head 60. For example, in one embodiment, a male detent feature 81a may be provided on the outside surface of the actuating link 81, which may correspond to a hole or recess 68a in the internal surface of the housing 68. When the jaws 64 are in the alignment position (i.e., the predetermined position for coupling/decoupling the tool head 60 to the control shaft 80, as described elsewhere herein), the control shaft 80 may be inserted sufficiently into the housing 68 such that the male detent 81a sits in the hole or recess 68a of the housing 68. In order for the jaws 64 to be subsequently opened, the actuating link 81 must be pushed axially with a force greater than the frictional forces between the control shaft 80 and the actuating link 81 encountered during insertion and coupling.

Figure 32A:
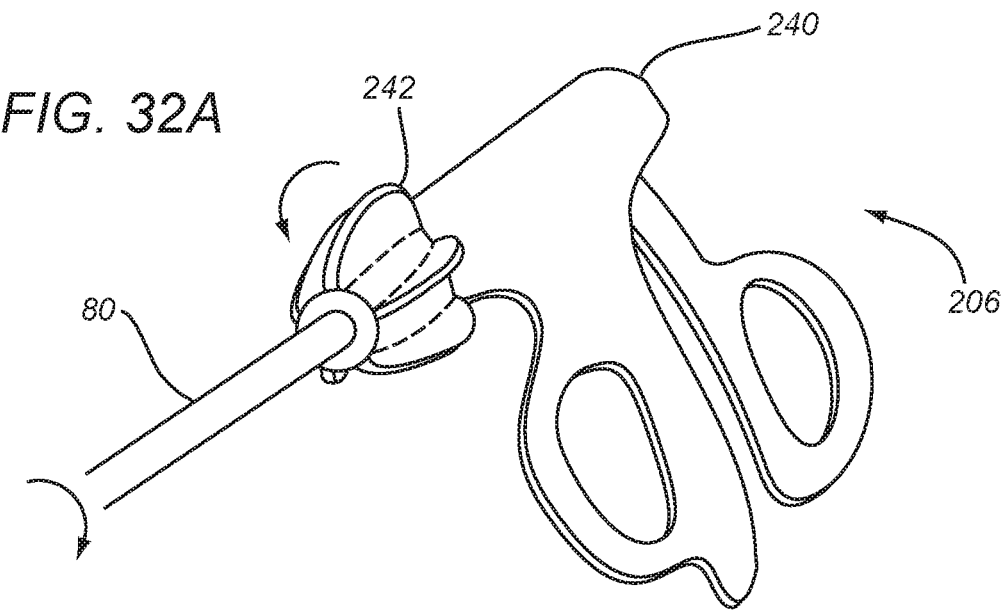
FIG. 32A shows a clutch apparatus that may be provided on a surgical tool including a control shaft to limit torsional forces applied to the control shaft when a modular tool head is attached to or removed from the control shaft.
Figure 32B:
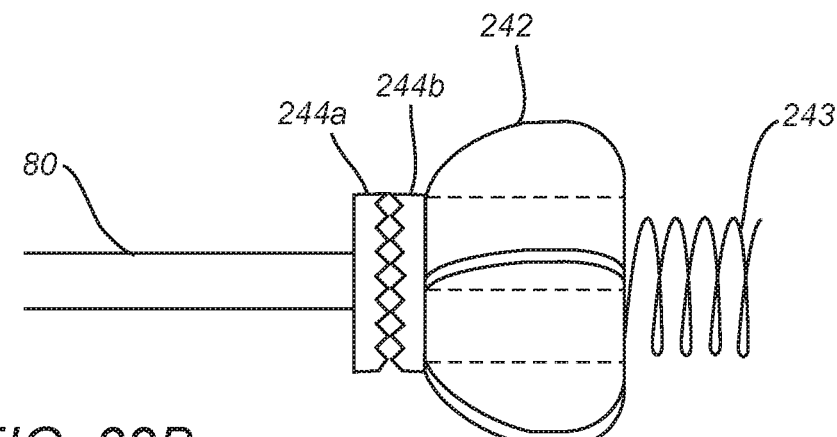
FIGS. 32B and 32C are cross-sectional details of the clutch apparatus of FIG. 32A.
Figure 32C:
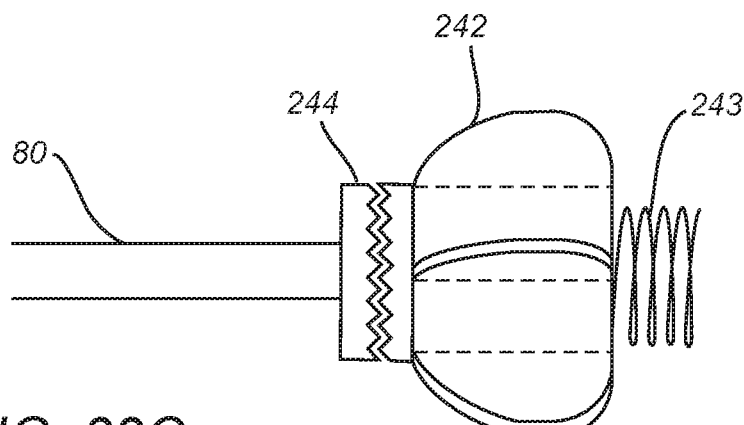

Turning to FIGS. 32A-32C, in any of the embodiments herein, a surgical tool 206 may be provided that includes a thumbwheel 242 and clutch 243 on a handle set 240, e.g., to prevent damage to the tool 206 through use, e.g., when a tool head 60 is being coupled to a control shaft 80 of the tool 206. For example, the thumbwheel 242 may allow a maximum torsional load allowed on a control shaft 80 to be set from the thumbwheel 242. If a torsional force greater than that required to lock or unlock the tool head 60 to/from the control shaft 80 is exerted, the clutch 243 may "release" enough to prevent the torsional load from increasing. Mechanical elements such as interlocking teeth 244 may be used as a clutch 243 mechanism whereby one or more toothed element 244a is elastically sprung against the other tooth element 244b, as shown in FIGS. 32B and 32C. As the thumb wheel 242 is rotated with a sufficient torsional load, the sprung tooth element 244a is forced outward allowing it to slide over the other tooth element 244b. This same effect may be achieved using purely frictional elements such as a rubber fitting 245 between the control shaft 80 and the thumb wheel 242, e.g., where the static friction created by the rubber is slightly greater than the maximum force required to lock or unlock the tool head 60.

Figure 33A:
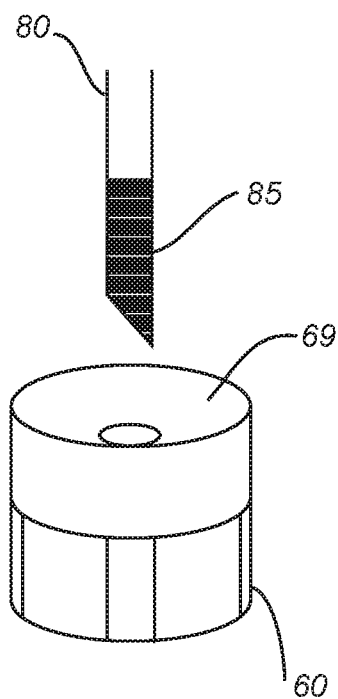
FIGS. 33A-33C are details of visual indicators that may be provided on a control shaft of a surgical tool to provide visual confirmation when a modular tool head has been sufficiently received on the control shaft.
Figure 33B:
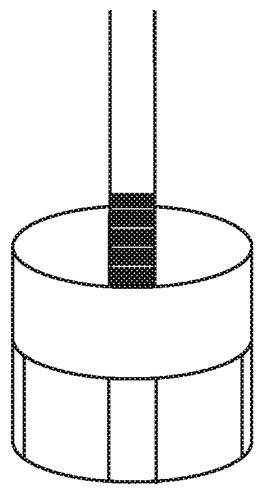
Figure 33C:
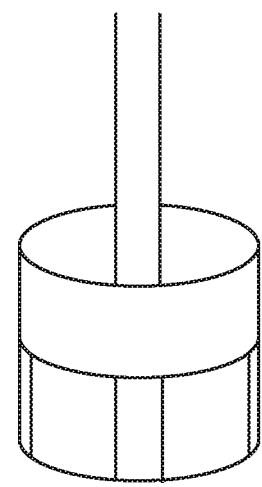

Various indicators may be provided on components of the apparatus described herein, for example, to provide feedback, visual, audible, and the like, that components are aligned with one another in a desired manner, e.g., when attaching or separating the components. For example, turning to FIGS. 33A-33C, to provide indication that an outer cannular tube or shaft 80 and inner active shaft 83 are fully inserted into a tool head 60 being coupled to a tool, such as the tool 206 shown in FIG. 32A, a visual indicator or marker 85 may be provided on the cannular shaft 80. As best seen in FIG. 33A, the end of the cannular shaft 80 may be colored in a band that ends at a distance corresponding to the proper insertion depth when inserted into a guide cap 69 on the tool head 60. When fully inserted into the tool head 60, the marking 85 is no longer visible, giving feedback that the proper depth has been achieved, as shown in FIG. 33C. Alternatively, the cannular shaft 80 may be marked where the section left unmarked is at the end.

Figure 34A:
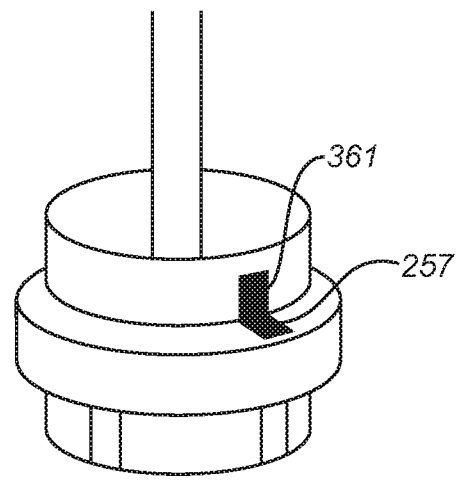
FIGS. 34A and 34B are details of visual indicators that may be provided on a modular tool head and an introduction ring of a carrier tool to provide visual confirmation when the tool head is rotatably aligned with the introduction ring in a predetermined orientation.
Figure 34B:
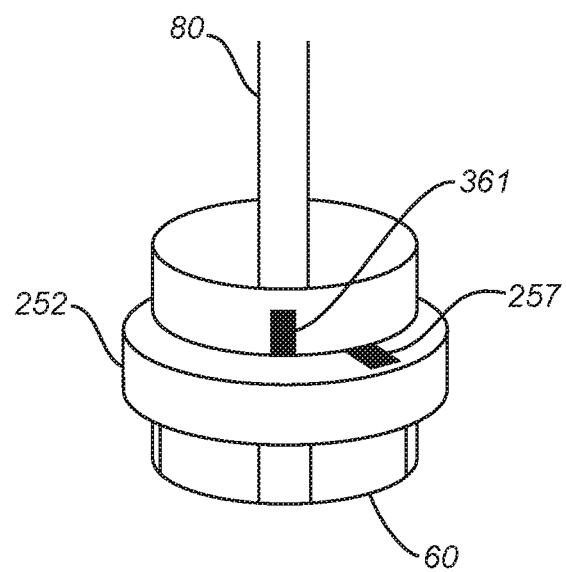

Turning to FIGS. 34A and 34B, to provide an indication of the relative rotation of a tool head 60 and an introduction ring 252, a visual indicator or marker 361 may be provided on the tool head 60 and another visual indicator or marker 257 may be provided on the introduction ring 252. The indicators 361, 252 may be colored or etched on the surface of adjacent components of the tool head 60 and introduction ring 252. When rotated to the unlocked or locked position, the indicators 361, 252 may become aligned (as shown in FIG. 34A) or misaligned (as shown in FIG. 34B), thereby giving visual confirmation that the tool head 60 is locked or unlocked from the introduction ring 252.

Figure 35A:
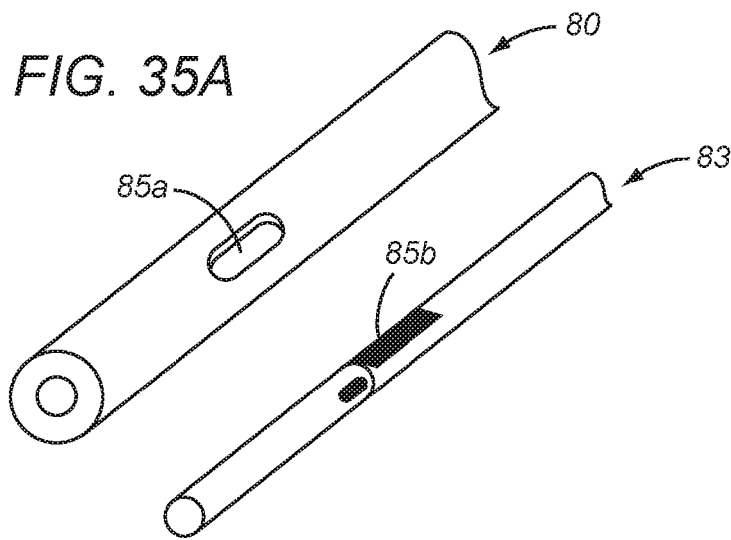
FIG. 35A is an exploded perspective view of a control shaft of a surgical tool that includes an outer shaft and an inner shaft including features that provide a visual indication when the inner shaft is rotationally aligned within the outer shaft.
Figure 35B:
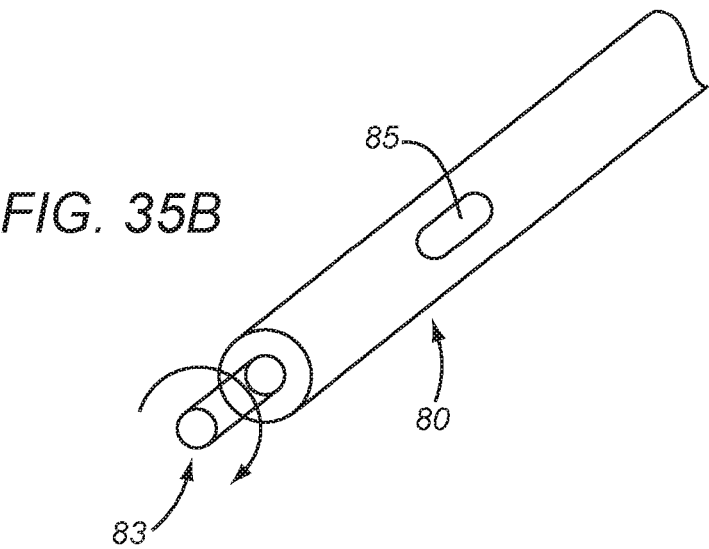
FIGS. 35B and 35C are perspective views of the assembled outer and inner shafts, showing the features misaligned and aligned with one another, respectively.
Figure 35C:
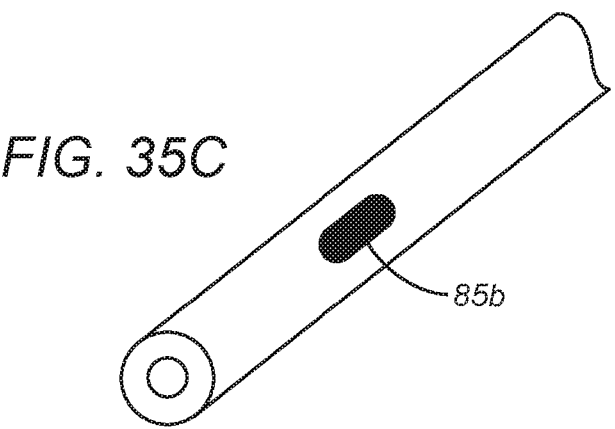

Turning to FIGS. 35A-35C, to provide indication that a cannular shaft 80 and inner active shaft 83 of a surgical tool are rotationally aligned in their relative locked positions, a cut out or window 85a may be provided in the cannular shaft 80 while a corresponding colored or altered surface indicator or marker 85b may be provided on the active shaft 83 (e.g., through anodizing, etching, painting, and the like), as best seen in FIG. 35A. When properly aligned, as shown in FIG. 35C, the indicator 85b is visible through the window or cutout 85a, giving visual feedback on the relative shaft alignment. If the outer cannular shaft 80 and inner shaft 83 are out of rotational and/or axial alignment, the indicator 85b cannot be seen through the window 85a, as shown in FIG. 35B.

Figure 36A:
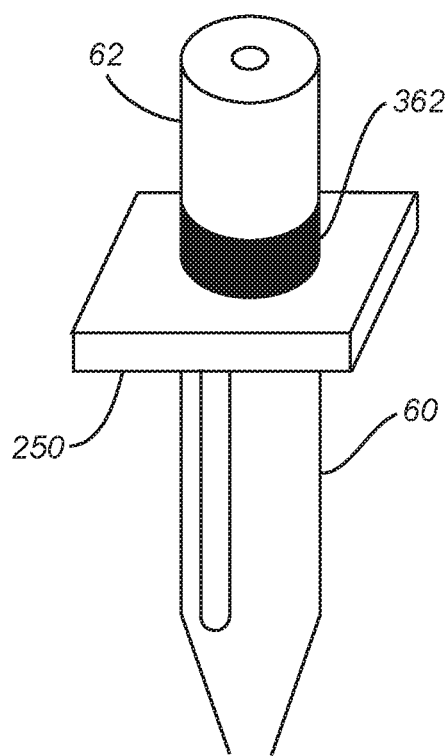
FIGS. 36A and 36B are perspective views of a modular tool head and an introduction feature of a tool head carrier including features (seen in FIG. 36A) that provide a visual indication when the tool head is fully inserted into the introduction feature (shown in FIG. 36B).
Figure 36B:
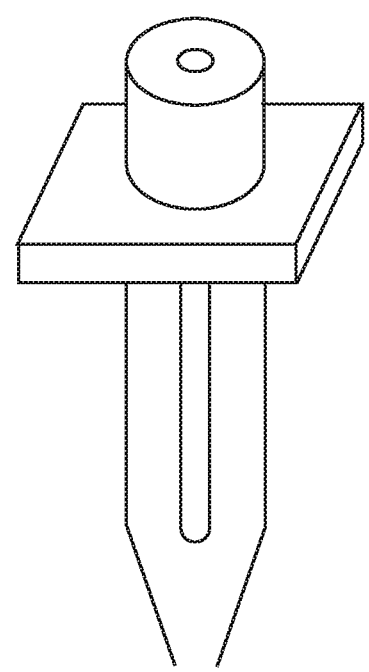

Turning to FIGS. 36A and 36B, to provide visual indication that a modular tool head 60 is fully inserted into an introduction feature 250 of a tool carrier (not shown), a locking ring 62 on the tool head 60 may be colored or otherwise altered to provide a marker 362, e.g., by some process such as anodizing, etching, painting, etc., as shown in FIG. 36A When the tool head 60 is fully inserted in the introduction feature 250, the marker 362 is no longer visible and the tool head 60 may then be rotated and locked into the introduction feature 250, as shown in FIG. 36B.

Figure 37A:
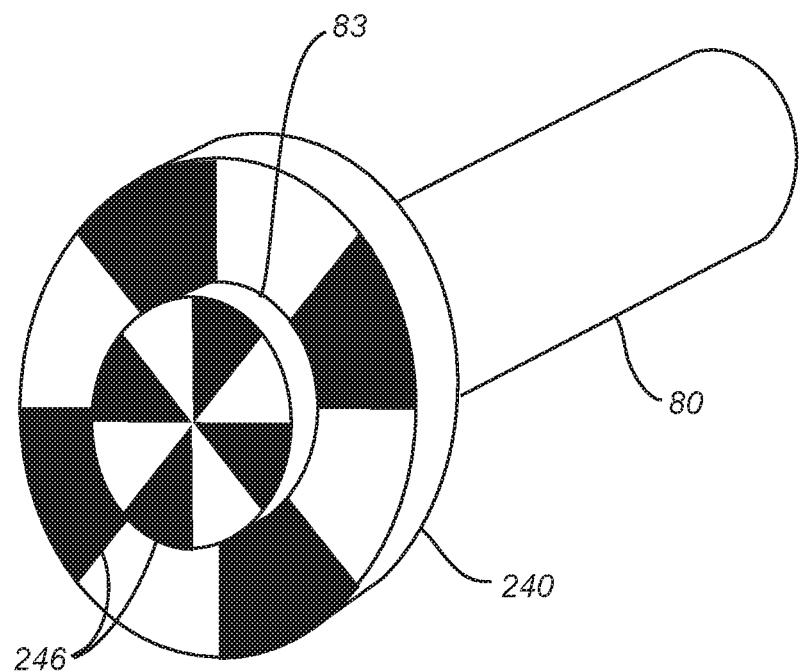
FIG. 37A is a perspective view of alignment features that may be provided on a handle of a surgical tool.
Figure 37B:
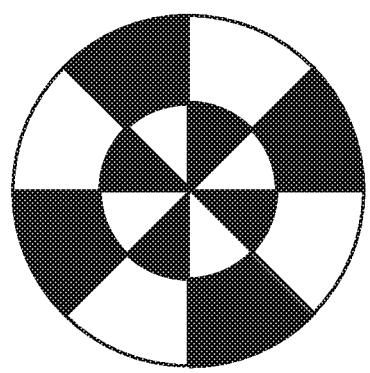
FIGS. 37B and 37C are end views showing the alignment features in and out of alignment with one another.
Figure 37C:
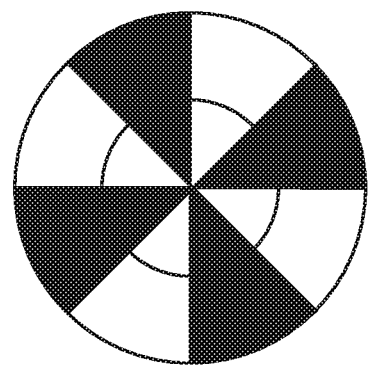

Turning to FIG. 37A, a rotation indicator 246 is shown that may be provided on the back of a handle set 240 of a surgical tool where one component of the indicator 246 is linked to an inner active shaft 83 of the tool and the other corresponds to an outer cannular shaft 80 of the tool. When the shafts 80, 83 are aligned in the proper rotational position relative to each other, the patterns of the indicator 246 also align, as shown in FIG. 37C, giving visual confirmation of the shaft alignment.

Turning to FIGS. 38A-38E, to prevent accidental rotation of a locking ring 62 of a modular tool head 60 and/or provide tactile feedback of the locked and unlocked positions, first and second detents 62a, 62b may be provided on the locking ring 62 that match up with a cut out section 68b of a housing 68 of the tool head 60. To allow for expansion and contraction of the locking ring 62, a small section 62c may be removed, e.g., at the exemplary locations shown in FIGS. 38A-38E.

Figure 38A:
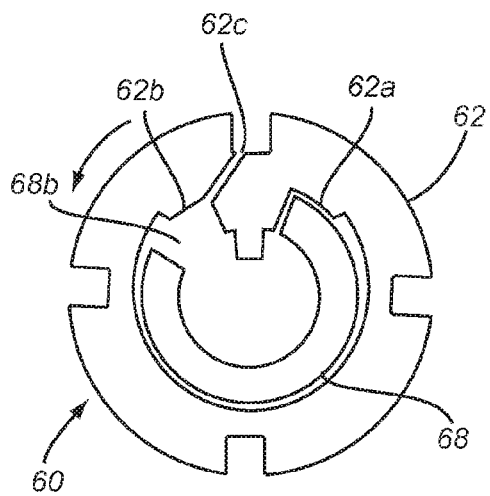
FIGS. 38A-38E are cross-sectional views of a modular tool head showing features in a locking ring to provide tactile feedback when the locking ring is in locked and unlocked positions.
Figure 38B:
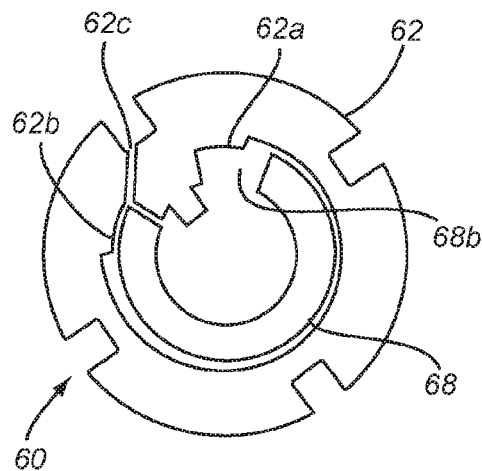
Figure 38C:
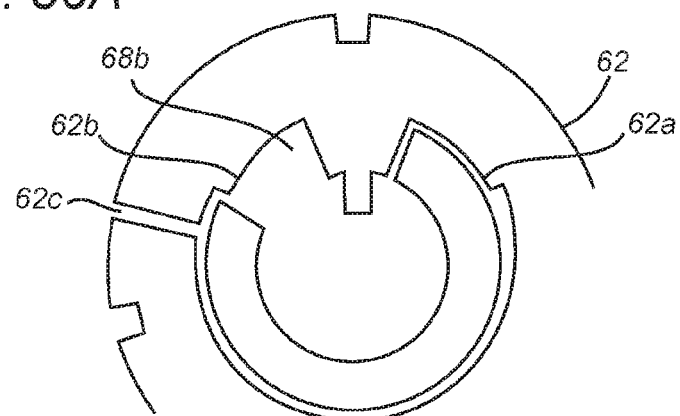
Figure 38D:
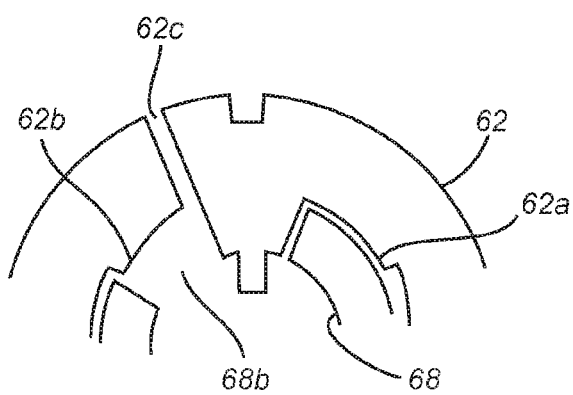
Figure 38E:
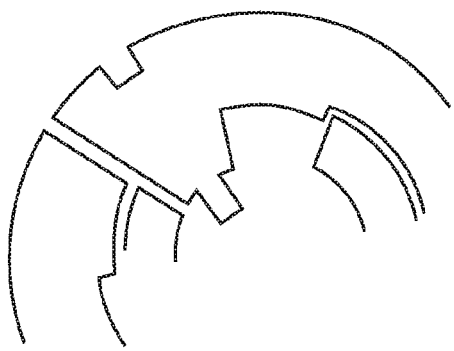

During use, as the locking ring 62 is rotated fully in a predetermined direction, e.g., a counterclockwise direction as shown in FIG. 38B, the first detent 62a falls into the cutout 68b while the second detent 62b is forced over the outer surface of the housing 68. In order for the locking ring 62 to be rotated to its other position, e.g., in a clockwise direction, as shown in FIG. 38A, it must be rotated with a predetermined minimal force, e.g., a force greater than would be found accidentally during use, to cause the first detent 62a to be forced over the outer surface of the housing 68. When fully rotated in the clockwise direction, the second detent 62b may enter the cutout 68b, thereby provided a predetermined resistance to rotate the locking ring 62 again in the counterclockwise direction.

Turning to FIGS. 39A-39C, an exemplary embodiment of a surgical tool 410 is shown that includes a control shaft 412 and a handle 414, and has a modular tool head 460 coupled to the control shaft 412. Generally, similar to other embodiments described herein and in the references incorporated by reference herein, the control shaft 412 includes an outer cannular tube or shaft 420 and an inner "active" shaft 430 that are movable relative to one another, e.g., axially and/or rotationally, as described elsewhere herein. In addition, the outer and inner shafts 420, 430 include features, e.g., on distal ends 422, 432 as shown in FIGS. 40 and 41, for engaging corresponding features on the tool head 460, e.g., to couple the tool head 460 to the control shaft 412 and/or actuate an end effector 480 on the tool head 460, also as described further below.

Figure 40A:
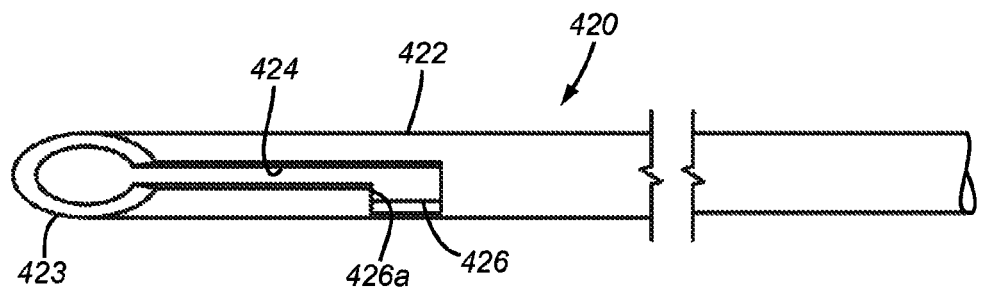
FIGS. 40A and 40B are top and side views, respectively, of an exemplary embodiment of an outer cannular shaft that may included in the control shaft of the surgical tool of FIGS. 39A-39C.
Figure 40B:
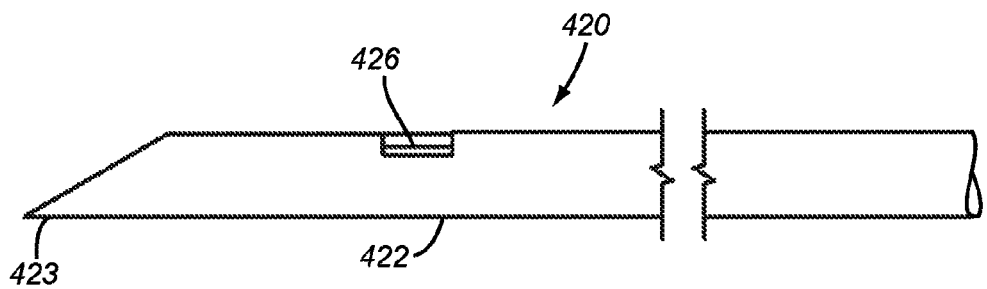
Figure 41A:
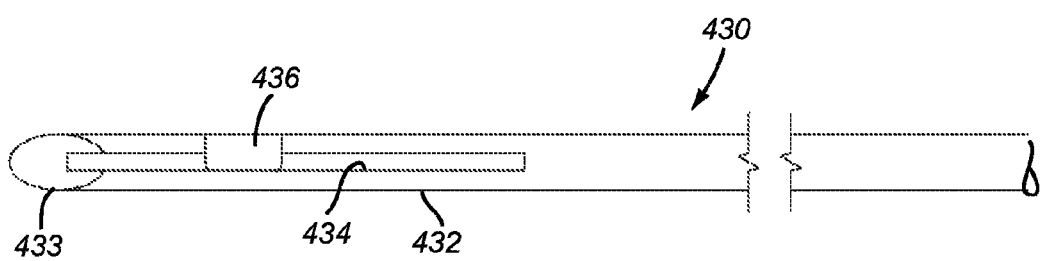
FIGS. 41A and 41B are top and side views, respectively, of an exemplary embodiment of an inner "active" shaft tube that may included in the control shaft of the surgical tool of FIGS. 39A-39C.
Figure 41B:
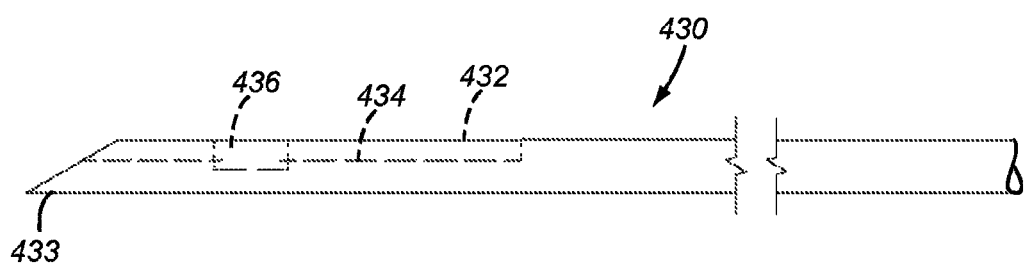

For example, as shown in FIGS. 40A and 40B, the distal end 422 of the outer cannular shaft 420 includes a longitudinal slot 424, e.g., extending proximally from a distal tip 423 of the cannular shaft 420 to an angular pocket 426 that extends laterally from the slot 424 to provide a blunt distal edge 426a. As shown in FIGS. 41A and 41B, the inner shaft 430 also includes a longitudinal slot 424, e.g., extending proximally from a distal tip 433 of the inner shaft 430. An angular notch 436 is provided in the distal end 432 at an intermediate location along the slot 434. Initially, the slots 424, 434 may be aligned with one another, e.g., to accommodate receiving the tool head 460 onto the control shaft 412, yet may be directed out of alignment with one another, e.g., by rotating the outer shaft 420 relative to the inner shaft 430 (or vice versa), to secure the tool head 460 to the control shaft 412, as shown in FIGS. 51A-52B and described further below.

The distal tips 423, 433 may be generally coextensive with one another, e.g., as shown in FIGS. 49A and 49B, although the distal tip 433 of the inner shaft 430 may extend from or retract into the distal end 422 of the outer cannular shaft 420, e.g., when the inner shaft 430 is directed axially relative to the outer cannular shaft 420, e.g., as shown in FIG. 49C. As shown, the distal tips 423, 433 are beveled, e.g., sharpened to facilitate penetration through tissue, if desired, and/or to facilitate insertion into the tool head 460. Alternatively, the distal tips 423, 433 may be blunt or have other configurations, as desired.

Returning to FIGS. 39A-39C, the handle 414 includes a stationary housing 440 from which a hand rest 442 extends, e.g., configured to be held by a user. The outer cannular shaft 420 may be substantially fixed axially relative to the housing 440, yet may be rotatable relative to the housing 440 and inner shaft 430. The inner shaft 430 may substantially fixed rotationally, yet may be movable axially relative to the housing 440 and outer shaft 420.

For example, a proximal end 421 of the outer shaft 420 may be rotatably mounted within the housing 440, e.g., using rotatable bearings or bushings (not shown), and an actuator 444 may be coupled to the proximal end 421 and rotatable relative to the housing 440 to rotate the outer shaft 420 relative to the inner shaft 430, e.g., to lock or unlock the tool head 460 from the control shaft 412, as described further below. Optionally, the actuator 444 may be limited to rotate between two positions, e.g., a first position corresponding to the control shaft 412 being disengaged from the tool head 460 and a second position corresponding to the control shaft 412 being engaged to the tool head 460, as described elsewhere herein. In this embodiment, the actuator 444 and/or housing 440 may include cooperating features to releasably secure the actuator 444 in the first and second positions. Alternatively, if desired, the actuator 444 may be coupled to the inner shaft 430, which may be rotatable and the outer shaft 420 may be rotationally fixed, such that the actuator 444 may rotate the inner shaft 430 relative to the stationary outer shaft 420 to lock or unlock the tool head 460 from the control shaft 412.

The handle 414 also includes a trigger or other actuator 446 coupled to the inner shaft 430, e.g., for directing the inner shaft 430 axially relative to the outer cannular shaft 420. For example, with the tool head 460 coupled to the control shaft 412, the trigger 446 may be activated to direct the inner shaft 420 axially to, in turn, direct an end effector 480 of the tool head 460 between open and closed positions, as shown in FIGS. 39A and 39B, and described further below.

Optionally, as shown, the handle 440 may include an alignment actuator 448 for limiting movement of the inner shaft 430 proximally beyond an alignment position, e.g., with the trigger 446 in the closed position. For example, with the trigger 446 and the end effector 480 in the closed position shown in FIG. 39B, the alignment actuator 448 may directed from an operational position (shown in FIGS. 39A and 39B) to an alignment position (shown in FIG. 39C). For example, in the operational position, the actuator 446 may be used to direct the end effector 480 between the open and closed positions, while in the alignment position, with the actuator 446 in the closed position, components of the tool head 460 and control shaft 412 may be aligned to allow the tool head 460 to be separated from (or coupled to) the control shaft 412, e.g., as shown in FIGS. 56A and 56B and described further below.

Turning to FIGS. 42A-47B, an exemplary embodiment of a tool head or end effector assembly 460 is shown that may be selectively coupled to the shaft 412 of the surgical tool 410 of FIGS. 39A-39C, e.g., as shown in FIGS. 48A-52B. As shown in FIGS. 42A-42E, the tool head 460 includes a housing 470, an end effector 480, an actuating link 490 movable axially relative to the housing 470 and coupled to the end effector 480, a locking ring 500, and a guide cap 510, generally similar to embodiments in the references incorporated by reference herein.

With particular reference to FIGS. 43A-43F, the housing 470 includes an elongate tubular body 472 including a passage 474 extending between proximal and distal ends 472a, 472b thereof, a proximal collar 476 for receiving the locking ring 500 and guide cap 510 thereon, and a pair of distal supports 478 for supporting the end effector 480. As best seen in FIGS. 43A and 43F, the proximal collar 476 includes an angular slot 476a such that the collar 476 has a generally "C" shaped cross-section providing stops 476b, 476c, e.g., to limit rotation of the locking ring 500, as described further below. The distal supports 478 are spaced apart from one another to define a gap or slot 478a therebetween for receiving the end effector 480 and/or to slidably receive the actuating link 490 therein, as described further below. As shown, the distal supports 478 include apertures 478b therethrough for receiving a pin or other connector (not shown) for rotatably coupling the end effector 480 to the supports 478, also as described further below. In addition, a slot 472e is provided in the distal end 472b of the housing 472, e.g., aligned with the gap 478a between the supports 478, which may limit motion of the actuating link 490.

Optionally, the housing 470 may include a plurality of longitudinal grooves or slots 472c formed in or otherwise extending along its outer surface between the proximal and distal ends 472a, 472b, e.g., to accommodate releasably securing the tool head 460 to an introduction device, as described elsewhere herein. As shown, the grooves 472c include widened or tapered distal regions 472d adjacent the distal end 472b, e.g., for guiding mating features on an introduction device (not shown) into the grooves 472c.

Figure 44A:
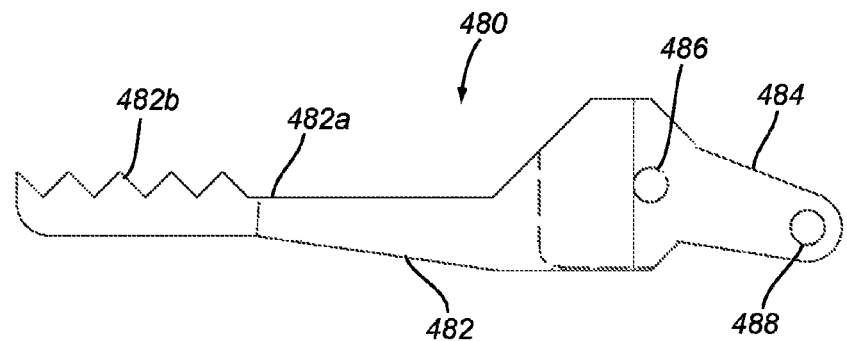
FIGS. 44A-44C are side and left and right perspective views of an exemplary embodiment of an end effector of the tool head.
Figure 44B:
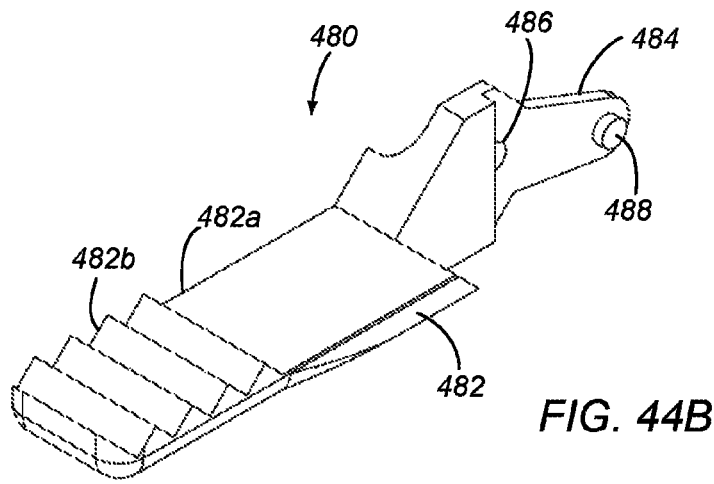
Figure 44C:
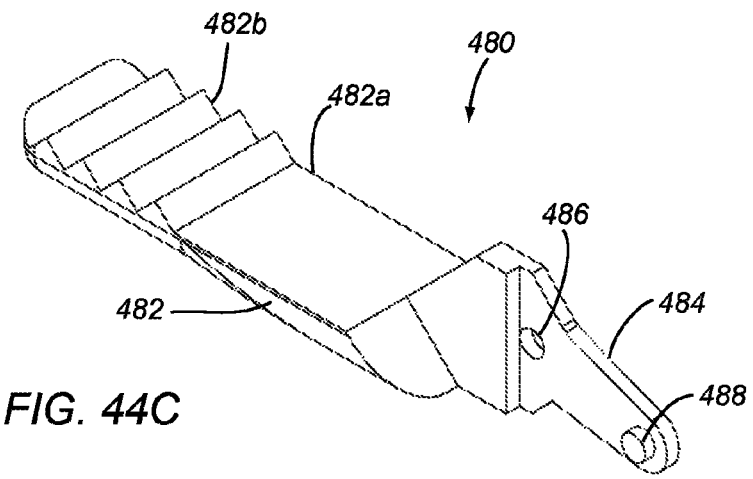

Turning to FIGS. 44A-44C, the end effector includes a pair of grasper elements 480 that each includes first and second ends 482, 484 on opposite sides of an aperture 486 extending through the end effector 480 to provide a pivot axis 486a (shown in FIGS. 42A and 42B). The first end 482 includes an elongate jaw element 482a, e.g., including a plurality of teeth or other gripping features 482b. The second end 484 includes a tab 488 that may be slidably engaged with the actuating link 490, as described further below. It will be appreciated that other cooperating elements may be provided instead of the grasper elements 480 on the tool head 460, e.g., curved and/or tapered elements (not shown) instead of the substantially flat elements shown, as described elsewhere herein and in the references incorporated by reference herein.

Turning to FIGS. 45A-45E, the actuating link 490 includes a tubular portion 492 and a planar track member 494 extending from the tubular portion 492. The tubular portion 492 may be sized to be slidably received in the passage 474 in the housing 470, and include first and second ends 492a, 492b and a passage 492c therebetween. The track member 494 may be a generally flat or planar member that includes a pair of diagonal slots 494a therein for slidably receiving the tabs 488 of the grasper elements of the end effector 480, e.g., as shown in FIGS. 49A-49C. In addition, the tubular portion 492 includes a longitudinal translation channel 496 extending from the first end 492a partially towards the second end 492b. A lateral pocket 496a extends from the translation channel 496 transverse to a longitudinal axis of the actuating link 490. As shown, the lateral pocket 496a may be located at an intermediate location along the translation channel 496, e.g., such that a relatively short channel extension 496b is provided past the lateral pocket 496a away from the first end 492a.

As described further below, the lateral pocket 496a may define a stop 496c, which may provide a safety feature that prevents undesired actuation of the end effector 480, e.g., before the tool head 460 has been fully coupled onto a control shaft 412 (not shown). In addition, the channel extension 496b may provide a predetermined amount of additional proximal travel of the actuating link 490, e.g., to close the end effector 480 with a desired enhanced closing force, also as described further below.

The actuating link 490 also includes an actuator key or tooth 498 extending inwardly within the passage 492c, e.g., at an intermediate location between the proximal and distal ends 492a, 492b of the tubular portion 492, e.g., spaced apart distally from the translation channel 496.

Figure 45F:
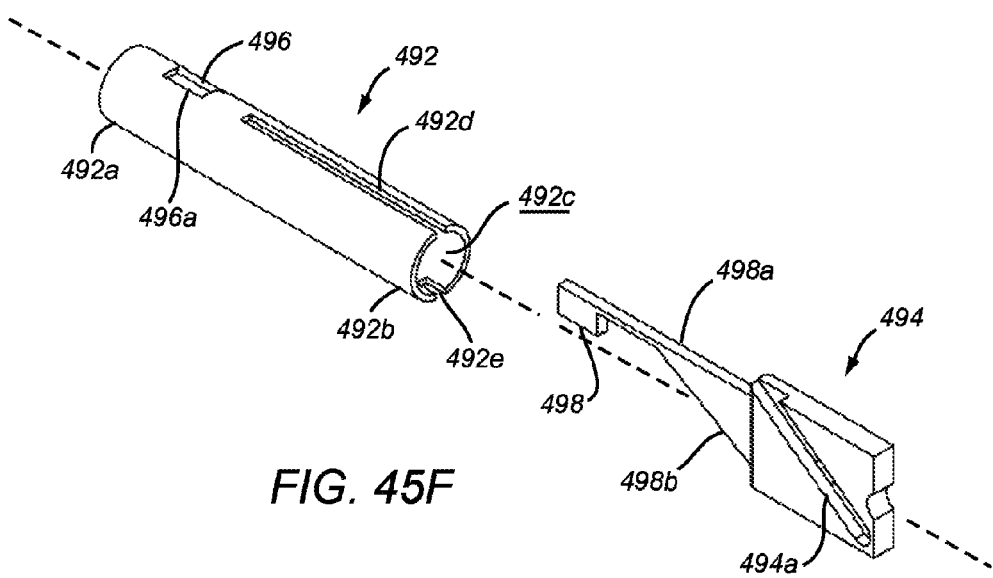
FIGS. 45F-45H are exploded views of an exemplary embodiment of the actuating link formed from two components.
Figure 45G:
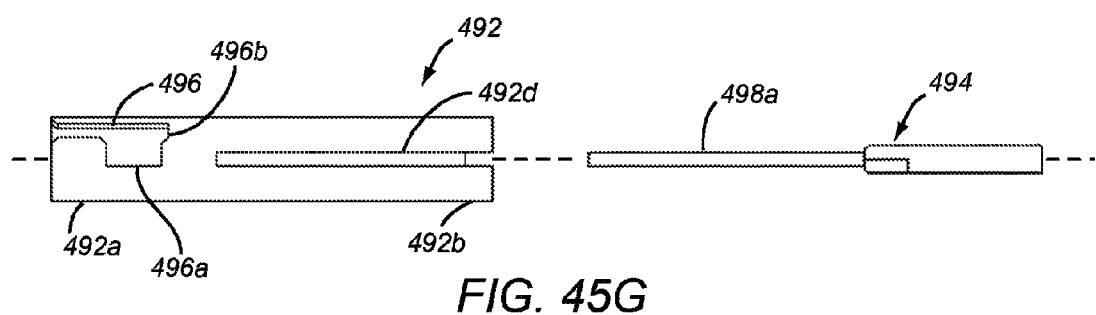
Figure 45H:
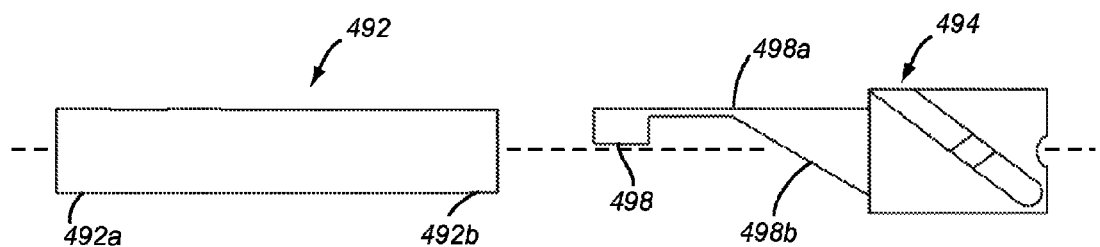
Figure 46A:
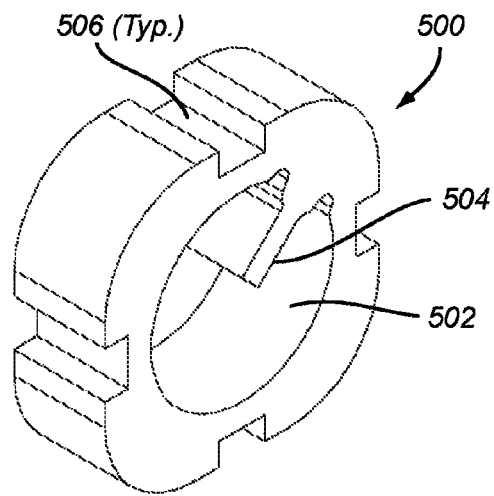
FIGS. 46A and 46B are perspective views of an exemplary embodiment of a locking ring that may be rotatably coupled to the housing of the tool head.
Figure 46B:
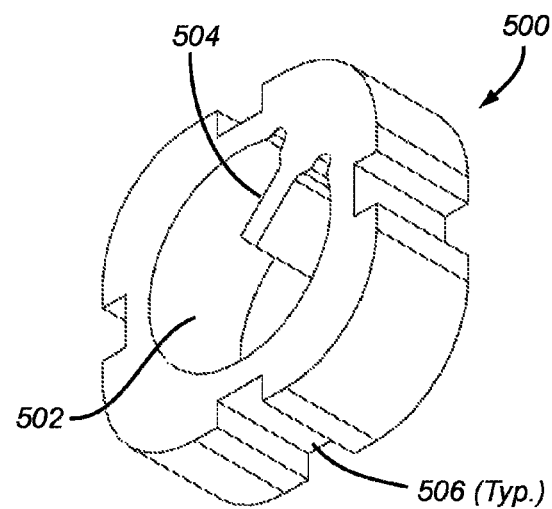
Figure 46C:
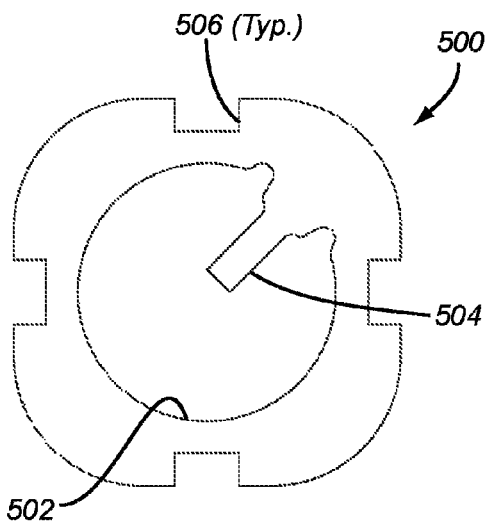
FIGS. 46C and 46D are end and top views, respectively, of the locking ring.
Figure 46D:
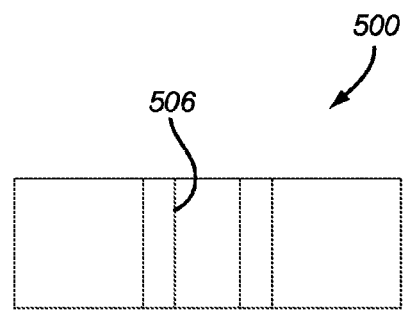

FIGS. 45F-45H show an exemplary embodiment of the actuating link 490 formed from two components, namely a separate tubular portion 492 and track member 494, that are attached together. For example, as shown, the tubular portion 492 includes a longitudinal slot 492d that extends from the second end 492b partially towards the first end 492a. The track member 494 includes an extension 498a sized to be received within the slot 492a and includes the actuating tooth 498 thereon. Optionally, the track member extension 498a may include a beveled or tapered surface 498b, e.g., to accommodate receiving distal tips of a control shaft (not shown) immediately adjacent the extension 498a when the tool head 460 is being coupled to the control shaft.

To assemble the actuating link 490, the extension 498a may be inserted into the slot 492d to position the actuating tooth 498 at the desired axial location within the passage 492c. Optionally, the tubular portion 492 may include a pocket 492e in the second end 492b opposite the slot 492d, e.g., to receive a corresponding feature on the extension 498a therein, e.g., a lower edge of the tapered surface 498b, to support the components together. The tubular portion 492 and track member 494 may be attached together, e.g., by one or more of an interference fit, bonding with adhesive, welding, fusing, and the like. In an alternative embodiment, the actuating link 490 may formed from one or more than two components, e.g., by molding, machining, and the like.

Turning to FIGS. 46A-46D, the locking ring 500 includes an annular body including a passage 502 sized to rotatably receive the collar 476 of the housing 470 therein (not shown, see, e.g., FIGS. 49A-49C, 51A, and 52A). In addition, the locking ring 500 includes a locking key or tooth 504 extending inwardly into the passage 502, e.g., sized to be slidably received in the longitudinal slots 424, 434 of the outer and inner shafts 420, 430, as described elsewhere herein. Optionally, the locking ring 500 may include a plurality of grooves or slots 506 formed in or otherwise extending along the outer surface of the locking ring 500, similar to the grooves 472c in the housing 470, e.g., to accommodate releasably securing the tool head 460 to an introduction device.

Figure 47A:
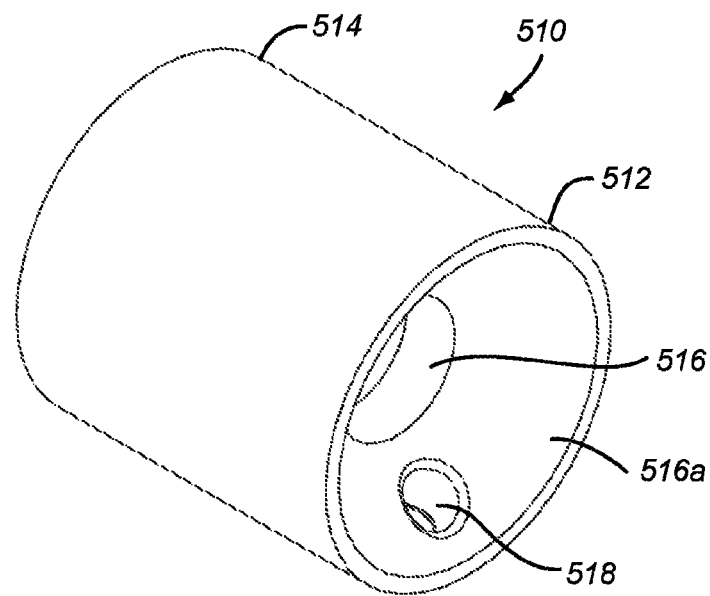
FIGS. 47A and 47B are perspective and end views, respectively, of a guide cap that may be coupled to the housing of the tool head.
Figure 47B:
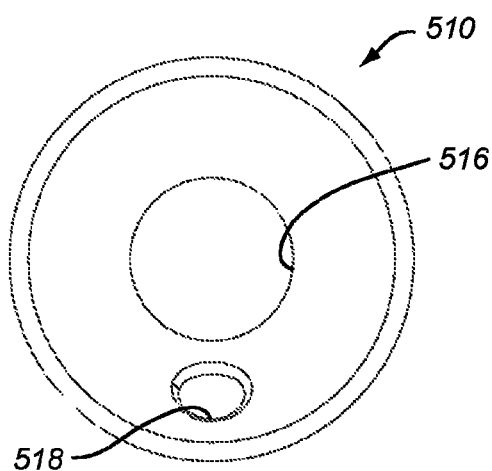

Turning to FIGS. 47A and 47B, the guide cap 510 generally includes a cylindrical body including first and second ends 512, 514 and a passage 516 extending therebetween sized to receive a control shaft (not shown) therein. As shown, the first end 512 includes a tapered surface 516a communicating with the passage 516, e.g., to guide the distal tip of the control shaft into the passage 516 and into the housing 470. The guide cap 510 may include a recess 514a in the second end 514 for receiving the collar 476 therein. Optionally, the guide cap 510 and/or collar 476 may include one or more connectors (not shown) for attaching the guide cap 510 to the collar 476 and/or the guide cap 510 may attached to the collar 475, e.g., by one or more of an interference fit, bonding with adhesive, welding, fusing, and the like.

Optionally, as shown, the guide cap 510 may include a hole 518 therethrough, e.g., extending between the tapered surface 516a and an outer surface of the guide cap 510. The hole 518 may be sized to receive a suture, wire, or other tether (not shown) therethrough. For example, a tether may be secured through the hole 518 to allow retrieval of the tool head 460, e.g., if the tool head 460 somehow becomes loose within a surgical space. In addition, the hole 518 may receive a rail, such as the wire or filament 74 shown in FIG. 13, which may be used to introduce and/or orient the tool head 460, similar to other systems and methods herein. Alternatively, a similar hole or other feature (not shown) may be provided on another component of the tool head 460 if desired.

Returning to FIGS. 42A-42E, the tool head 460 may be manufactured and assembled using similar materials and methods disclosed in the references incorporated by reference elsewhere herein. For example, the pair of graspers of the end effector 480 may be oriented with their jaws 482 oriented towards one another, as shown in FIGS. 42A-42C, and the tabs 488 received within respective tracks 494a of the track member 494 of the actuating link 490, e.g., as can be seen in FIGS. 49A-49C and 55A-56B. The first end 492a of the tubular portion 492 of the actuating link 490 may be inserted into the housing 470, e.g., between the supports 478. The track member 478 may be aligned such that the narrow width of the track member 478 is aligned with and slidably received in the slots 472e in the distal end 472b of the housing 470, as can be seen in FIGS. 42A, 42B, and 42D.

The apertures 486 in the end effector 480 may be aligned with the apertures 478b in the supports, and a pin or other axle member (not shown) may be received through the apertures to secure the end effector 480 to the supports 478. The pin may prevent substantial translational movement of the end effector 480 while accommodating rotation about the axis 486a, e.g., to open and close the jaw elements 482s of the end effector 480. As can be seen in FIGS. 49A-49C, the actuating link 490 may be slidable axially within the housing 470, e.g., between proximal and distal positions shown in FIGS. 49B and 49C, respectively. When the actuating link 490 is in the proximal position, the tabs 488 of the end effector 480 may be directed into distal regions of the respective tracks 494a, thereby closing the end effector 480, as shown in FIG. 49B. As the actuating link 490 is directed to the distal position, e.g., as the track member 494 extends at least partially from the distal end 472b of the housing 470, the tabs 488 travel along the tracks 494a, e.g., to proximal regions of the respective tracks 494a. Due to the diagonal orientation of the tracks 494a, the end effector 480 is opened as the tabs 488 move to the proximal regions of the tracks 494a, as shown in FIG. 49C.

Returning to FIGS. 42A-42E, to complete assembly of the tool head 460, the locking ring 500 may be directed over the collar 476 of the housing 470, e.g., with the locking tooth 504 aligned within the angular slot 476a of the collar 476. The guide cap 510 may then be received over the collar 476 and secured thereto, e.g., such that the locking ring 500 is substantially axially fixed relative to the collar 476 but is free to rotate around the collar 476. With the locking tooth 504 received within the angular slot 476a, however, rotation of the locking ring 500 may be limited by the stops 476b, 476c defined by the slot 476a, as described further below.

Turning to FIGS. 48A-50, the tool head 460 may be coupled to the control shaft 412, e.g., within a patient's body, such as within a surgical space using an endoscope and/or a tool carrier (not shown), similar the embodiments described elsewhere herein and/or in the references incorporated by reference herein. For example, the tool head 460 may be connected to a tool carrier (not shown) and introduced into the surgical space independently of the control shaft 412. In an exemplary embodiment, connectors on the tool carrier (also not shown) may be directed along the grooves 472, 506 of the housing 470 and locking ring 500, with the grooves 472, 506 aligned, e.g., as shown in FIGS. 42A-42D and 48B, such that the connectors are received in the grooves 506 of the locking ring 500. Once the connectors are received within the grooves 506, the locking ring 500 may be rotated such that the grooves 472, 506 are out of alignment, e.g., as shown in FIGS. 48A and 50, thereby preventing the connectors from escaping and coupling the tool head 460 to the tool carrier.

With the locking ring 500 rotated as shown in FIGS. 48A and 50, the tool head 460 is considered to be in an unlocked or disengaged configuration. In this orientation, the locking tooth 504 may contact the first stop 476b on the collar 476, as best seen in FIG. 51A. In addition, in the unlocked configuration, the actuating tooth 498 is axially aligned with the locking tooth 504. For example, as shown in FIGS. 51A and 51B, both the locking tooth 504 and the actuating tooth 498 may be oriented upwardly or at a "12:00 clock position."

Figure 54C:
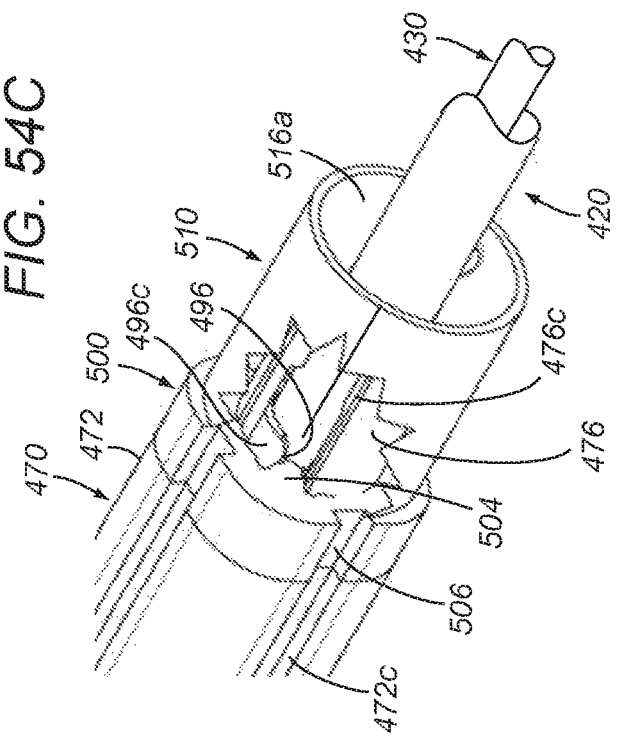

With additional reference to FIGS. 53A and 54A, in the unlocked configuration, the locking tooth 504 may be abutting the first stop 476b of the collar 476. In addition, the locking tooth 504 may be received within the pocket 496a behind the stop 496c on the actuating link 490, with the end effector 480 in the closed position and/or the actuating link 490 in its proximal position within the housing 470. Thus, with the locking tooth 504 received within the pocket 496a, the stop 496c prevents the actuating link 490 from moving distally, which may otherwise allow the end effector 480 to open.

A control shaft 412 of a surgical tool, such as the tool 410 shown in FIGS. 39A-39C, may be received within and coupled to the tool head 460. Initially, the outer and inner shafts 420, 430 may be rotationally aligned such that their longitudinal slots 424, 434 are also aligned with one another. The distal ends 422, 432 of the shafts 420, 430 may then be inserted into the passage 516 of the guide cap 510 and into the collar 476 and tubular portion 492 of the actuating link 490, e.g., as shown in FIGS. 49A, 53A, 54A, 55A, and 56A. As best seen in FIG. 56A, the tapered surface 516a of the guide cap 516 may facilitate inserting the distal ends 422, 432 of the control shaft 412 into the passage 516, which may have a relatively close fit around the outer shaft 420, e.g., to minimize lateral movement of the control shaft 412 relative to the components of the tool head 460.

As best seen in FIG. 51A, as the distal ends 422, 432 of the shafts 420, 430 enter the collar 465, the locking tooth 504 may enter and slide along the longitudinal slots 424, 434 in the shafts 420, 430. Thus, the locking tooth 504 may have a height extending inwardly sufficient distance to be received through the slot 424 of the outer cannular shaft 420 and into the slot 434 of the inner shaft 430. In addition, the locking tooth 504 may have a width to accommodate being slidably received within the longitudinal slots 424, 434 without excessive space between the wall of the slots 424, 434 and the locking tooth 504, e.g., to maintain the shafts 420, 430 in a desired rotational alignment with the tool head 460.

In addition, as the distal ends 422, 432 of the shafts 420, 430 enter the passage 492c in the tubular portion 492 of the actuating link 490, the actuating tooth 498 may be slidably received within the longitudinal slots 424, 434, similar to the locking tooth 504, although the actuating tooth 498 is offset distally from the locking tooth 504. Thus, the actuating tooth 498 may also have a height and width to be slidably received within the slots 424, 434. Advancement of the control shaft 412 may continue until the locking tooth 504 reaches the end of the longitudinal slot 424 of the outer cannular shaft 420, whereupon the control shaft 412 cannot be advanced further, providing tactile feedback to the user that the control shaft 412 has been fully seated in the tool head 460.

Once fully received within the tool head 460, the locking tooth 504 may be axially aligned with the angular pocket 426 extending from the slot 424, shown in FIGS. 40A and 40B. Similarly, the actuating tooth 498 may be axially aligned with the notch 436 in the inner shaft 430, e.g., as shown in FIGS. 49A-49C, 56A, and 56B.

With additional reference to FIGS. 39A-39C, the actuator 444 on the handle 414 may then be rotated or otherwise activated, e.g., rotated clockwise from a proximal perspective above the handle 414 of the surgical tool 410, to rotate the outer cannular shaft 420 relative to the inner shaft 430. It will be appreciated that, in an alternative embodiment, the actuator 444 may be coupled to the inner shaft 430 such that the inner shaft 430 may be rotated counterclockwise relative to the outer cannular shaft 420 to achieve the same result and configuration described below. As can be seen in FIGS. 52A and 52B, once the outer shaft 420 is rotated, the longitudinal slot 434 of the inner shaft 430 is then out of alignment with the longitudinal slot 424 of the outer cannular shaft 420.

As shown in FIGS. 51A and 52A, with the actuating tooth 498 received in the longitudinal slot 424, rotation of the outer shaft 420 causes corresponding rotation of the housing 470 and actuating link 490 relative to the locking ring 500. For example, the locking ring 500 may remain substantially stationary, e.g., if coupled to a tool carrier or other introduction device (not shown) used to introduce the tool head 460 into the surgical space.

As the outer shaft 420 is rotated relative to the locking ring 500, the locking tooth 504 (stationary on the locking ring 500) may be directed from the slot 424 into the angular pocket 426. The length of the locking tooth 504 may be similar to the length of the pocket 426 such that the blunt distal edge 426a of the pocket 426 prevents subsequent axial movement of the tool head 460 relative to the outer cannular shaft 420. Thus, the tool head 460 may become substantially fixed relative to the outer shaft 420 such that movement of the handle 414 of the surgical tool 410 translates to corresponding movement of the tool head 460.

Rotation of the outer shaft 420 may be limited by the depth of the angular pocket 426, e.g., such that when the locking tooth 504 fully enters the angular pocket 426, further rotation is prevented. In addition or alternatively, as the housing 470 is rotated, the locking tooth 504 may abut the stop 476c on the collar 476, thereby also preventing further rotation.

The rotation of the housing 470 and actuating link 490 by the outer shaft 420 also causes the locking tooth 504 to be directed out of the lateral pocket 496a in the tubular portion 492 of the actuating link 490 and into the translation channel 496, as best seen in FIGS. 54A and 54B. For example, as shown, the outer shaft 420 and actuating tooth 500 have been rotated clockwise such that the relative position of the locking tooth 504 (and slot 434 of the inner shaft 430) is at about a "10:00 position" while the actuating tooth 498 (and outer cannular shaft 420) has been rotated to about a "12:00 position."

Substantially simultaneously, as the outer shaft 420 is rotated, the actuator tooth 498 may be received in the notch 436 in the inner shaft 430, thereby coupling subsequent movement of the actuating link 490 to the inner shaft 430. For example, the actuator tooth 498 may have a length and/or other size to be received within the notch 436 with minimal gaps. Thus, with the actuator tooth 498 engaged with the notch 436 and the locking tooth 504 within the translation channel 496, the actuating link 490 may be free to move axially relative to the locking ring 500 and consequently the housing 470.

Also as the housing 470 is rotated relative to the locking ring 500, the grooves 472c, 506 on the housing 470 and locking ring 500 may again be aligned, thereby allowing the connectors of the tool carrier (not shown) to be slid from the grooves 506 through the grooves 472c, thereby disengaging the tool head 460 from the tool carrier. The tool carrier may then be removed from the surgical space and the tool 410 used during a surgical procedure within the surgical space, e.g., as described elsewhere herein and in the references incorporated by reference herein.

Figure 53C:
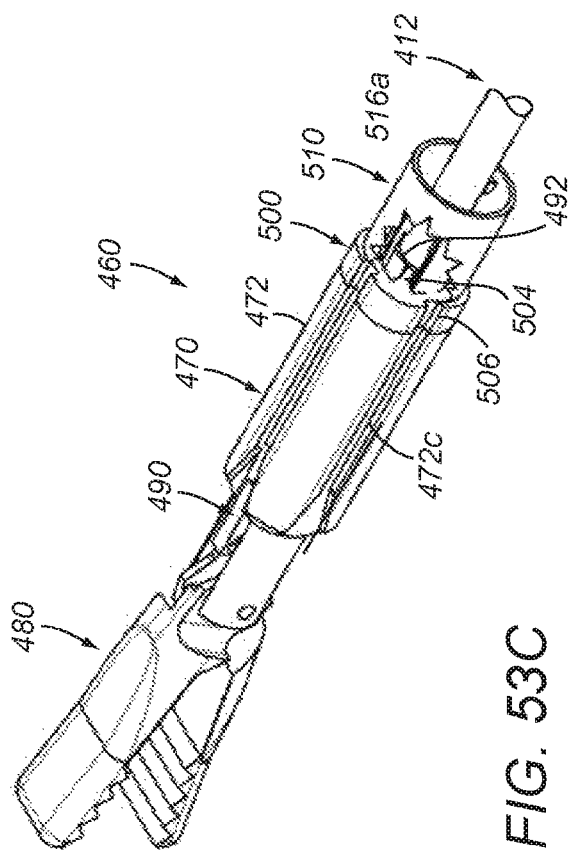

For example, as shown in FIGS. 49B, 53B, and 55B, the inner shaft 430 may be provided in a proximal position in which the end effector 480 is closed, and may be movable distally to cause the actuating link 490 to advance distally, thereby opening the end effector 480, e.g., as shown in FIGS. 49C, 53C, and 55C. With additional reference to FIGS. 39A and 39B, the trigger 446 may be coupled to a proximal end 431 of the inner shaft 430 such that the trigger 446 may be selectively activated by the user to direct the inner shaft 430 between the proximal and distal positions to close the end effector 480 (FIG. 39B) and open the end effector (FIG. 39C).

When it is desired to remove the tool head 460, e.g., upon completion of a procedure or to exchange the tool head 460 for another tool head (not shown), the trigger 446 may be activated to close the end effector 480 and prepare the tool head 460 for removal. Optionally, as shown in FIGS. 39A-39C, the handle 416 of the tool 410 may include an alignment actuator 448 for aligning the components of the tool head 460 in a predetermined "alignment" position to allow disengagement of the tool head 460 from the control shaft 412.

For example, during use, the trigger 446 may be activated to close the end effector 480 with a desired engagement force, e.g., to grasp or otherwise engage tissue or other structures (not shown) during the procedure. To maximize such force applied by the end effector 480, the inner shaft 430 may be retracted to direct the tabs 448 of the end effector 480 to a distal-most position within the tracks 494a, e.g., as shown in FIG. 56B. In this distal-most position, however, the locking tooth 504 may be received in the channel extension 496b of the translation channel 496, i.e., such that the locking tooth 504 is not aligned with the lateral pocket 496a (shown in FIGS. FIGS. 45A-45D) in the tubular portion 492 of the actuating link 490, as can be seen in FIGS. 39A(1) and 56B. Optionally, the handle 416 may include a ratchet or other mechanism, similar to other embodiments herein (not shown), for releasably securing the end effector 480 in this closed position.

For example, with the trigger 446 and end effector 480 in the closed position, e.g., shown in FIGS. 39B, 49B, 53B, 55B, and 56B, the actuator 448 may be activated to provide a stop preventing the inner shaft 430 from being retracted proximally beyond a predetermined location, e.g., to limit the inner shaft 430 to the alignment position corresponding to the offset of the channel extension 496b. Thus, as shown in FIGS. 39C, 39C(1), when the inner shaft 430 is retracted, the actuating link 490 is also refracted, thereby directing the locking tooth 504 from the channel extension 496b and into alignment with the pocket 496a. Alternatively, the actuator 448 may override the actuator 446 and direct the inner shaft 430 to the alignment position independent of the position of the actuator 446.

In this position, a tool carrier may be directed over the housing 470, e.g., by advancing connectors on the tool carrier along the grooves 472c into the grooves 506 of the locking ring 500. The actuator 444 may then be rotated or otherwise activated to rotate the outer cannular shaft 420 back into alignment with inner shaft 430. For example, similar to the process described above, the outer cannular shaft 420 may rotate the housing 470 and actuating link 490 relative to the locking ring 500 to direct the locking tooth 504 out of the angular pocket 426 into the longitudinal slot 424 of the outer cannular shaft 420 and substantially simultaneously into the lateral pocket 496a in the tubular portion of the actuating link 490. This action also disengages the actuator tooth 498 from the notch 436 and directs the grooves 506 on the locking ring 500 out of alignment from the grooves 472c on the housing 470. Thus, the control shaft 412 may be withdrawn, causing the actuator tooth 498 and locking tooth 504 to slide along the longitudinal slots 424, 434 until the distal ends 422, 432 of the shafts 420, 430 are removed from the passage 516 in the guide cap 510. The tool head 460, again coupled to the tool carrier, may be removed from the surgical space or otherwise exchanged for another tool head.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A system for performing a procedure within a surgical space within a patient's body, comprising:
    a surgical tool comprising an elongate control shaft including a distal end sized for introduction into a surgical space, and a handle on the control shaft distal end; and
    a tool head comprising a housing including a housing proximal end for receiving the control shaft distal end therein, and a housing distal end, an end effector movably mounted to the housing distal end, an actuator link movable relative to the housing and coupled to the end effector for directing the end effector between first and second positions, and a locking element rotatably mounted on the housing,
    the locking element and control shaft distal end comprising cooperating connectors, the surgical tool comprising first and second actuators on the handle, the first actuator connectable to the locking element for rotating the locking element between a) a first orientation where the locking element is coupled to the actuator link to prevent substantial movement of the actuator link to prevent actuation of the end effector and the cooperating connectors are disconnected and control shaft distal end is insertable into and removable from the housing proximal end and b) a second orientation where the cooperating connectors substantially fix the control shaft distal end relative to the housing and couple the second actuator to the actuator link while releasing the actuator link from the locking element, the second actuator activatable for directing the actuator link to direct the end effector between the first and second positions,
    wherein the locking element comprises a locking key that is received in a pocket in the actuator link in the first orientation for preventing substantial movement of the actuator link to prevent actuation of the end effector, the locking key being directed into a translation channel in the second orientation, the translation channel configured to allow the actuator link to move axially relative to the housing between distal and proximal locations to direct the end effector between the first and second positions, respectively.

2. The system of claim 1, wherein the end effector comprises a grasper and wherein the first and second positions comprise open and closed positions of the grasper, respectively.

3. The system of claim 2, wherein the translation channel comprises an axial extension distally beyond the pocket that allows the actuator link to be directed to a proximal-most location proximally beyond the proximal location to impose a clamping force on jaw elements of the grasper in the closed position.

4. The system of claim 3, wherein the handle comprises a third actuator for directing the actuator link axially to align the pocket with the locking key with the locking element in the second orientation and the second actuator directing the grasper to the closed position, whereby the first actuator may be activated to direct the locking element to the first orientation.

5. The system of claim 1, further comprising a tool carrier including a proximal end, a distal end sized for introduction into a surgical space, and one or more introducer features on the distal end,
wherein the housing and locking element each comprise one or more grooves, wherein the one or more grooves on the housing and the one or more grooves on the locking element are aligned with one another in the second orientation such that the one or more introducer features may be directed into the one or more grooves on the housing and into the one or more grooves on the locking element, wherein the one or more grooves on the housing and the one or more grooves on the locking element are out of alignment with one another in the first orientation such that the introducer features cannot be removed from the one or more grooves on the locking element, thereby securing the tool head to the tool carrier.

6. The system of claim 1, wherein the control shaft comprises an outer shaft and an inner shaft, wherein the cooperating connectors comprise the locking key extending from the locking element and an actuator key extending from the actuator link, and longitudinal slots in the outer and inner shafts that slidably receive the locking key and actuator key when the control shaft distal end is inserted into the proximal end of the housing.

7. A modular tool head for performing a procedure within a surgical space within a patient's body when the tool head is connected to a surgical tool including a control shaft comprising an inner and an outer shaft including a distal end sized for introduction into the surgical space, the tool head comprising:
a housing including a proximal end sized for receiving the distal end of the control shaft therein, a housing distal end, and an end effector including a pair of opposing end effector elements pivotably coupled to the housing distal end;
an actuator link movable relative to the housing and coupled to the end effector elements for directing the end effector between open and closed positions;
a locking element rotatable on the housing, the locking element comprising connectors for engaging one or both of the inner and outer shafts, the locking element rotatable between first and second orientations on the housing, wherein a) in the first orientation, the locking element is coupled to the actuator link to prevent substantial movement of the actuator link to prevent actuation of the end effector and the connectors are disconnected from the control shaft distal end such that the control shaft is insertable into and removable from the housing proximal end and b) in the second orientation, the connectors substantially fix the control shaft distal end relative to the housing and couple an actuator on the surgical tool to the actuator link while releasing the actuator link from the locking element, the actuator activatable for directing the actuator link to direct the end effector elements between the open and closed positions,
wherein the locking element comprises a locking key that is received in a pocket in the actuator link in the first orientation, the locking key being directed into a translation channel in the second orientation, the translation channel configured to allow the actuator link to move axially relative to the housing between distal and proximal locations to direct the end effector elements between the open and closed positions, respectively.

8. The tool head of claim 7, wherein the end effector comprises a grasper.

9. The tool head of claim 8, wherein the translation channel comprises an axial extension distally beyond the pocket that allows the actuator link to be directed to a proximal-most location proximally beyond the proximal location to impose a clamping force on jaw elements of the grasper in the closed position.

10. A system for performing a procedure within a surgical space within a patient's body, comprising:
a tool head according to claim 7;
an introduction tool comprising a distal end sized to be introduced into a surgical space;
a surgical tool comprising a control shaft including a distal end sized to be introduced into a surgical space independently of the introduction tool distal end, and comprising a first actuator for coupling the tool head to the control shaft distal end;
the tool head configured to be coupled to the introduction tool distal end in a first static position and receive the control shaft distal end therein in the first static position, whereupon the first actuator may be activated to rotate the locking element relative to the introduction tool distal end, thereby directing the tool head to a second active position releasing the tool head from the introduction tool distal end.

11. The system of claim 10, wherein the surgical tool comprises a second actuator, the second actuator coupled to the end effector of the tool head after the first actuator directs the tool head to the second active position, whereupon the second actuator may be activated to operate the end effector.

12. The system of claim 11, wherein the end effector is locked with the tool head in the first static position.

13. The system of claim 12, wherein the end effector comprises a pair of jaws and the second actuator is configured for directing the jaws between open and closed positions with the tool head in the second active position, and wherein the jaws are locked in the closed position with the tool head in the first static position.

14. The system of claim 10, wherein the end effector comprises a grasper.

15. The system of claim 14, wherein the translation channel comprises an axial extension distally beyond the pocket that allows the actuator link to be directed to a proximal-most location proximally beyond the proximal location to impose a clamping force on jaw elements of the grasper in the closed position.

16. The system of claim 15, wherein the handle comprises a third actuator for directing the actuator link axially to align the pocket with the locking key with the locking element in the second orientation and the second actuator directing the grasper to the closed position, whereby the first actuator may be activated to direct the locking element to the first orientation.

17. The system of claim 10, further comprising a tool carrier including a proximal end, a distal end sized for introduction into a surgical space, and one or more introducer features on the distal end, wherein the housing and locking element each comprise one or more grooves, wherein the one or more grooves on the housing and the one or more grooves on the locking element are aligned with one another in the second orientation such that the one or more introducer features may be directed into the one or more grooves on the housing and into the one or more grooves on the locking element, wherein the one or more grooves on the housing and the one or more grooves on the locking element are out of alignment with one another in the first orientation such that the introducer features cannot be removed from the one or more grooves on the locking element, thereby securing the tool head to the tool carrier.

18. The system of claim 10, wherein the control shaft comprises an outer shaft and an inner shaft, wherein the cooperating connectors comprise a locking key extending from the locking element and an actuator key extending from the actuator link, and longitudinal slots in the outer and inner shafts that slidably receive the locking key and actuator key when the control shaft distal end is inserted into the proximal end of the housing.

* * * * *